(12) United States Patent
Santra et al.

(10) Patent No.: US 8,128,908 B2
(45) Date of Patent: Mar. 6, 2012

(54) NANOPARTICLES AND THEIR USE FOR MULTIFUNCTIONAL BIOIMAGING

(75) Inventors: Swadeshmukul Santra, Orlando, FL (US); Paul H. Holloway, Gainesville, FL (US); Robert A. Mericle, Brentwood, TN (US); Heesun Yang, Gainesville, FL (US); Glenn A. Walter, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1262 days.

(21) Appl. No.: 10/590,590

(22) PCT Filed: May 2, 2005

(86) PCT No.: PCT/US2005/015266
§ 371 (c)(1),
(2), (4) Date: May 7, 2007

(87) PCT Pub. No.: WO2005/107818
PCT Pub. Date: Nov. 17, 2005

(65) Prior Publication Data
US 2007/0269382 A1     Nov. 22, 2007

Related U.S. Application Data

(60) Provisional application No. 60/567,330, filed on Apr. 30, 2004.

(51) Int. Cl.
*A61B 5/00* (2006.01)
*A61B 5/055* (2006.01)
(52) U.S. Cl. ...... 424/9.6; 424/9.3; 424/9.32; 424/9.322; 424/9.323; 424/9.35; 424/9.36; 977/774
(58) Field of Classification Search ............... 424/9.6, 424/9.3, 9.32, 9.4, 9.322, 9.323, 9.35; 977/774
See application file for complete search history.

(56) References Cited

U.S. PATENT DOCUMENTS

| | | | |
|---|---|---|---|
| 4,466,896 A * | 8/1984 | Darden ............... 252/78.3 |
| 5,087,440 A | 2/1992 | Cacheris et al. |
| 5,155,215 A | 10/1992 | Ranney |
| 5,990,479 A | 11/1999 | Weiss et al. |
| 6,207,392 B1 | 3/2001 | Weiss et al. |
| 6,251,303 B1 | 6/2001 | Bawendi et al. |
| 6,322,901 B1 | 11/2001 | Bawendi et al. |
| 6,423,551 B1 | 7/2002 | Weiss et al. |
| 6,444,143 B2 | 9/2002 | Bawendi et al. |
| 6,649,138 B2 | 11/2003 | Adams et al. |
| 6,689,338 B2 * | 2/2004 | Kotov ............... 424/1.69 |
| 6,699,723 B1 | 3/2004 | Weiss et al. |
| 6,815,064 B2 | 11/2004 | Treadway et al. |
| 2003/0236457 A1 | 12/2003 | Mericle et al. |
| 2004/0023415 A1 | 2/2004 | Sokolov et al. |
| 2004/0067201 A1 | 4/2004 | Perkins et al. |
| 2005/0019842 A1 * | 1/2005 | Prober et al. ............ 435/7.9 |
| 2005/0136258 A1 * | 6/2005 | Nie et al. ............... 428/402 |
| 2005/0220714 A1 | 10/2005 | Kauzlarich et al. |
| 2005/0265922 A1 * | 12/2005 | Nie et al. .............. 424/1.11 |

FOREIGN PATENT DOCUMENTS

| WO | WO 01/89585 A1 | 11/2001 |
| WO | WO 2004/066361 A2 | 8/2004 |
| WO | WO 2005/041747 A2 | 5/2005 |

OTHER PUBLICATIONS

Alivisatos et al., "Quantum Dots as Cellular Probes" *Annu. Rev. Biomed. Eng.*, 2005, pp. 55-76, vol. 7.
Santra, S. "Multifunctional Nanoparticles for In Vivo Bioimaging Applications" presented at the University of Florida-Particle Engineering Research Center, Jul. 2, 2004.
Nie et al. "Luminescent Quantum Dots for Multiplexed Optical Tagging of Genes, Proteins, and Cells" *Cytometry*, 2002, pp. 25, vol. 25.
Wu, X. et al. "Labelilng Cellular Targets With Semiconductor Quantum Dot Conjugates", *Methods in Cell Biol.*, 2004, pp. 171-183, vol. 75.
Akerman, M.E. et al., "Nanocrystal Targeting In Vivo" *Proceedings of Nat'l Acad. of Sci., USA*, Oct. 1, 2002, pp. 12617-12621, vol. 99, No. 20.
Alivisatos, A.P., "Perspectives on the Physical Chemistry of Semiconductor Nanocrystals" *J. Phys. Chem.*, Mar. 26, 1996, pp. 13226-13239, vol. 100.
Zhao, M. et al., "Differential Conjugation of Tat Peptide to Superparamagnetic Nanoparticles and Its Effect on Cellular Uptake" *Bioconjugate Chemistry*, 2002, pp. 840-844, vol. 13, No. 4.
Arriagada, F.J. et al, "Synthesis of Nanosize Silica in a Nonionic Water-in-Oil Microemulsion: Effects of the Water/Surfectant Molar Ratio and Ammonia Concentration" *Journal of Colloid and Interface Science*, 1999, pp. 210-220, vol. 211.
Ballou, B. et al., "Noninvasive Imaging of Quantum Dots in Mice" *Bioconjugate Chem.*, 2004, pp. 79-86, vol. 15, No. 1.
Becker, W.G. et al., "Photoluminescence and Photoinduced Oxygen Adsorption of Colloidal Zinc Sulfide Dispersions" *J. Phys. Chem.*, 1983, pp. 4888-4893, vol. 87.

(Continued)

*Primary Examiner* — Michael G Hartley
*Assistant Examiner* — Leah Schlientz
(74) *Attorney, Agent, or Firm* — Saliwanchik, Lloyd & Eisenschenk

(57) ABSTRACT

The present invention relates to fluorescent, radio-opaque and magnetic quantum nanoparticles, useful as multifunctional contrast agents or probes for in vivo bioimaging, and methods of their use. The invention provides for multifaceted bioimaging (e.g., intra-arterial pre-operative brain mapping and broad based in vivo diagnostic imaging), including imaging of various cell types, such as stem cells.

14 Claims, 32 Drawing Sheets

OTHER PUBLICATIONS

Behboudnia, M. et al., "Systematics in the nanoparticle band gap of ZnS and $Zn_{1-x}M_xS$ (M= Mn, Fe, Ni) for various dopant concentrations" *Physical Review B*, 2001, pp. 035316:1-035316:5, vol. 63.

Bentzen, E.L. et al., "Progression of Respiratory Syncytial Virus Infection Monitored by Fluorescent Quantum Dot Probes" *Nano Letters*, 2005, pp. 591-595, vol. 5, No. 4.

Bhargava, R.N., "Doped nanocrystalline materials—Physics and applications" *Journal of Luminescence*, 1996, pp. 85-94, vol. 70.

Bhargava, R.N. et al., "Optical Properties of Manganese-Doped Nanocrystals of ZnS" *Physical Review Letters*, Jan. 17, 1997, pp. 416-419, vol. 72, No. 3.

Yang, H. et al., "Electroluminescence from Hybrid Conjugated Polymer—CdS:Mn/ZnS Core/Shell Nanocrystal Devices" *J. Phys. Chem. B.*, 2003, pp. 9705-9710, vol. 107.

Bol, A.A. et al., "Temperature dependence of the luminescence of nanocrystalline $CdS/Mn^{2+}$" *Journal of Physics and Chemistry of Solids*, 2003, pp. 247-252, vol. 64.

Bol, A.A. et al., "Luminescence Quantum Efficiency of Nanocrystalline $ZnS:Mn^{2+}$. 2. Enhancement by UV Irradiation" *J. Phys. Chem. B*, 2001, pp. 10203-10209, vol. 105.

Bol, A.A. et al., "Doped semiconductor nanoparticles—a new class of luminescent materials?" *Journal of Luminescence*, 2000, pp. 315-318, vol. 87-89.

Bol, A.A. et al., "On the Incorporation of Trivalent Rare Earth Ions in II-VI Semiconductor Nanocrystals" *Chem. Mater.*, 2002, pp. 1121-1126, vol. 14.

Bol, A.A. et al., "Luminescence Quantum Efficiency of Nanocrystalline $ZnS:Mn^{2+}$. 1. Surface Passivation and $Mn^{2+}$ Concentration" *J. Phys. Chem. B*, 2001, pp. 10197-10202, vol. 105.

Bousquet, J.C. et al., "Gd-DOTA: Characterization of a New Paramagnetic Complex[1]" *Radiology*, 1988, pp. 693-698, vol. 166.

Bruschez, M. et al., "Semiconductor Nanocrystals as Fluorescent Biological Labels" *Science*, Sep. 25, 1998, pp. 2013-2016, vol. 281.

Cao, L. et al., "Luminescence enhancement of core-shell ZnS:Mn/ZnS nanoparticles" *Appl. Phys. Letters*, Jun. 10, 2002, pp. 4300-4302, vol. 80, No. 23.

Caravan, P. et al,, "Gadolinium(III) Chelates as MRI Contrast Agents: Structure, Dynamics, and Applications" *Chem. Rev.*, 1999, pp. 2293-2352, vol. 99.

Chan, W.C.W. et al., "Luminescent quantum dots for multiplexed biological detection and imaging" *Curr. Opin. In Biotech.*, 2002, pp. 40-46, vol. 13.

Chan, W.C.W. et al., "Quantum Dot Bioconjugates for Ultrasensitive Nonisotopic Detection" *Science*, Sep. 25, 1998, pp. 2016-2018, vol. 281, No. 5385.

Dabbousi, B.O. et al., "(CdSe) ZnS Core-Shell Quantum Dots: Synthesis and Characterization of a Size Series of Highly Luminescent Nanocrystallites" *J. Phys. Chem. B*, 1997, pp. 9463-9475, vol. 101.

Derfus, A.M. et al., "Probing the Cytotoxicity of Semiconductor Quantum Dots" *Nano Letters*, 2004, pp. 11-18, vol. 4, No. 1.

Dietz, G.P.H. et al., "Delivery of bioactive molecules in the cell: the Trojan horse approach" *Mol. Cell. Neurosci.*, 2004, pp. 85-131, vol. 27.

Dubertret, B. et al., "In vivo Imaging of Quantum Dots Encapsulated in Phospholipid Micelles" *Science*, Nov. 29, 2002, pp. 1759-1762, vol. 298, No. 5599.

Gallagher, D. et al., "Doped zinc sulfide nanocrystals precipitated within a poly(ethylene oxide) matrix—processing and optical characteristics" *Journal of Crystal Growth*, 1994, pp. 970-975, vol. 138.

Gao, X. et al., "In vivo cancer targeting and imaging with semiconductor quantum dots" *Nature Biotech.*, Aug. 2004, pp. 969-976, vol. 22, No. 8.

Gao, X. et al., "Molecular profiling of single cells and tissue specimens with quantum dots" *Trends in Biotech.*, Sep. 2003, pp. 371-373, vol. 21, No. 9.

Gaponik, N. et al., "Labeling of Biocompatible Polymer Microcapsules with Near-Infrared Emitting Nanocrystals" *Nano Letters*, 2003, pp. 369-372, vol. 3, No. 3.

Gerion, D. et al., "Synthesis and Properties of Biocompatible Water-Soluble Silica-Coated CdSe/ZnS Semiconductor Quantum Dots" *J. Phys. Chem. B*, 2001, pp. 8861-8871, vol. 105.

Gupta, S. et at., "Phosphor efficiency and deposition temperature in ZnS:Mn A.C. thin film electroluminescence display devices" *Thin Solid Films*, 1997, pp. 33-37, vol. 299.

Hines, M.A. et al., "Synthesis and Characterization of Strongly Luminescing ZnS-Capped CdSe Nanocrystals" *J. Phys. Chem.* 1996, pp. 468-471, vol. 100.

Hoshina, T. et al., "Luminescence Excitation Spectra and Their Exciton Structures of ZnS Phosphors. II. Al and Te Doped Phosphors" *Jpn. J. Appl. Phys.*, 1980, pp. 279-287, vol. 19, abstract.

Huber, M.M. et al., "Fluorescently Detectable Magnetic Resonance Imaging Agents *Bioconjugate Chem.*, 1998, pp. 242-249, vol. 9.

Ihara, M. et al., "Preparation and Characterization of Rare Earth Activators Doped Nanocrystal Phosphors" *J. of the Electrochem. Soc.*, 2000, pp. 2355-2357, vol. 147, No. 6.

Jaiswal, J.K. et al., "Long-Term Multiple Color Imaging of Live Cells Using Quantum Dot Bioconjugates" *Nature Biotech.*, Jan. 2003, pp. 47-51, vol. 21.

Jaiswal, J.K. et al., "Potentials and pitfalls of fluorescent quantum dots for biological imaging" *TRENDS in Cell Bio.*, Sep. 2004, pp. 497-504, vol. 14, No. 9.

Jaszczyn-Kopec, P. et al., "Excitonic Excitation Spectra in ZnS: CI Crystal Under Pressure" *Journal of Luminescence*, 1983, pp. 319-326, vol. 28.

Jiang, W. et al., "Semiconductor quantum dots as contrast agents for whole animal imaging" *TRENDS in Biotech.*, Dec. 2004, pp. 607-609, vol. 22, No. 12.

Jin, C. et al., "Luminescence of $Mn^{2+}$ doped ZnS nanocrystallites" *J. of Luminescence*, 1996, pp. 315-318, vol. 66-67.

Josephson, L. et al., "Near-Infrared Fluorescent Nanoparticles as Combined MR/Optical Imaging Probes" *Bioconjugate Chem.*, 2002, pp. 554-560, vol. 13.

Josephson, L. et al., "High-Efficiency Intracellular Magnetic Labeling with Novel Superparamagnetic-Tat Peptide Conjugates" *Bioconjugate Chem.*, 1999, pp. 186-191, vol. 10.

Kane, R.S. et al., "Synthesis of Doped ZnS Nanoclusters within Block Copolymer Nanoreactors" *Chem. Mater.*, 1999, pp. 90-93, vol. 11.

Kim, S. et al., "Near-Infrared Fluorescent Type II Quantum Dots for Sentinel Lymph Node Mapping" *Nature Biotech.*, Jan. 2004, pp. 93-97, vol. 22, No. 1.

Kircher, M.F. et al., "A Multimodal Nanoparticle for Preoperative Magnetic Resonance Imaging and Intraoperative Optical Brain Tumor Delineation" *Cancer Research*, Dec. 1, 2003, pp. 8122-8125, vol. 63.

Kubo, T. et al., "Enhancement of photoluminescence of ZnS:Mn nanocrystals modified by surfactants with phosphate or carboxyl groups via a reverse micelle method" *Journal of Luminescence*, 2002, pp. 39-45, vol. 99.

Larson, D.R. et al., "Water-Soluble Quantum Dots for Multiphoton Fluorescence Imaging in Vivo" *Science*, May 30, 2003, pp. 1434-1436, vol. 300.

Lewis, J.S. et al., "Control of point defects and space charge in electroluminescent ZnS:Mn thin films" *J. of Appl. Physics*, Dec. 1, 2002, pp. 6646-6657, vol. 92, No. 11.

Margerstadt, M. et al., "Gd(DOTA): an alternative to Gd(DTPA) as a T1,2 relaxation agent for NMR imaging or spectroscopy" *Magn. Reson. Med.*, 1986, pp. 808-812, vol. 3, No. 5, abstract.

Smith, D.H. et at., "New Magnetic Resonance Imaging Techniques for the Evaluation of Traumatic Brain Injury" *Journal of Neurotrauma*, 1995, pp. 573-577, vol. 573, vol. 12.

Michalet, X. et al., "Quantum Dots for Live Cells, in Vivo Imaging, and Diagnostics" *Science*, Jan. 28, 2005, pp. 538-544, vol. 307.

Morawski, A.M. et al., "Targeted Nanoparticles for Quantitative Imaging of Sparse Molecular Epitopes With MRI" *Magnetic Resonance in Medicine*, 2004, pp. 480-486, vol. 51.

Schrier, J. et al., "Simple model for magnetization ratios in doped nanocrystals" *J. Appl. Physics*, 2004, pp. 1436-1438, vol. 95, No. 3.

Parungo, C.P. et al., "Intraoperative identification of esophageal sentinel lymph nodes with near-infrared fluorescence imaging" *J. Thorac. Cardiovasc. Surg.*, Apr. 2005, pp. 844-850, vol. 129, No. 4.

Peng, X. et al, "Epitaxial Growth of Highly Luminescent CdSe/CdS Core/Shell Nanocrystals with Photostability and Electronic Accessibility" *J. Am. Chem. Soc.*, 1997, pp. 7019-7029, vol. 119.

Pingbo, X. et al., "Photoluminescence Properties of Surface-Modified Nanocrystalline ZnS: Mn" *Journal of Colloid and Interface Science*, 2000, pp. 534-539, vol. 229.

Runge, V.M. et al., "MR Imaging of Rat Brain Glioma: Gd-DTPA versus Gd-DOTA[1]" *Radiology*, 1988, pp. 835-838, vol. 166.

Santra, S. et al., "TAT conjugated, FITC doped silica nanoparticles for bioimaging applications" *Chem. Commun.*, 2004, pp. 2810-2811.

Santra, S. et al., "Conjugation of Biomolecules with Luminophore-Doped Silica Nanoparticles for Photostable Biomarkers" *Anal. Chem.*, 2001, pp. 4988-4993, vol. 73.

Santra, S. et al., "Development of novel dye-doped silica nanoparticles for biomarker application" *J. of Biomedical Optics*, Apr. 2001, pp. 160-166, vol. 6, No. 2, abstract.

Santra, S. et al., "Synthesis and Characterization of Silica-Coated Iron Oxide Nanoparticles in Microemulsion: The Effect of Nanionic Surfactants" *Langmuir*, 2001, pp. 2900-2906, vol. 17.

Schaller, R.D. et al., "Tunable Near-Infrared Optical Gain and Amplified Spontaneous Emission Using PbSe Nanocrystals" *J. Phys. Chem. B*, 2003, pp. 13765-13768, vol. 107.

Schmechel, R. et al, "Photoluminescence Properties of Nanocrystalline $Y_2O_3$: $Eu^{3+}$ in Different Environments" *Scripta mater.*, 2001, pp. 1213-1217, vol. 44.

Schmidt, T. et al., "Activation of 1.54 μm $Er^{3+}$ Fluorescence in Concentrated II-VI Semiconductor Cluster Environments" *Chem. Mater.*, 1998, pp. 65-71, vol. 10.

Schroedter, A. et al., "Ligand Design and Bioconjugation of Colloidal Gold Nanoparticles" *Angew. Chem. Int. Ed.*, 2002, pp. 3218-3221, vol. 41, No. 17.

Sharma, P. et al., "Nanoparticles for bioimaging" *Advances in Colloid and Interface Science*, 2006, pp. 471-485, vol. 123-126.

Smith, A.M. et al., "Quantum Dot Nanocrystals for In Vivo Molecular and Cellular Imaging" *Photochemistry and Photobiology*, 2004, pp. 377-385, vol. 80.

Smith, A.M. et al., "Luminescence decay kinetics of $Mn^{2+}$ -doped ZnS nanoclusters grown in reverse micelles" *Phys. Rev. B*, 2000, pp. 2021-2028, vol. 62, No. 3.

Song, K.K. et al., "Highly luminescent (ZnSe)ZnS core-shell quantum dots for blue to UV emission: synthesis and characterization" *Curr. Applied Physics*, 2001, pp. 169-173, vol. 1.

Stavis, S.M. et al., "Single molecule studies of quantum dot conjugates in a submicrometer fluidic channel" *Lab on a Chip*, 2005, pp. 337-343, vol. 5.

Sun, L. et al., "Study of the optical properties of $Eu^{3+}$ -doped ZnS nanocrystals" *Journal of Alloys and Compounds*, 1998, pp. 234-237, vol. 275-277.

Suyver, J.F. et al., "Synthesis and Photoluminescence of Nanocrystalline ZnS:$Mn^{2+}$" *Nano Letters*, 2001, pp. 429-433, vol. 1, No. 8.

Suyver, J.F. et al., "Luminescence of nanocrystalline ZnSe: $Mn^{2+}$" *Phys. Chem. Chem. Phys.*, 2000, pp. 5445-5448, vol. 2.

Tanaka, M., "Photoluminescence Properties of $Mn^{2+}$—doped II-VI Semiconductor Nanocrystals" *Journal of Luminescence*, 2002, pp. 163-173, vol. 100.

Van De Rijke, F. et al., "Up-converting phosphor reporters for nucleic acid microarrays" *Nature Biotechnol.*, Mar. 2001, pp. 273-276, vol. 19.

Voura, E.B. et al., "Tracking metastatic tumor cell extravasation with quantum dot nanocrystals and fluorescence emission-scanning microscopy" *Nature Med.*, Sep. 2004, pp. 993-998, vol. 10, No. 9.

Wager, J.F. et al., "Luminescent impurity doping trends in alternating-current thin-film electroluminescent phosphors" *J. of Luminescence*, 2002, pp. 68-81, vol. 97.

Wang, Y, et al., "Nanometer-Sized Semiconductor Clusters: Materials Synthesis, Quantum Size Effects, and Photophysical Properties" *J. Phys. Chem.*, 1991, pp. 525-532, vol. 95.

Wu, X. et al., "Immunofluorescent labeling of cancer marker Her2 and other cellular targets with semiconductor quantum dots" *Nature Biotech.*, Jan. 2003, pp. 41-46, vol. 21.

Yang, H. et al., "Syntheses and applications of Mn-doped II-VI semiconductor nanocrystals" *J. Nanosci. Nanotechnol.*, Sep. 2005, pp. 1364-1375, vol. 5, No. 9, abstract.

Yang, H. et al., "Photoluminescent and electroluminescent properties of Mn-doped ZnS nanocrystals" *J. of Appl. Phys.*, Jan. 1, 2003, pp. 586-592, vol. 93, No. 1.

Yang, H. et al., "Enhanced photoluminescence from CdS:Mn/ZnS core/shell quantum dots" *Appl. Phys. Lett.*, Mar. 24, 2003, pp. 1965-1967, vol. 82, No. 12.

Yang, H. et al., "Efficient and Photostable ZnS-Passivated CdS:Mn Luminescent Nanocrystals" *Advanced Functional Materials*, Feb. 2004, pp. 152-156, vol. 14, No. 2.

Yang, H. et al., "Water-Soluble Silica-Overcoated CdS: Mn/ZnS Semiconductor Quantum Dots" *J. Chem. Physics*, Oct. 15, 2004, pp. 7412-7426, vol. 121, No. 15.

Zhelev, Z. et al., "Fabrication of quantum dot-lectin conjugates as novel fluorescent probes for microscopic and flow cytometric identification of leukemia cells from normal lymphocytes" *Chem. Commun.*, 2005, pp. 1980-1982.

Zijlmans, H.J.M.A.A. et al., "Detection of Cell and Tissue Surface Antigens Using Up-Converting Phosphors: A New Reporter Technology" *Analytical Biochemistry*, 1999, pp. 30-36, vol. 267.

Dahan, M. et al., "Diffusion Dynamics of Glycine Receptors Revealed by Single-Quantum Dot Tracking" *Science*, 2003, pp. 442-445, vol. 302, No. 5644.

Nam, J.M. et al., "Nanoparticle-Based Bio-Bar Codes for the Ultrasensitive Detection of Proteins" *Science*, 2003, pp. 1884-1886, vol. 301, No. 5641.

"Quantum Dots Could Guide Surgeons" *NIBIB eAdvances*, Feb. 11, 2004, Retrieved Mar. 3, 2004, from http://www.nbib.nih.gov/eAdvances/021104.htm.

Schwarze, S.R. et al., "In Vivo Protein Transduction: Delivery of a Biologically Active Protein in the Mouse" *Science*, 1999, pp. 1569-1572, vol. 285, No. 5433.

Aguayo, J.B. et al., "Nuclear magnetic resonance imaging of a single cell" *Nature*, 1986, pp. 190-191, vol. 322.

Alivisatos, A. P., "Less Is More in Medicine" *Scientific American*, Sep. 2001, pp. 66-73, vol. 285.

Astriab-Fisher, A. et al., "Conjugates of Antisense Oligonucleotides with the Tat and Antennapedia Cell-Penetrating Peptides: Effects on Cellular Uptake, Binding to Target Sequences, and Biologic Actions" *Pharm. Res.*, Jun. 2002, pp. 744-754, vol. 19, No. 6.

Ben-Ari, E.T., "Nanoscale Quantum Dots Hold Promise for Cancer Applications" *JNCI Journal of the National Cancer Institute*, 2003, pp. 502-504, vol. 95, No. 7.

Brigger, I. et al., "Nanoparticles in cancer therapy and diagnosis" *Adv Drug Deliv Rev*, 2002, pp. 631-651, vol. 54.

Costouros, N.G. et al., "Molecular Imaging of Tumor Angiogenesis" *Journal of Cellular Biochemistry*, 2002, pp. 72-78, vol. 39 Supplement.

Douglas, S.J. et al., "Nanoparticles in Drug Delivery" *Critical Reviews in Therapeutic Drug Carrier Systems*, 1987, pp. 233-261, vol. 3, No. 3, abstract.

Dzik-Jurasz, A., "The development and application of functional nuclear magnetic resonance to in vivo therapeutic anticancer research" *The British Journal of Radiology*, 2004, pp. 296-307, vol. 77.

Emerich, D.F. et al., "Nanotechnology and Medicine" *Expert Opinion on Biological Therapy*, 2003, pp. 655-663, vol. 3, No. 4, abstract.

Fawell, S. et al., "Tat-mediated delivery of heterologous proteins into cells" *Proc. Natl. Acad. Sci. USA*, Jan. 1994, pp. 664-668, vol. 91.

Fujisawa, T. et al., "Spontaneous Emission Spectrum in Double Quantum Dot Devices" *Science*, Oct. 30, 1998, pp. 932-935, vol. 282.

Hellgren, I. et al., "Factors Controlling the Efficiency of Tat-mediated Plasmid DNA Transfer" *Journal of Drug Targeting*, 2004, pp. 39-47, vol. 12, No. 1.

Hildebrandt, I.J. et al., "Molecular imaging applications for immunology" *Clinical Immunology*, 2004, pp. 210-224, vol. 111.

Holm, B.A. et al., "Nanotechnology in Biomedical Applications" *Molecular Crystals and Liquid Crystals*, 2002, pp. 589-598, vol. 374.

Kale, A. et al., "Infrared emission from zinc sulfide: Rare-earth doped thin films" *J. Appl. Physics*, Sep. 2003, pp. 3147-3152, vol. 94, No. 5.

Karar, N. et al., "Structure and photoluminescence studies on Zns:Mn nanoparticles" *J. Appl. Physics*, Jan. 2004, pp. 656-660, vol. 95, No. 2.

Kreel, L., "Medical imaging" *Postgraduate Medical Journal*, 1991, pp. 334-346, vol. 67.

Invitrogen, "Qdot® Conjugates Protocol Handbook" Quantum Dot Invitrogen nanocrystal technologies, Dec. 12, 2005.

Langer, S.G. et al., "Imagine Acquisition: Ultrasound, Computed Tomography, and Magnetic Resonance Imaging" *World Journal of Surgery*, 2001, pp. 1428, vol. 25.

Panyam, J. et al., "Fluorescence and electron microscopy probes for cellular and tissue uptake of poly(D,L-lactide-co-glycolide) nanoparticles" *International Journal of Pharmaceutics*, 2003, pp. 1-11, vol. 262.

Santra, S. "Integrated fluorescent, radio-opaque and magnetic nanoparticles for intra-arterial pre-operative brain mapping and broad based diagnostic imaging" abstract presented at Florida Research Consortium 2004 Technology Transfer Conference, May 17-18, 2004, St. Petersburg, FL.

Santra, S. "Multimodal quantum dots for non invasive diagnosis and real time gross visualization of brain tumors" presented at Florida Research Consortium-Tech Transfer Conference, May 18-19, 2005, Orlando, FL.

Santra, S. et al. "Development of TAT (a cell penetrating peptide) conjugated fluorescent nanoparticles for preoperative intra-arterial brain mapping" abstract presented at American Association of Neurological Surgeons 2004 Annual Meeting, May 4, 2004, Orlando, FL.

Santra, S. "Multifunctional nanoparticles for in vivo bioimaging applications" Jul. 2, 2004.

Santra, S. et al., "Synthesis and Characterization of Fluorescent, Radio-Opaque, and Paramagnetic Silica Nanoparticles for Multimodal Bioimaging Applications", *Advanced Materials*, 2005, pp. 2165-2169, vol. 17.

Santra, S. et al., "Rapid and effective labeling of brain tissue using TAT-conjugated CdS:Mn/ZnS quantum dots" *Chem. Commun.*, 2005, pp. 3144-3146.

Santra, S. et al., "Synthesis of Water-Dispersible Fluorescent, Radio-Opaque, and Paramagnetic CdS:MnZnS Quantum Dots: A Multifunctional Probe for Bioimaging" *J. Am. Chem. Soc.*, 2005, pp. 1656-1657, vol. 127.

\* cited by examiner

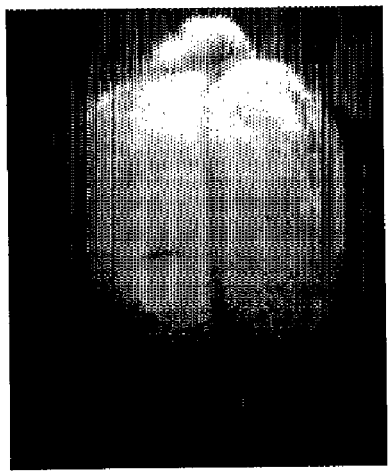
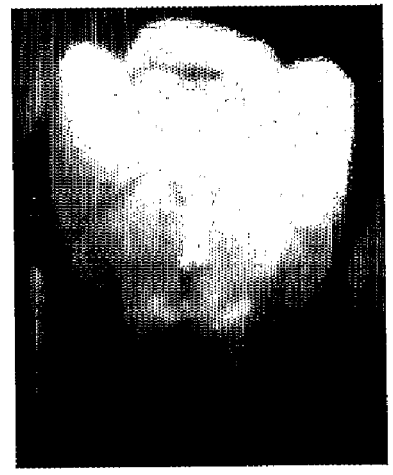
FIG. 14A　　　　　　　　FIG. 14B
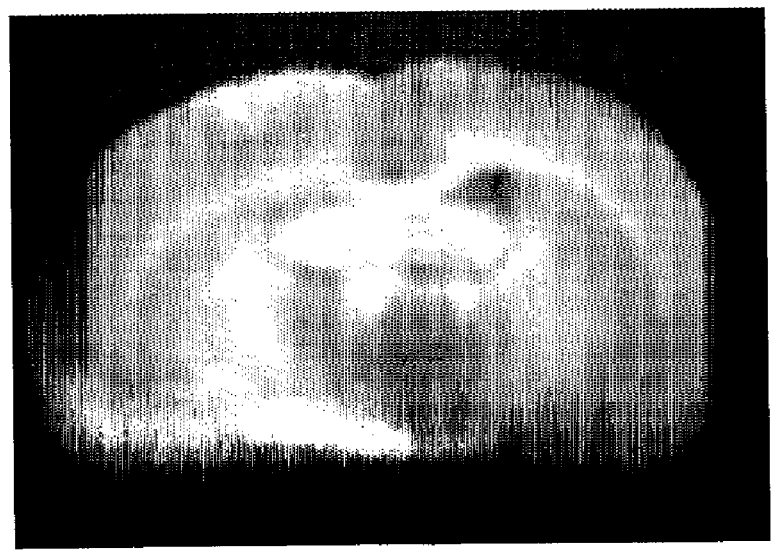
FIG. 14C

Fluorescent dye (Rubpy) doped silica core
Paramagnetic (gadolinium (III) ion bound) inner silica shell for MRI
Primary amine (-NH$_2$) functionalized outer silica shell for bioconjugation

$T_1$ Weighted

$T_2$ Weighted

NANOPARTICLES AND THEIR USE FOR MULTIFUNCTIONAL BIOIMAGING

CROSS-REFERENCE TO RELATED APPLICATIONS

This application is the National Stage of International Application Number PCT/US2005/015266, filed May 2, 2005, which claims benefit of U.S. Provisional Application Ser. No. 60/567,330, filed Apr. 30, 2004, each of which is hereby incorporated by reference herein in its entirety, including any figures, tables, nucleic acid sequences, amino acid sequences, and drawings.

GOVERNMENT SUPPORT

This invention was made with government support under Grant No. DAAD19-01-1-0603 awarded by the Army Research Office. The government has certain rights in the invention.

BACKGROUND OF THE INVENTION

The human body is composed of tissues that are generally opaque. In the past, exploratory surgery was one common way to look inside the body. Today, physicians can use a vast array of imaging methods to obtain information about a patient. Some non-invasive imaging techniques include modalities such as X-ray, magnetic resonance imaging (MRI), computer-aided tomography (CAT), ultrasound, and so on. Each of these techniques has advantages that make it useful for observing certain medical conditions and parts of the body. The use of a specific test, or a combination of tests, depends upon the patient's symptoms and the disease being diagnosed.

MRI was established as a medical diagnostic technique that offers high-resolution anatomical information about the human body, and has since been used for the detection of a multitude of diseases. MRI creates images of a body using the principles of nuclear magnetic resonance. MRI can generate thin-section images of any part of the body from any angle and/or direction, in a relatively short period of time, and without surgical invasion. MRI can also create "maps" of biochemical compounds within any cross section of the body.

MRI is possible in the human body because the body is filled with small biological magnets—the most important, for MRI purposes, being the nucleus of the hydrogen atom, also know as a proton. Once a patient is placed into a MRI unit, their body is placed in a steady magnetic field that is more than 30,000 times stronger than the Earth's magnetic field. The MRI stimulates the body with radio waves to change the steady-state orientation of the protons, causing them to align with the magnetic field in one direction or the other. The MRI then stops the radio waves and "listens" to the body's electromagnetic transmissions at a selected frequency. The transmitted signal is used to construct images of the internal body using principles similar to those developed for computerized axial tomography scanners (CAT scanners). Since the nuclear magnetic relaxation times of tissues and tumors differ, abnormalities can be visualized on the MRI-constructed image.

The continued use and development of MRI has stimulated interest in the development of contrast agents capable of altering MRI images in diagnostically useful ways. Contrast agents that are currently favored by researchers in the field are suitably complexed paramagnetic metal cations. The use of contrast agents in MRI imaging offers major opportunities for improving the value of the diagnostic information which can be obtained.

Radio contrast agents, which are used in radioisotopic imaging in a manner analogous to MRI contrast agents, are a well-developed field. The knowledge existing in this field thus provides a starting point for the development of MRI contrast agents. MRI contrast must meet certain characteristics, however, which are either not required or are considerably less critical in the case of radio contrast agents. MRI contrast agents must be used in greater quantities than radio contrast agents. As a result, they must not only produce detectable changes in proton relaxation rates but they must also be (a) substantially less toxic, thereby permitting the use of greater amounts; (b) more water soluble to permit the administration of a higher dosage in physiologically acceptable volumes of solution; and (c) more stable in vivo than their radiopharmaceutical counterparts. In vivo stability is important in preventing the release of free paramagnetic metals and free ligand in the body of the patient, and is likewise more critical due to the higher quantities used. For the same reasons, MRI contrast agents that exhibit whole body clearance within relatively short time periods are particularly desirable.

Since radio contrast agents are administered in very small dosages, there has been little need to minimize the toxicity of these agents while maximizing water solubility, in vivo stability and whole body clearance. It is not surprising therefore that few of the ligands developed for use as components in radio contrast preparations are suitable for use in preparation of MRI contrast agents. A notable exception is the well known ligand diethylene triamine pentaacetic acid (DTPA), which has proved useful in forming complexes with both radiocations, pharmacologically suitable salts of which provide useful radio contrast agents, and paramagnetic cations such as gadolinium, whose pharmacologically suitable salts have proved useful as MRI contrast agents.

The contrast agents used in MRI derive their signal-enhancing effect from the inclusion of a material exhibiting paramagnetic, ferromagnetic, or superparamagnetic behavior. These materials affect the characteristic relaxation timers of the imaging nuclei, primarily water, in the body regions into which they distribute causing an increase or decrease in magnetic resonance signal intensity. There is therefore a long felt need for an MRI imaging agent which is substantially non-toxic, highly water soluble, and highly stable in vivo and which is capable of selectively enhancing signal intensity in particular tissue types.

Optical imaging continues to gain more acceptance as a diagnostic modality since it is similar to MRI and does not expose patients to ionizing radiation. Optical imaging is based on the detection of differences in the absorption, scattering and/or fluorescence of normal and tumor tissues. One type of optical imaging comprises near-infrared fluorescent ("NIRF") imaging. Generally, in NIRF imaging, filtered light or a laser with a defined bandwidth is used as a source of excitation light. The excitation light travels through the body and when it encounters a NIRF molecule or optical imaging agent, the excitation light is absorbed. The fluorescent molecule (i.e., the optical imaging agent) then emits detectable light that is spectrally distinguishable from the excitation light (i.e., they are lights of different wavelengths). Generally, light that is detectable via NIRF imaging has a wavelength of approximately 600-1200 nm. This is important because at these wavelengths tissue autofluoresence and scattering is minimal, allowing for deep tissue imaging not capable at other wavelengths. The optical imaging agent increases the target:background ratio by several orders of magnitude, thereby enabling better visibility and distinguishability of the target area. Optical imaging agents can be designed so that they only emit detectable light upon the presence of a particular event (i.e., in the presence of a predetermined enzyme). Optical imaging, such as NIRF imaging, shows significant promise for detecting functional or metabolic changes in deep tissues, such as the overproduction of certain proteins or enzymes, in a body. This is useful because the majority of diseases induce early functional or metabolic changes in the body before anatomical changes occur. The ability to detect these metabolic changes allows for early detection, diagnosis and treatment of a disease, thereby improving the patient's chance of recovery and/or of being cured.

A contrast agent is often used in conjunction with MRI and/or optical imaging to improve and/or enhance the images obtained of a person's body. A contrast agent is a substance that is introduced into the body to change the contrast between two tissues. Generally, MRI contrast agents comprise magnetic probes that are designed to enhance a given image by affecting the proton relaxation rate of the water molecules in proximity to the MRI contrast agent. This selective change of the $T_1$ (Spin-Lattice Relaxation Time) and $T_2$ (Spin-Spin Relaxation Time) of the tissues in the vicinity of the MRI contrast agents changes the contrast of the tissues visible via MRI. Generally, optical contrast agents comprise dyes designed to emit light when excited with the correct wavelength light. This emitted light is then detected by an optical imaging device.

Contrast agents are administered to a person, typically via intravenous injection into their circulatory system, so that abnormalities in the person's vasculature, extracellular space and/or intracellular space can be visualized. Some contrast agents may stay in the person's vasculature and highlight the vasculature. Other contrast agents may penetrate the vessel walls and highlight abnormalities in the extracellular space or intracellular space through different mechanisms, like, for example, binding to receptors. After a contrast agent is injected into a tissue, the concentration of the contrast agent first increases, and then starts to decrease as the contrast agent is eliminated from the tissue. In general, a contrast enhancement is obtained in this manner because one tissue has a higher affinity or vascularity than another tissue. For example, most tumors have a greater MRI contrast agent uptake than the surrounding tissues, due to the increased vascularity and/or vessel wall permeability of the tumor, causing a shorter $T_1$ and a larger signal change via MRI.

Typical MRI contrast agents belong to one of two classes: (1) complexes of a paramagnetic metal ion, such as gadolinium (Gd); or (2) coated iron nanoparticles. As free metal ions are toxic to the body, they are typically complexed with other molecules or ions to prevent them from complexing with molecules in the body, thereby lessening their toxicity. Some typical MRI contrast agents include, but are not limited to: Gd-EDTA, Gd-DTPA, Gd-DOTA, Gd-BOPTA, Gd-DOPTA, Gd-DTPA-BMA (gadodiamide), feruimoxsil, ferumoxide and ferumoxtran.

Another class of MRI contrast agents—called "smart" contrast agents—includes contrast agents that are activated by the physiology of the body or a property of a tumor, i.e., agents that are activated by pH, temperature and/or the presence of certain enzymes or ions. Some examples of MRI smart contrast agents include, but are not limited to, contrast agents that are sensitive to the calcium concentration in a body, or those that are sensitive to pH.

"Smart" optical contrast agents have recently been used in vivo to monitor enzyme activity in tissues. These smart contrast agents only produce contrast in the presence of specific proteases. Since proteases are key factors involved in multiple disease processes, the ability to tailor contrast agents or probes to specific enzymes should ultimately allow one to detect the expression levels of marker enzymes for various pathologic conditions. This approach is capable of providing all the necessary information for studying pathologies near the surface of the skin via optical imaging. However, since low localization information is characteristic of optical imaging, one or more additional modalities may be required for diagnosing pathologies deeper within the body.

Contrast agents are often required in order to make the presence of certain diseases detectable. For example, the mechanisms of contrast in MRI (such as $T_1$, $T_2$ and/or proton density) are somewhat limited, allowing certain diseases to remain undetectable by MRI in the absence of exogenous contrast agents. This is because none of the parameters that influence contrast are affected in some diseases without the addition of a contrast agent. Therefore, using contrast agents in conjunction with MRI offers excellent sensitivity for detecting some additional pathologic conditions, thereby allowing some diseases to be detected that would otherwise be undetectable via MRI alone. For example, MRI in the presence of contrast agents has very high sensitivity for detecting breast tumors, but very low specificity for the detection of cancerous tissue. The specificity for identifying cancerous tissue is so low via MRI because multiple pathologies, such as the recruitment and production of new blood vessels (angiogenesis), are characterized by markers similar to those of cancerous tissue.

While both MRI and optical imaging provide useful information, neither independently provides all the information desired to help make early diagnoses of all diseases. As previously discussed, the majority of diseases induce early functional or metabolic changes in the body before anatomical changes occur. While these metabolic changes are almost impossible to detect via current MRI techniques, optical imaging shows significant promise in being able to detect such changes. However, when applications such as breast imaging are envisioned, optical imaging by itself is very limited by the spatial resolution that can be achieved.

Nanoparticle probes have found tremendous success in recent years as labels in biological systems and have shown great potential for bioimaging (Akerman et al., *Proc Natl Acad Sci USA* 2002, 99:12617; Santra et al., *Analytical Chemistry*, 2001, 73:4988; Santra et al., *Journal of Biomedical Optics*, 2001, 6:160; Ben-Ari et al., *Journal of the National Cancer Institute*, 2003, 95:502; Panyam et al., *International Journal of Pharmaceutics*, 2003, 262:1); diagnostic (Brigger et al., *Adv Drug Deliv Rev*, 2002, 54:631; Alivisatos, *Scientific American*, 2001, 285:66), and therapeutic purposes (Emerich et al., *Expert Opinion on Biological Therapy* 2003, 3:655; Douglas et al., *Crc Critical Reviews in Therapeutic Drug Carrier Systems*, 1987, 3:233; Holm et al., *Molecular Crystals and Liquid Crystals*, 2002,374:589).

Recently, the demand for the development of multimodal nanoparticle probes for in vivo disease diagnosis and therapy has increased significantly. Multimodal nanoparticle probes have the potential for imaging cells, tissues and other organs in multiple modes, as well as the delivery of therapeutic agents to specific targets.

Diagnostic neuroimaging techniques such as angiography, CT (computed tomography) and MRI are widely used to monitor changes in anatomy and disease diagnosis (Hildebrandt et al., *Clinical Immunology*, 2004, 111:210; Dzik-Jurasz et al., *British Journal of Radiology*, 2004:77, 296; Costouros et al., *Journal of Cellular Biochemistry*, 2002:72;

Langer et al., *World Journal of Surgery*, 2001, 25:1428; Smith et al., *Journal of Neurotrauma*, 1995, 12:573; Kreel et al., *Postgraduate Medical Journal*, 1991, 67:334). Contrast agents are often administered to patients, to help delineate pathological from healthy tissue. Contrast agents for angiography and CT scans are radio-opaque, which allow clear visualization of the contrast under an X-ray source. Iodinated chemical compounds such as iohexol (also called Omnipaque™) and iodixanol (also called Visipaque™) are routinely used as X-ray contrast agents. They consist of electron dense iodine atoms, which show contrast under an X-ray. MRI contrast agents such as Gadoteridol, (Gd-HP-DO3A, a gadolinium chelate complex, also known as Prohance™) and mangafodipir trisodium (a manganese chelate complex, also known as Teslascan™) are usually paramagnetic. Both gadolinium and manganese atoms contain unpaired electrons, which account for paramagnetic behavior and resultant MRI contrast.

Three-dimensional CT and MR imaging are routinely used for diagnosis of brain tumors, although these techniques do not allow the direct and gross visualization of tumor tissue with a bare eye. Further, these imaging techniques do not provide surgical guidance to surgeons for the tumor resection in real-time. Most of the unsuccessful brain tumor surgeries, which sometimes result in major neurological disabilities, were primarily responsible for the lack of technological advancement in demarcating tumor boundaries. It would thus be highly desirable to obtain a contrast agent that would meet all criteria of existing contrast agents and in addition to that it would provide real time guidance in a way that surgeons could clearly visualize the tumor during the surgical procedure.

A multifunctional contrast agent with optical, radio-opaque and magnetic properties could help in the preoperative diagnosis and the intraoperative surgical resection of brain tumors or other surgical lesions. The synthesis of bifunctional contrast agents for dual (fluorescence and magnetic) imaging was reported by others (Kircher et al, *Cancer Research*, 2003, 63:8122; Huber et al., *Bioconjugate Chemistry*, 1998, 9:242), in which organic fluorescent dyes were used. The use of organic dyes may not be suitable for real-time imaging as these dyes often undergo rapid photobleaching process.

The present invention relates to the use of luminescent semiconductor nanocrystals (quantum dots) as contrast agents and labels in biological systems. Quantum dots are nanometer scale particles that absorb light, then quickly re-emit the light but in a different wavelength and, thus, color. The dots have optical properties that can be readily customized by changing the size or composition of the dots. Quantum dots are available in multiple colors and brightness, offered by either fluorescent dyes or semiconductor LEDs (light emitting diodes). In addition, quantum dot particles have many unique optical properties such as the ability to tune the absorption and emission wavelength by changing the size of the dot. Thus, different-sized quantum dots emit light of different wavelengths. Quantum dots have been described in U.S. Pat. No. 6,207,392, and are commercially available from Quantum Dot Corporation.

Quantum dots are composed of a core and a shell. The core is typically composed of cadmium selenide (CdSe), cadmium telluride (CdTe), or indium arsenide (InAs). CdSe provides emission on the visible range, CdTe in the red near infrared, and InAs in the near infrared (NIR). The composition and the size of the spherical core determine the optical properties of the quantum dot. For instance, a 3 nm CdSe quantum dot produces a 520 nm emission, a 5.5 nm CdSe quantum dot produces a 630 nm emission, and intermediate sizes result in intermediate colors. The emission width is controlled by the size distribution.

The outer shell of a quantum dot protects the core, amplifies the optical properties, and insulates the core from environmental effects. It can also provide a surface coating to link the particles to molecules, such as polymers. Biomolecules such as antibodies, streptavidin, lectins, and nucleic acids can be coupled to quantum dots. Traditional light sources such as lamps, lasers, and LEDs are exemplary excitation sources for quantum dots.

Quantum dots are the subject of intensive investigation. In undoped II-VI semiconductors (e.g., CdSe, CdTe and ZnSe), the band gap is engineered by control of the crystal size that leads to tunable band-edge emission. By doping the nanocrystals with luminescent activators (Suyver et al., *Phys. Chem. Chem. Phys.*, 2000, 2:5445; Jin et al., *J. Lumin.*, 1995, 66-7:315; Behboudnia et al., *Phys. Rev. B.*, 2001, 63:03516; Sun et al., *J. Alloy Compd.*, 1998, 277:234; Schechel et al., *Scripta Mater.*, 2001, 44:1213; Bol et al., *J. Phys. Chem. Solids*, 2003, 64:247), the excitation can be tuned by quantum size effects, even though the activator-related emission energy is largely unchanged. When a dopant with quantum states remote from the valence and conduction band edges is added to the semiconductor host, another radiative mechanism is involved. This mechanism results in localized (atomic transition) luminescence, not band edge recombination, since the luminescence emission processes are confined to the localized luminescence center.

Doped nanocrystalline II-VI semiconductors incorporating rare earth (RE) ions such as $Tb^{3+}$, $Eu^{3+}$, and $Er^{3+}$ have been reported (Kane et al., *Chem. Mater.*, 1999, 11:90; Ihara et al., *J. Electrochem. Soc.*, 2000, 147:2355; Sun et al., *J. Alloy Compd.*, 1998, 277:234; Schmidt et al., *Chem. Mater.*, 1998, 10:65). However, due to the dissimilar chemical properties (e.g., ionic radius, valence state) between the RE ion and host cation ($Cd^{2+}$, $Zn^{2+}$), efficient doping of RE ions into II-VI semiconductor host is not favorable (Bol et al., *Chem. Mater.*, 2002, 14:1121). Even though some $4f^n$-$4f^n$ transition-related emissions have been observed in RE ion-doped nanocrystalline II-VI semiconductors, it was speculated that their characteristic emissions originate from RE ions adsorbed on the particle surface. In contrast to RE ions, the chemical properties of $Mn^{2+}$ are very similar to those of $Cd^{2+}$ (or $Zn^{2+}$), thus incorporating $Mn^{2+}$ into II-VI semiconductor host much easier.

The $Mn^{2+}$ ion, used in many luminescent materials, has a $d^5$ configuration. The $Mn^{2+}$ ion exhibits a broad emission peak, whose position depends strongly on the host lattice to changes in crystal field strength with host. The emission color can vary from green to deep red, corresponding to a $^4T_1$-$^6A_1$ transition (Blasse et al., *Luminescent Materials*, Springer-Verlag, Berlin, 1994). Since this transition is not spin-allowed, the typical luminescent relaxation time of this emission is of the order of milliseconds (Blasse et al., 1994; Bol et al., *J. Lumin.*, 2000, 87-9:315; Smith et al., *Phys. Rev. B*, 2000, 62:2021). Bulk ZnS:Mn has been widely used as a phosphor (Gallagher et al., *J. Cryst. Growth*, 1994, 138:970), particularly in alternating current thin film electroluminescence (ACTFEL) devices (Lewis et al., *J. Appl. Phys.*, 2002, 92:6646; Wager et al., *J. Lumin.*, 2002, 97:68; Gupta et al., *Thin Solid Films*, 1997, 299:33). $Mn^{2+}$ d-electron states act as efficient luminescent centers while interacting strongly with s-p electronic states of the ZnS host into which external electronic excitation is normally directed. The subsequent transfer of electron and hole pairs into the electronic level of the $Mn^{2+}$ ion leads to the characteristic yellow emission from the $Mn^{2+}$ $^4T_1$-$^6A_1$ transition (Gallagher et al., 1994). Possible mechanisms for excitation of the $Mn^{2+}$ in semiconductor hosts (ZnS, CdS) have been suggested. In one mechanism a hole trapped by the $Mn^{2+}$ ion is recombined with an electron, leading to $Mn^{2+}$ in an excited state (Hoshina et al., *Jpn. J. Appl. Phys.*, 1980, 19:279; Jaszczynkopec et al., *J. Lumin.*, 1983, 28:319). Another suggested mechanism is recombination of a bound exciton at the $Mn^{2+}$ site, which again promotes the $Mn^{2+}$ to an excited state (Suyver et al., *Nano. Lett.,* 2001, 1:429).

Although the optical properties of doped semiconductor (Mn-doped ZnS) nanocrystallines were published in 1983 (Becker et al., *J. Phys. Chem.*, 1983, 87:4888), it was not until the publication by Bhargava's group that a considerable effort on doped semiconductor nanocrystals was made. Since Bhargava et al. reported in 1994 that Mn-doped ZnS nanocrystals exhibited dramatic lifetime shortening as well as high quantum yield (Bhargava et al., *Phys. Rev. Lett.*, 1994, 72:416), doped semiconductor nanocrystals have been regarded as a new class of luminescent materials with a wide range of applications, e.g., in displays, sensors, and lasers (Bhargava, *J. Lumin.*, 1996, 70:85).

Since a large portion of the atoms in nanocrystals is located on or near the surface, the surface properties should have significant effects on their structural and optical properties (Alivisatos, *J. Phys. Chem.*, 1996, 100:13226). Organically passivated nanocrystals still have a relatively large number of unpassivated surface sites due to the limited interaction of organic passivating species with either anionic or cationic sites, resulting in partial coverage of the nanocrystal surface (Wang et al., *J. Phys. Chem.*, 1991, 95:525). These unpassivated surface sites act as nonradiative recombination and photodegradable sites, and thus suppress the efficient luminescence and allow photodegradation of the material and devices (Peng et al., *J. Am. Chem. Soc.*, 1997, 119:7019; Hines et al., *J. Phys. Chem.*, 1996, 100:468). Control of the surface has been a critical issue to obtain highly luminescent, photostable nanocrystals. Inorganically passivated (or core/shell structured) nanocrystals such as CdSe/CdS, CdSe/ZnS, and ZnSe/ZnS have been reported to be an improvement over those passivated by organic surface layers (Peng et al., *J. Am. Chem. Soc.*, 1997, 119:7019; Hines et al., *J. Phys. Chem.*, 1996, 100:468; Lee et al., *Curr. Appl. Phys.*, 2001, 1:169). Using inorganic materials with a wider band gap, surface-related defect states could be effectively passivated, leading to enhanced photostability as well as improved quantum efficiency.

Recently, quantum dots have been actively studied as electroluminescent (EL) components and luminescent biomarkers. Quantum dots have a tremendous potential in labeling biological entities such as cells, tissues and biohazard particles (bacteria, viruses), as evident from reports from the fields of molecular/cell biology, medical diagnostics and targeted therapeutics (Chan et al., *Curr. Opin. Biotechnol*, 2002, 13:40; Chan et al., *Science*, 1998, 281:2016; Bruchez et al., *Science*, 1998, 281:2013; Wu et al., *Nat. Biotechnol.*, 2003, 21:41; Larson et al., *Science*, 2003, 300:1434; Dubertret et al., *Science*, 2002, 298:1759). The hot solution phase chemistry-derived core/shell structured Qdots, where surface passivating layers such as CdS and ZnS are epitaxially grown on the CdSe core, have been found to dramatically enhance the quantum yields of CdSe Qdots from <10% up to 40-50% (Peng et al., *J. Am. Chem. Soc.*, 1997, 119:7019; Hines et al., *J. Phys. Chem.*, 1996, 100:468; Dabbousi et al., *J. Phys. Chem. B*, 1997, 101:9463). Advanced properties such as higher quantum efficiency and improved photostability in the luminescent semiconductor Qdots open a promising possibility for the development of a new class of luminescent biomarkers. In addition, luminescent Qdots (inorganic fluorophores) have advantages over conventional organic fluorophores, since Qdots have large absorption bands, narrow spectral emission bands, and are photochemically stable. However, luminescent Qdots synthesized by hot solution phase chemistry have a poor solubility in water, resulting in a poor compatibility with biological environments and aqueous assay conditions (Chan et al., *Science*, 1998, 281:2016; Bruchez et al., *Science*, 1998, 281:2013; Wu et al., *Nat. Biotechnol.*, 2003, 21:41; Larson et al., *Science*, 2003, 300:1434; Dubertret et al., *Science*, 2002, 298:1759; Gerion et al., *J. Phys. Chem. B*, 2001, 105:8861).

Due to their hydrophobic surface property, an appropriate surface coating is necessary to disperse Qdots in aqueous solution. Coating also protects them from photo-initiated surface degradation, which is directly related to fading of fluorescence intensity and toxicity. Despite recently reported toxic effects of quantum dots (Derfus et al., *Nano Lett.*, 2004, 4:11-18), both in vitro and in vivo studies have been reported in favor of using Qdots for biolabeling applications, including in vivo disease diagnosis (Bruchez et al., *Science*, 1998, 281: 2013-2016; Chan et al., *Curr. Opin. Biotechnol.*, 2002, 13:40-46; Nie et al., *Cytometry*, 2002, 25:25; Gao et al., *Nat. Biotechnol.*, 2004, 22:969-976).

In the visible range, because of the limitation of low signal penetration capability of Qdot fluorescence through living tissue, other types of optical probes, e.g., NIR (near infra-red) dyes, NIR Qdots, and up-converting phosphors have attracted attention recently (Josephson et al., *Bioconjugate Chem.*, 2002, 13:554-560; Schaller et al., *J. Phys. Chem. B.*, 2003, 107:13765-13768; Gaponik et al., *Nano Lett.*, 2003, 3:369-372; van de Rijke et al., *Nat. Biotechnol.*, 2001, 19:273-276; Zijlamns et al., *Anal. Biochem.*, 1999, 267:30-36). It is expected that by using these probes, a signal from a few millimeter deep tissue (such as skin cancers) could be detected non-invasively. These NIR probes, however, will not be suitable for the detection of brain tumors. It is unlikely that an optical signal will pass through the skull, severely limiting any brain related application of these optical probes.

For in vivo bio-labeling applications, it is desired to incorporate additional properties such as radio-opacity and paramagnetism in the same probe (multifunctional probe). This will allow non-invasive tumor diagnosis using CT (Computer Tomography) scan and/or MRI (Magnetic Resonance Imaging) scan before performing the surgery. Multifunctional probes with both fluorescence and paramagnetic properties have been reported recently in the literature (Kircher et al., *Cancer Res.*, 2003, 63:8122-8125). These probes were synthesized by incorporating fluorescent and magnetic components separately into a biodegradable polymer matrix. In these cases, organic dyes were used as fluorescent component, which may not be stable in an in vivo environment (Santra et al., *Chem. Commun.*, 2004, 2810-2811).

There is a need for nanoparticle systems and methods that can be used to further aid in the early detection of disease. There is also a need for systems and methods that allow for high-resolution localization of biochemical activity in a living organism. There is also a need for bifunctional or multifunctional contrast agents that can be utilized in two or more different modalities concurrently or consecutively. There is yet a further need for multifunctional contrast agents that can be utilized in both MRI and optical imaging concurrently.

BRIEF SUMMARY OF THE INVENTION

The present invention relates to multifunctional contrast agents or probes, and methods of using the same. The invention provides fluorescent, radio-opaque and magnetic quantum nanoparticles (NP) for multifaceted bioimaging (e.g., intra-arterial pre-operative brain mapping and broad based in vivo diagnostic imaging).

The present invention provides contrast agents and methods that allow high-resolution in vivo imaging of the localization of biochemical activity in a living organism, and are particularly useful in the early detection of disease. Embodiments of the present invention may comprise multifunctional contrast agents that can be utilized in two or more different imaging modalities concurrently or consecutively.

In one aspect, the invention provides a multi-functional contrast agent comprising a luminescent semiconductor nanocrystal (quantum dot). The quantum dot comprises a cadmium sulfide (CdS):manganese (Mn) core and a zinc sulfide (ZnS) shell (referred to herein as a CdS:Mn/ZnS core/shell quantum dot). It should be understood that the core and shell of the quantum dot may each contain additional active or inert components. Preferably, the quantum dot is within the range of approximately 3 nm and 100 nm. Optionally, the quantum comprises one or more targeting moieties, such as a TAT peptide or folic acid.

In a preferred embodiment, the multifunctional contrast agent is a yellow-emitting monodisperse, ultra-small (e.g., less than 10 nm), water-soluble CdS:Mn/ZnS nanoparticle (zinc sulfide capped and manganese doped cadmium sulfide quantum dot). Furthermore, the contrast agent is preferably coated with a systemically non-toxic material, such as amorphous silica. The nanoparticles of the present invention (also referred to herein interchangeably as NP, particles, quantum dots, Qdots, QD, probes, nanocrystals, core/shell nanocrystals, detection agents, and/or contrast agents) are superior to conventional fluorescent dyes because of their remarkable photostability, brightness, and suitability for in vivo multifaceted bioimaging.

In some embodiments, the quantum dots further comprise a coating (outer shell), which can passivate the Cds:Mn/ZnS portions of the nanoparticle, improve brightness and, if necessary, reduce leakage of toxic cadmium ions. Preferably, the coating comprises silica. The coating can be amine-functionalized to the ZnS shell, for example (an amine-functionalized silica coating). The size of the quantum dot will vary with the thickness of the coating.

In some embodiments, the quantum dots include a gadolinium (Gd) (III)/$SiO_2$ coating (outer shell) or a dysprosium (Dys)/$SiO_2$ coating (outer shell). In one embodiment, the quantum dot is an "activatable contrast agent" that includes a Gd (III)/$SiO_2$ coating (outer shell) and a carbohydrate, wherein the carbohydrate molecule attaches to Gd and blocks the ninth coordination site of Gd in the absence of a carbohydrate-degrading enzyme but renders the coordination site accessible to intracellular water in the presence of the carbohydrate-degrading enzyme. In this way, when the ninth coordination site of Gd is blocked by the carbohydrate, the coordination site is blocked from water exchange (such as exchange with intracellular water), which makes the particle magnetically "dark". In the presence of a carbohydrate-degrading enzyme, the carbohydrate is degraded by the enzyme, freeing (unblocking) the coordination site for water exchange, resulting in the particle becoming magnetically "bright". Other Gd coordination site blocking agents and corresponding agents for degrading or removing the blocking agent may be utilized. In another embodiment, the quantum dot includes a Dys/$SiO_2$ coating (outer shell), wherein contrast increases with the strength of the magnetic field used.

In another embodiment, the contrast agent comprises a particle, such as a silica particle, wherein each particle comprises a plurality of quantum dots of the invention, which permits greater control of quantum dot loading and particle size. In one embodiment, CdS:Mn/ZnS quantum dots are post-coded with Gd/$SiO_2$. Each particle can be, for example, 30 nm to 500 nm in diameter. As with the quantum dots of the invention, the particles can be included in a composition, such as an injectable formulation, for administration to a subject.

In another embodiment, the quantum dot is part of a ligand (a chelating silane compound) having the capability to simultaneously attach to (capture) (1) a silica particle, (2) a Gd ion, and (3) a blocking agent, such as galactose or other carbohydrate. As described above, the carbohydrate will attach to the Gd ion, blocking the ninth coordination site for water exchange, and make the ligand magnetically dark. Once the carbohydrate is degraded or otherwise removed, the ligand becomes magnetically bright.

In some embodiments, the multifunctional contrast agent of the present invention may be utilized concurrently in MRI and at least one other bioimaging modality, such as fluorescence imaging or CT scan (e.g., angiography), simultaneously or consecutively in any order.

In another embodiment, the present invention provides multifunctional contrast agents that are designed to allow simultaneous or consecutive visualization and imaging of a target area using multiple modalities (e.g., MRI and CT scan) so as to allow both anatomical and functional (e.g., metabolic) information to be obtained contemporaneously. The anatomical information can be obtained via MRI imaging, and the functional/metabolic information is obtained via another modality, in conjunction with the administration of a multifunctional contrast agent of the invention.

The multifunctional contrast agents of the present invention allow enhanced anatomical information to be obtained. As used herein, the term "enhanced" means that the image or information obtained by using the multifunctional contrast agent is of improved quality over the image or information that would be obtained by using no contrast agent. The enhanced anatomical information may be obtained via computed tomography, positron emission tomography, or magnetic resonance imaging, for example. The enhanced functional information may be obtained via near-infrared fluorescence imaging, for example.

In another aspect, the invention provides a method for visualizing a target, such as a cell(s), tissue(s), or other entity, within an opaque medium, such as biological tissue in vitro or in vivo. In some embodiments, the method involves obtaining in vivo imaging of biochemical activity in a body, comprising the steps of administering a multifunctional contrast agent of the present invention to a subject; obtaining an image of anatomical information of the subject; and/or obtaining an image of functional/metabolic information of the subject. Preferably, the subject is a living subject. These images may be obtained concurrently or consecutively in any order. In one embodiment, the multifunctional contrast agent is administered intravenously, but it may also be administered in any other suitable manner such as orally or intramuscularly. In some embodiments, the image of anatomical information may be obtained via computed tomography, positron emission tomography, or magnetic resonance imaging. In other embodiments, the image of functional information may be obtained via optical imaging. Optionally, the method can further comprise recording the image in a tangible or computer readable (e.g., electronic) medium, and/or diagnosing the subject based on the image obtained.

BRIEF DESCRIPTION OF THE DRAWINGS

FIG. 10A shows a micrograph of a cross section (rostral) of rat brain (10× magnification). FIG. 10B shows a fluorescence micrograph of the same cross section shown in FIG. 10A.

FIGS. 14A-C show gross views of a rat brain labeled with TAT-conjugated Qdots; FIGS. 14A and 14B represent dorsal views and 14C represents coronal section. Pink color (left side in FIGS. 14A and 14C and right side in FIG. 14B) originates primarily from Qdot fluorescence and background blue color (right side in FIGS. 14A and 14C and left side in FIG. 14B) is due to the combination of UV excitation, autofluorescence, and scattering lights. No filters were used for gross visualization of rat brain.

FIG. 15B clearly shows that TAT conjugated Qdots extensively labeled blood capillaries, crossed BBB and reached brain parenchyma.

FIG. 18B clearly showed that there was minimal autofluorescence from the brain tissue.

(FIG. 21C) fluorescence excitation (recorded at 600 nm emission) and emission spectra (recorded at 450 nm excitation) of Rubpy:Gd (III)/$SiO_2$ nanoparticles.

FIG. 27A shows both loaded and unloaded cells (control) under white light. FIGS. 27B and 27C shows fluorescence and MR images of nanoparticle loaded cells, respectively. Bright spots were due to the formation of cell clusters.

DETAILED DISCLOSURE OF THE INVENTION

Figure 1:
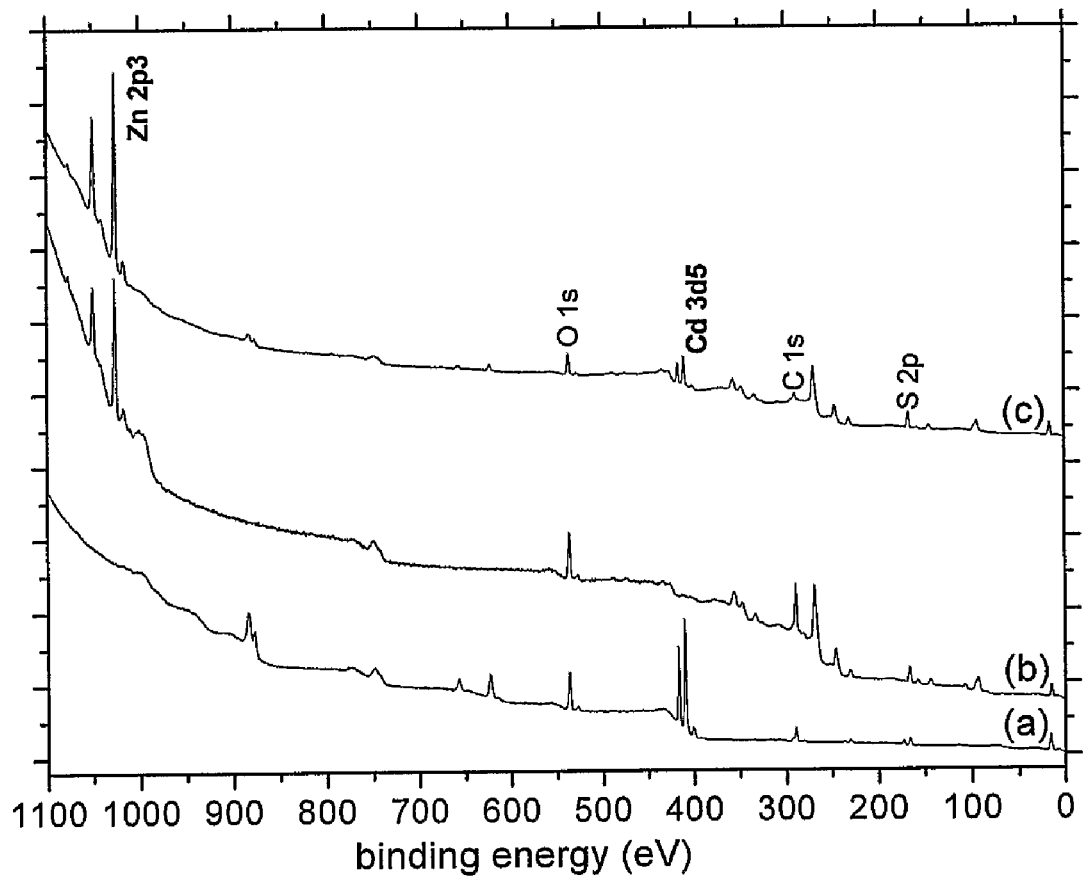
FIG. 1 shows XPS survey scans of (a) CdS:Mn, (b) ZnS:Mn, and (c) CdS:Mn/ZnS core/shell nanocrystals.

The present invention provides multifunctional detection agents that, by virtue of their fluorescent, radio-opaque, and paramagnetic properties, function as contrast agents using one or more imaging modalities. These multifunctional detection agents aid in the detection of physiological changes associated with biochemical changes in the tissue, which may indicate tissue abnormality, cardiovascular disease, thrombosis, cancer, etc. Use of the multifunctional detection agents of the invention allow precise, direct, real-time visualization of normal and abnormal anatomical features.

In one aspect, the invention provides a multi-functional contrast agent comprising a luminescent semiconductor nanocrystal (quantum dot). The quantum dot comprises a cadmium sulfide (CdS):manganese (Mn) core and a zinc sulfide (ZnS) shell (referred to herein as a CdS:Mn/ZnS core/shell quantum dot). It should be understood that the core and shell of the quantum dot may each contain additional active or inert components. Preferably, the quantum dot is within the range of approximately 3 nm and 100 nm. Optionally, the quantum comprises one or more targeting moieties, such as a TAT peptide or folic acid.

In a preferred embodiment, the multifunctional contrast agent is a yellow-emitting monodisperse, ultra-small (e.g., less than 10 nm), water-soluble CdS:Mn/ZnS nanoparticle (zinc sulfide capped and manganese doped cadmium sulfide quantum dot). Furthermore, the contrast agent is preferably coated with a systemically non-toxic material, such as amorphous silica. The nanoparticles of the present invention (also referred to herein interchangeably as NP, particles, quantum dots, Qdots, QD, probes, nanocrystals, core/shell nanocrystals, detection agents, and/or contrast agents) are superior to conventional fluorescent dyes because of their remarkable photostability, brightness, and suitability for in vivo multifaceted bioimaging.

In some embodiments, the quantum dots further comprise a coating (outer shell), which can passivate the Cds:Mn/ZnS portions of the nanoparticle, improve brightness and, if necessary, reduce leakage of toxic cadmium ions. Preferably, the coating comprises silica. The coating can be amine-functionalized to the ZnS shell, for example (an amine-functionalized silica coating). The size of the quantum dot will vary with the thickness of the coating.

In some embodiments, the quantum dots include a gadolinium (Gd) (III)/$SiO_2$ coating (outer shell) or a dysprosium (Dys)/$SiO_2$ coating (outer shell). In one embodiment, the quantum dot is an "activatable contrast agent" that includes a Gd (III)/$SiO_2$ coating (outer shell) and a carbohydrate, wherein the carbohydrate molecule attaches to Gd and blocks the ninth coordination site of Gd in the absence of a carbohydrate-degrading enzyme but renders the coordination site accessible to intracellular water in the presence of the carbohydrate-degrading enzyme. In this way, when the ninth coordination site of Gd is blocked by the carbohydrate, the coordination site is blocked from water exchange (such as exchange with intracellular water), which makes the particle magnetically "dark". In the presence of a carbohydrate-degrading enzyme, the carbohydrate is degraded by the enzyme, freeing (unblocking) the coordination site for water exchange, resulting in the particle becoming magnetically "bright". The carbohydrate molecule can be attached by convention bio-conjugate techniques (Hermanson, Greg T., *Bioconjugate Techniques*, Academic Press, N.Y., 1996). Other Gd coordination site blocking agents and corresponding agents for degrading or removing the blocking agent may be utilized. In another embodiment, the quantum dot includes a Dys/$SiO_2$ coating (outer shell), wherein contrast increases with the strength of the magnetic field used.

In another embodiment, the contrast agent comprises a particle, such as a silica particle, wherein each particle comprises a plurality of quantum dots of the invention, which permits greater control of loading and size. Each particle can be, for example, 30 nm to 500 nm in diameter. As with the quantum dots of the invention, the particles can be included in a composition, such as an injectable formulation, for administration to a subject.

In another embodiment, the quantum dot is part of a ligand (a chelating silane compound) having the capability to simultaneously attach to (capture) (1) a silica particle, (2) a Gd ion, and (3) a blocking agent, such as galactose or other carbohydrate. As described above, the carbohydrate will attach to the Gd ion, blocking the ninth coordination site for water exchange, and make the ligand magnetically dark. Once the carbohydrate is degraded or otherwise removed, the ligand becomes magnetically bright.

In some embodiments, the multifunctional contrast agent of the present invention may be utilized concurrently in MRI and at least one other bioimaging modality, such as fluorescence imaging or CT scan (e.g., angiography), simultaneously or consecutively in any order.

In another embodiment, the present invention provides multifunctional contrast agents that are designed to allow simultaneous or consecutive visualization and imaging of a target area using multiple modalities (e.g., MRI and CT scan) so as to allow both anatomical and functional (e.g., metabolic) information to be obtained contemporaneously. The anatomical information can be obtained via MRI imaging, and the functional/metabolic information is obtained via another modality, in conjunction with the administration of a multifunctional contrast agent of the invention.

The multifunctional contrast agents of the present invention allow enhanced anatomical information to be obtained. As used herein, the term "enhanced" means that the image or information obtained by using the multifunctional contrast agent is of improved quality over the image or information that would be obtained by using no contrast agent. The enhanced anatomical information may be obtained via computed tomography, positron emission tomography, or magnetic resonance imaging, for example. The enhanced functional information may be obtained via near-infrared fluorescence imaging, for example.

In another aspect, the invention provides a method for visualizing a target, such as a cell(s), tissue(s), or other entity, within an opaque medium, such as biological tissue in vitro or in vivo. In some embodiments, the method involves obtaining in vivo imaging of biochemical activity in a body, comprising the steps of administering a multifunctional contrast agent of the present invention to a subject; obtaining an image of anatomical information of the subject; and/or obtaining an image of functional/metabolic information of the subject. Preferably, the subject is a living subject. These images may be obtained concurrently or consecutively in any order. In one embodiment, the multifunctional contrast agent is administered intravenously, but it may also be administered in any other suitable manner such as orally or intramuscularly. In some embodiments, the image of anatomical information may be obtained via computed tomography, positron emission tomography, or magnetic resonance imaging. In other embodiments, the image of functional information may be obtained via optical imaging. Optionally, the method can further comprise recording the image in a tangible or computer readable (e.g., electronic) medium, and/or diagnosing the subject based on the image obtained.

In a preferred embodiment, the multifunctional detection agent (contrast agent) is a yellow-emitting monodisperse, ultra-small (less than 10 nm), water-soluble CdS:Mn/ZnS nanoparticle (zinc sulfide capped and manganese doped cadmium sulfide quantum dot; also referred to herein as Qdot or QD). The photoluminescent and electroluminescent properties of the Qdot have been described by Yang H. and P. Holloway (Yang H. and P. Holloway, *Journal of Applied Physics*, 2003, 93(1):586-592; Yang H. and P. Holloway, *Applied Physics Letters*, 2003, 82(12):1965-1967), are incorporated herein by reference in their entirety. The contrast agents of the invention can also be used to image non-biological opaque mediums.

The contrast agents of the present invention exhibit fluorescent, radio-opaque, and paramagnetic properties, allowing imaging by photoluminescence, fluoroscopy, and MRI, all using the same semiconductor crystalline material. The contrast agents of the present invention are superior to conventional fluorescent dyes because of their remarkable photostability, brightness, and suitability for in vivo multifaceted bioimaging (e.g., fluorescence, CT scan/angiography, MR imaging/angiography). Thus, advantageously, the multifunctional contrast agents of the present invention can function as both MRI contrast agents and optical contrast agents. As used herein, the term "MRI contrast agent" or "magnetic resonance contrast agent" means a molecule that can be used to enhance an MRI image. As used herein, the terms "optically detectable agent" and "optical contrast agent" mean a photoluminescent compound (i.e., a compound that will emit detectable energy after excitation with light).

The contrast agent of the invention is preferably water soluble. The particles can be made or rendered water soluble using various techniques, such as surface modification. For example, the contrast agent can be coated with a systemically non-toxic material, such as amorphous silica. However, other strategies to water-solubilize quantum dots with a hydrophobic surface can be utilized. For example, mercaptoacetic acid can be used as a coupling reagent with ZnS capped CdSe (CdSe/ZnS) quantum dots (Chan, W. C. W., and Nie, S. M. *Science* 1998, 281:2016). Other methods that may be utilized include encapsulation of individual quantum dots with an amphiphilic polymer (Wu, X. Y. et al., *Nat. Biotechnol.* 2003, 21:41; Larson, D. R.; Zipfel, W. R.; Williams, R. M.; Clark, S. W. et al., *Science* 2003, 300:1434), micelle-forming hydrophilic polymer-grafted lipids (Dubertret, B. et al., *Science* 2002, 298:1759), or biodegradable polymers such as polylactic acid (PLA), polyglycolic acid (PGA), PLGA (PLA-co-PGA), dextran, and alginate.

Disclosed herein is a single-step synthesis protocol for producing novel, highly water-dispersible, multifunctional, 3.1 nm size CdS:Mn/ZnS core-shell Qdots using water-in-oil (W/O) microemulsion method. These Qdots are fluorescent, radio-opaque, paramagnetic and suitable for attaching biomolecules such as DNA, proteins, peptides, antibodies, etc., and are extremely stable in an in vivo environment (fluorescent dyes were stable with silica encapsulation in dye-doped silica nanoparticles (Santra et al., *Chem. Commun.*, 2004, 2810-2811); similar silica coating can be provided to Qdots to obtain in vivo stability). The present inventors engineered these Qdots for in vitro and (particularly) for in vivo applications considering a few important imaging aspects: (i) endovascular administration of Qdot formulation could be monitored under fluoroscopic guidance using X-ray; (ii) after the administration of Qdot formulation, CT scan and/or MRI scan will allow pre-operative diagnosis of the labeled target; and (iii) for certain applications (such as tumor resection), Qdot fluorescence would allow real-time visualization of labeled target tissue (such as tumors).

The Qdots were initially synthesized following Yang et al.'s synthesis protocol (Yang et al., *Appl. Phys. Lett.*, 2003, 82:1965-1967). In order to make Qdots suitable for bioconjugation, a further modification was made to obtain primary amine groups on the Qdot surface (Schroedter et al., *Angew. Che., Int. Ed.*, 2002, 41:3218-3221). The hydrolysis and co-condensation reaction of tetraethyl orthosilicate (TEOS), 3-(aminopropyl) triethoxysilane (APTS) and 3-(Trihydroxysilyl) propyl methylphosphonate (THPMP) produced a highly water-dispersible silica layer around each Qdot. Pure silica coated Qdots are water-dispersible. At neutral pH, the zeta potential ($\xi$) of silica coated Qdots is about −42 mV. The negative potential is due to the presence of deprotonated silanol groups (Si—O$^-$) on the Qdot surface (pKa=7.0). Upon amine modification with APTS, $\xi$ value drops close to the isoelectric point ($\xi$~0.5). This is due to the protonation of primary amine groups (pKa=9.0) resulting in severe particle aggregation. The addition of THPMP (pKa=2.0), recovers the Qdot aqueous dispersibility by increasing $\xi$ value to about −36 mV.

Multifunctional properties of Qdots were characterized by fluorescence, radio-opacity and magnetic measurements. Bright yellow emission is clearly observed by using a 366 nm multiband hand-held UV (ultra-violet) light source. The fluorescence excitation band is broad. For minimizing tissue damage it is possible to generate a desired amount of emission photons by exciting Qdots in the longer wavelength range (e.g., 400 nm) rather than 366 nm. Pure silica nanoparticles (approximately 10 nm, control) were found to be nonfluorescent at 366-nm excitation. For radio-opacity (X-ray contrast) measurement, a Qdot sample was placed under a fluoroscope that uses X-ray excitation. In order to compare radio-opacity, the Qdot sample was compared with a conventional radio-opaque material (Omnipaque™, also called iohexol, a contrast agent for CT scan and angiography) at the same concentration. Based on fluoroscopy images of Qdots and Omnipaque of equal concentration and the same magnification and X-ray power, it was estimated that the X-ray absorption of Qdots is less than that of Omnipaque, which provides a sufficient contrast for current practice. The present inventors expect that similar contrast will also be seen under a CT scan. Using a SQUID (Superconducting Quantum Interference Device) magnetometer, the present inventors have performed magnetic measurement of Qdots. At room temperature, Qdots showed paramagnetic property with a typical hysterisis curve for paramagnetic material at room temperature. The paramagnetic property of Qdots can be utilized to obtain contrast in MRI scan in an in vivo setup.

Qdot fluorescence has been well explained previously (Yang et al., *Appl. Phys. Lett.*, 2003, 82:1965-1967; Yang et al., *Adv. Funct. Mater.*, 2004, 14:152-156). The bright yellow fluorescence is a result of an efficient surface passivation by the epitaxially matched ZnS crystalline layer around the CdS:Mn crystalline core. Radio-opacity of the Qdot is due to the presence of the electron dense cadmium atoms, which interact with the X-ray beam. Manganese ions (Mn$^{2+}$) present in Qdots are paramagnetic and responsible for the magnetic property.

To demonstrate in vivo bioimaging capability, amine modified Qdots were conjugated to TAT peptide (a cell penetrating peptide) by modifying Josephson et al.'s protocol (Josephson et al., *Bioconjugate Chem.*, 1999, 10:186-191). TAT conjugated Qdots in PBS (phosphate buffer saline, pH 7.4) were then administered through the right common carotid artery (CCA) that supplies blood only to the right part of the brain of a rat. After completing the procedure, the whole brain was then sliced into four pieces and sent for histological analysis. Transmission and fluorescence images of a cross section of the rat brain confirmed labeling of branches of the right MCA (Middle Cerebral Artery, a distal branch of the internal carotid artery) in the brain and confirmed the efficacy of the labeling protocol. No labeling occurred on the left brain hemisphere (control experiment). In this study, the present inventors aimed to selectively label brain blood vessels using an endovascular approach. It is well understood that the Blood-Brain-Barrier (BBB, a tight junction of endothelial cells) protects the brain from toxic substances that are present in the blood circulation. The TAT peptide can penetrate the blood-brain-barrier without disruption. Using a TAT-mediated delivery system, it is thus possible to deliver diagnostic and therapeutic agents to the brain without compromising the BBB. From this in vivo experiment, it was clearly seen that TAT conjugated Qdots stained brain parenchyma and blood vessels with higher concentration at the vessel wall.

In addition to the luminescent property, for in vivo biolabeling applications, it is desired to incorporate additional properties such as radio-opacity and paramagnetism in the same agent, thereby producing a "multifunctional" agent. This is because this multifunctional agent will allow noninvasive and real-time tracking diagnosis using CT (computer tomography) scan and/or MRI (magnetic resonance imaging) scan before performing the surgery. Due to the presence of manganese ($Mn^{2+}$), CdS:Mn/ZnS Qdots have been demonstrated by the inventors to exhibit paramagnetic property at room temperature using a SQUID (Superconducting Quantum Interference Device) magnetometer. However, the magnetic response of these Qdots was still lacking to generate magnetic resonance (MR) contrast due to the small quantity of $Mn^{2+}$ ions. From this viewpoint, it is desirable that yellow luminescent CdS:Mn/ZnS Qdots be further engineered to possess an enhanced magnetic property and thus MR contrast. In addition, to make the particulars useful for deep tissue imaging, fluorophores with absorption and emission in the near infrared region should be used. One approach would be the incorporation of gadolinium ($Gd^{3+}$) ions onto the NIR-Qdots, with the presence of $Gd^{3+}$ ions renders Qdots MRI active.

As described in Examples 1-6, a Qdot surface was functionalized using tetraethyl orthosilicate (TEOS), 3-(aminopropyl) triethoxysilane (APTS) and 3-(trihydroxysilyl) propyl methylphosphonate (THPMP). These functionalized Qdots were highly water-soluble and suitable for subsequent biomolecule conjugation due to the presence of negative charge ($—PCH_3OOO^-$) groups and primary amine ($—NH_2$) groups, respectively. These Qdots were further functionalized by successive addition of n-(trimethoxysilylpropyl)ethyldiamine, triacetic acid trisodium salt (TSPETE) and Gd acetate. TSPETE is known to have reactive coordination sites for capturing $Gd^{3+}$ ions efficiently. Example 7 describes water-in-oil (W/O) microemulsion synthesis and characterization of 100 nm (±10 nm) size tris(2,2'-bipyridyl) dichlororuthenium (II) hexahydrate (Rubpy) and gadolinium ($Gd^{3+}$) doped novel silica (Rubpy:Gd (III)/$SiO_2$) nanoparticles. These nanoparticles were fluorescent, radio-opaque and paramagnetic as characterized by fluorescence, fluoroscopic (X-ray) and magnetic measurements, respectively. To enable bioconjugation, nanoparticle surface was modified to attach primary amine groups. To verify MRI contrast, nanoparticles were compared with a commercially available paramagnetic MRI contrast agent, Prohance® and it was found that nanoparticles showed better MRI contrast. From ICP (Inductively Coupled Plasma) analysis, it was estimated that each nanoparticle carried about 16,000 $Gd^{3+}$ ions. The better MRI contrast from nanoparticles is most likely due to the presence of substantially large amount of $Gd^{3+}$ ions. Since nanoparticles are fluorescent, radio-opaque and paramagnetic, they have great potential for multimodal bioimaging (imaging at multiple modes) applications.

Figure 24:
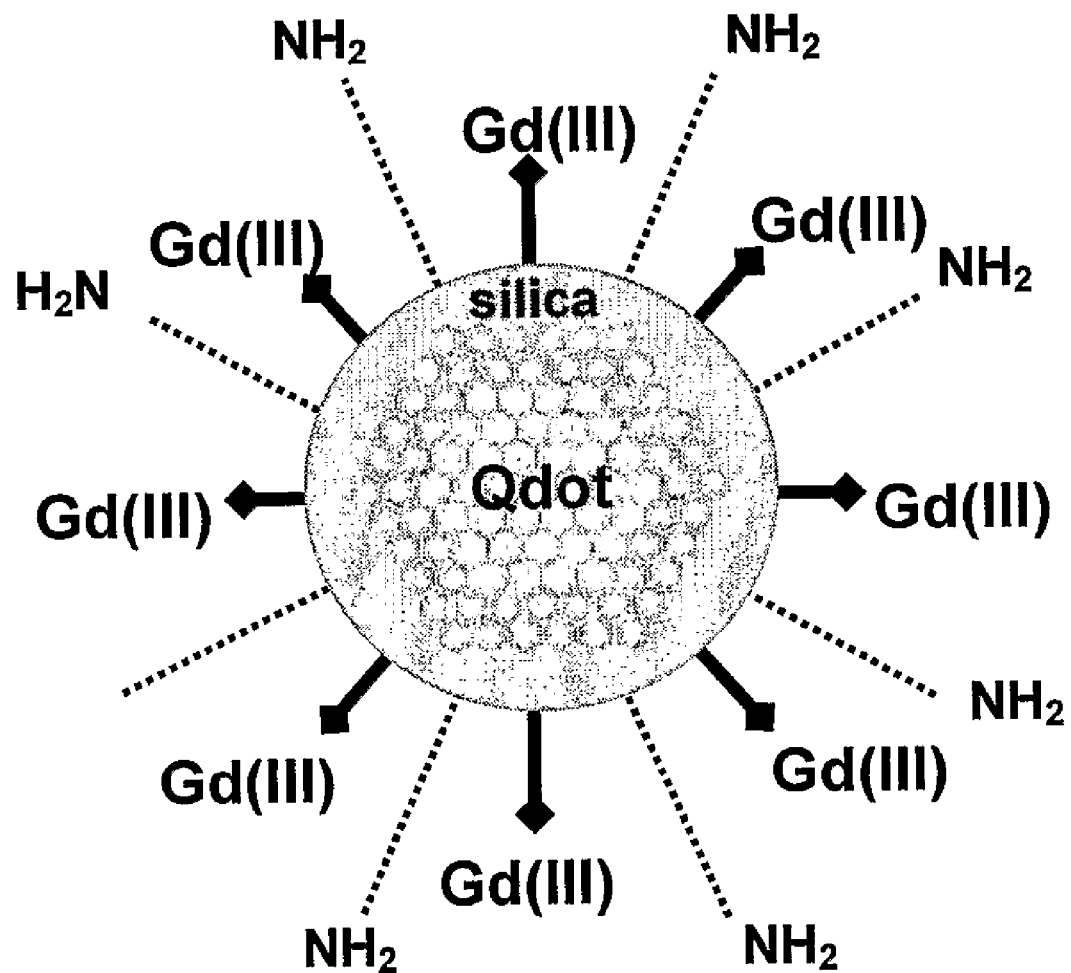
FIG. 24 shows a Gd-functionalized Qdot as enhanced magnetic resonance (MR) contrast agent.

FIG. 24 shows the representative schematic of Gd-functionalized Qdots as enhanced magnetic resonance (MR) agents (Examples 7-9). In addition, the present inventors have determined that these particles can be specifically targeted to the folate receptor on tumor cells that over-expressed folate receptors resulting in both optical and T1 based MRI contrast, opening up the possibility that this particle could be used to directly image cancer cell formation noninvasively using MRI.

Figure 25:
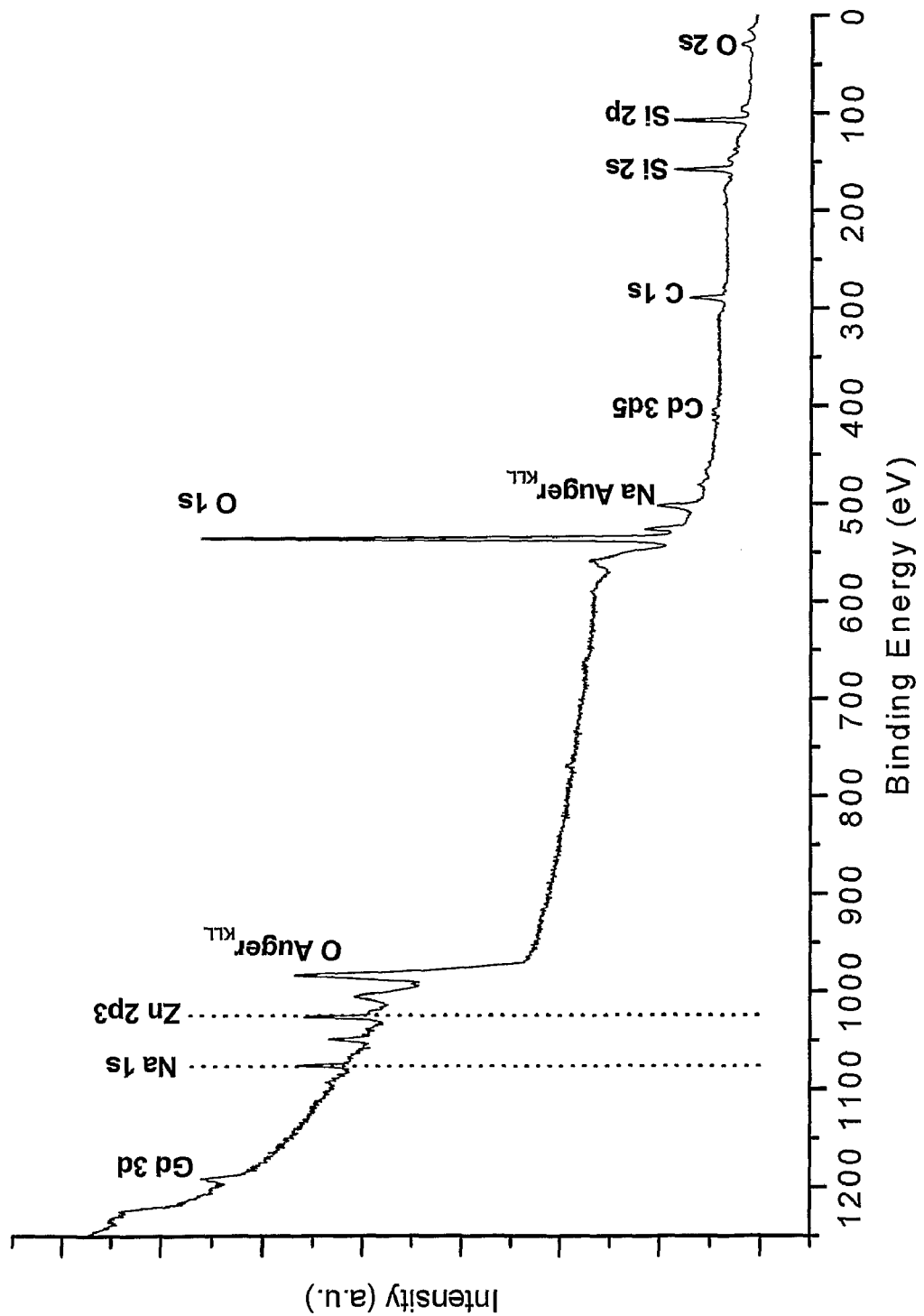
FIG. 25 shows XPS survey scan spectrum of Gd-functionalized, silica-overcoated CDS:Mn/Zns Qdots.
Figures 26A, 26B:
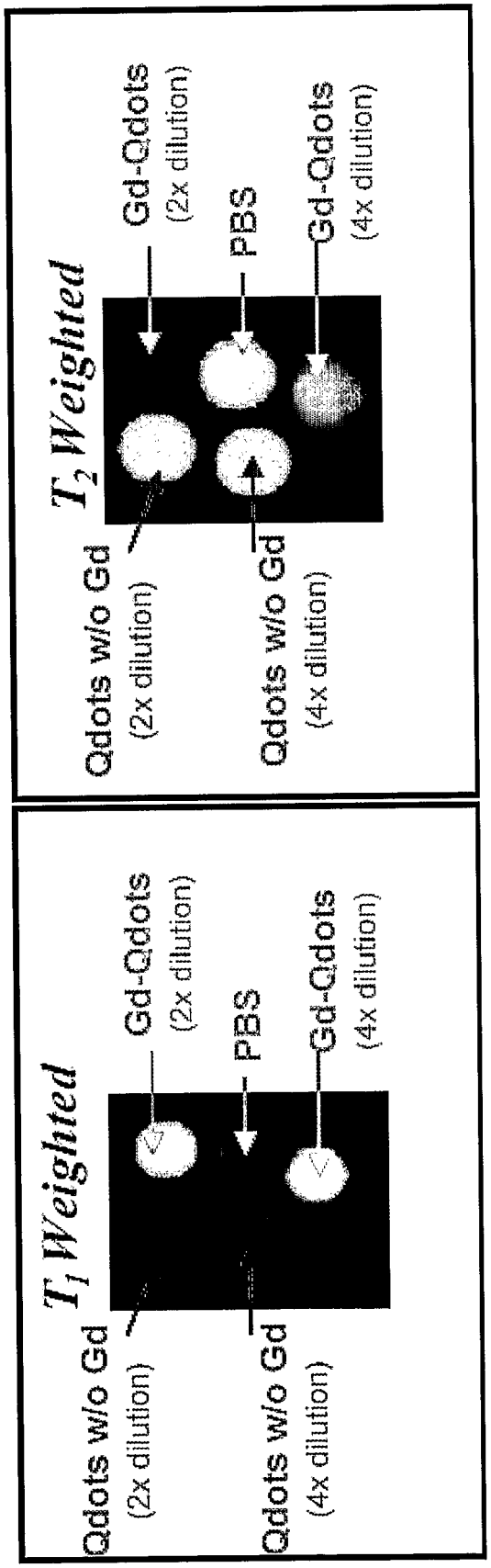
FIGS. 26A and 26B show a comparison of magnetic resonance (MR) contrast images of Qdots without and with Gd. Gd-functionalized Qdots generated MR contrast on both T1 (FIG. 26A) and T2 (FIG. 26B) weighted sequences. An MR image of PBS is shown for comparison.

X-ray photoelectron spectroscopy (XPS) survey scan of Gd-functionalized, silica-overcoated CdS:Mn/ZnS Qdots is shown in FIG. 25, demonstrating that the Gd atoms are present in Qdots. The Gd 3d peak at ~1191 eV is apparent, consistent with the fact that TSPETE is efficient as a $Gd^{3+}$ capturing agent. FIG. 26 shows MR contrast images of Qdots without and with Gd on both $T_1$ (longitudinal relaxation time) and $T_2$ (transverse relaxation time) weighted sequences. MR contrast images of differently diluted Qdot solutions and phosphate buffer saline (PBS) are also compared. Note that 2× and 4× diluted Qdot solutions correspond to approximately ~8 and ~4 mg/ml of Qdots in PBS, respectively. The MR contrast images of Qdots without Gd, without respect to their concentration, are not distinguishable from that of PBS on both $T_1$ and $T_2$ weighted sequences. However, Gd-functionalized Qdots exhibit the dependence of the MR contrast on their concentration and inverse MR signal compared to that of PBS on both $T_1$ and $T_2$ weighted sequences. These MR studies clearly show that $Gd^{3+}$ ions, which are bound to Qdots, can result in image contrast on both $T_1$ and $T_2$ weighted image modes, demonstrating the ability of these Gd-functionalized Qdots to function as strong $T_1$ and $T_2$ contrast agents. Moreover, the present inventors have optimized the surface charge on these particles so that they can be used to label cells in vitro using standard DNA transfection protocols. This has allowed the present inventors to perform extensive labeling with the multifunctional nanoprobe of both murine and human stem cells in vitro. Importantly, labeled stem cells can generate both T1 and T2 contrast on MRI scans. This allows for the noninvasive monitoring of stem cell migration and tracking for transplantation studies. By placing the Gd ion on the outside of the particle, MRI T1 contrast is generated by the exchange between bulk water inside the cell and the Gd ion. Due to the placement of the SFA groups in close proximity to the Gd this probe can be made activate able by altering the accessibility of water to the Gd ion using enzyme activation strategies.

In another aspect, the present invention provides compositions comprising the multifunctional agents of the present invention in admixture with at least one pharmaceutically acceptable carrier, as diagnostic agents and/or therapeutic agents. For instance, these active ingredients are useful for the manufacture of medicaments suitable for imaging or imaging-aided applications, including MRI, nuclear scintigraphy (NS), MRI-aided applications or NS-aided applications or for the manufacture of imaging agents or imaging-aided agents for use in such applications. This includes their use as in vivo effective contrast agents, including multipurpose contrast agents, for visualizing and/or identifying organs, parts of organs or systems such as for example the vasculatory system, the hepatobiliary system or the renal-urinary system, tissues such as for example necrotic tissue, and for visualizing and/or identifying diseases and pathologies.

Diseases that may be visualized and/or identified using the multifunctional contrast agents of the invention include, but are not limited to, ischemic insults such as myocardial or cerebral infarction and space-occupying lesions (e.g., tumors or inflammatory lesions) in solid organs such as the liver, kidney, spleen, adrenal gland, etc. These agents are also useful in the follow-up of a therapy, for instance the evolution of necrosis. In particular, these contrast agents are useful in medical applications involving necrosis and necrosis-related pathologies, such as pathological or therapeutic necrosis caused by pathologic or therapeutically-induced ischemia or originating from trauma, radiation and/or chemicals, including therapeutic ablation, radiotherapy and/or chemotheraphy, myocardial and cerebral infarctions. For this purpose, they are administered to the human body, preferably enterally or parenterally, as therapeutic and/or diagnostic agents.

Using the contrast agents of the present invention, endovascular pre-operative brain mapping techniques will produce a visual contrast between eloquent (functional) and non-eloquent ("silent") brain tissue. The significance of this approach is the capability to individualize the unique brain functional map of each patient requiring brain resection to improve their neurosurgical outcome. This technique will be useful for malignant glioma resection, low-grade glioma resection, arteriovenous malformation resection, brain resection for epilepsy surgery, and other functional neurosurgical resections. It will improve upon current techniques by allowing a precise, direct, real-time visualization of non-eloquent/silent brain tissue that can be resected with absolute assurance that no neurological deficit will result. Targeting moieties may also be used selectively to direct the accumulation of the contrast agents of the present invention. For example, upon administration via microcatheter under fluoroscopic guidance, HIV TAT-grafted contrast agents of the present invention will be either internalized rapidly by the brain capillary endothelial cells (via endocytosis/pinocytosis), or will be strongly adsorbed onto cell membranes resulting in staining of that portion of the brain. The post-staining follow-up with CT-scan and/or MRI scan will confirm the NP distribution (mapping) prior to surgery.

For diagnosis purposes, nanoparticles of the invention can be grafted with folic acid as a targeting moiety, to specifically target the folate-receptor over-expressing metastatic adenocarcinoma. Alternative delivery methods include catheter-assisted administration of HIV TAT peptide grafted NP probes through tumor feeding arteries. This technique will not only allow surgeons to acquire CT/MRI scans non-invasively but also will guide them for effective resection of lesions in real time through NP fluorescence.

In conjunction with the contrast agents of the present invention, an HIV TAT-mediated endovascular brain mapping technique will be useful for malignant glioma resection, low-grade glioma resection, arteriovenous malformation resection, brain resection for epilepsy surgery, and other functional neurosurgical resections. This method will improve upon current techniques by allowing a precise, direct, real-time visualization of non-eloquent/silent brain tissue that can be resected with absolute assurance that no neurological deficit will result from the neurosurgical resection.

Many metastatic adenocarcinoma e.g., breast adenocarcinoma, lung adenocarcinoma, oral carcinoma and pituitary adenoma overexpress folate receptors. There are many clinically challenging brain tumors such as malignant gliomas that may also possibly over-express folate receptors and can be effectively targeted using the contrast agents of the present invention. For example, if substantial amounts of nanoparticles are present due to the folate receptors, the tumor will glow (emit fluorescent light) when exposed to an excitation photon source. Malignant tissue can be clearly distinguished from normal tissue in real time to delineate malignancies from effective surgery.

The multifunctional contrast agents of the present invention can be synthesized using a water-in-oil (W/O) microemulsion method. The nano-size water droplets serve as the nano-reactor. Several factors, including water-to-surfactant molar ratio, type of surfactant, and co-surfactant molecules and their ratio, reaction type and nature of active agents, can be varied to affect the size and surface functionality of the nanoparticles of the invention.

Pharmaceutically acceptable carriers for use in admixture with the contrast agents of this invention are well known in the art of pharmacy and will be selected depending on the mode of administration to the patient (i.e., the mammal, in particular humans) involved. Typically, a suitable formulation is a physiologically acceptable liquid formulation, preferably an aqueous solution or an emulsion or suspension including conventional surfactants such as polyethylene glycol.

In another aspect, the invention provides a method for visualizing a target, such as a cell(s), tissue(s), or other entity, within an opaque medium, such as biological tissue in vitro or in vivo. In some embodiments, the method involves generating an image of at least a part of the body of a subject, such as a human or non-human animal, comprising systemically or locally administering to the subject an effective amount of a contrast agent of the present invention. Preferably, the contrast agents of the invention are used systemically as diagnostic agents by parenteral administration, such as intravenous or intra-arterial injection, at low doses. Optionally, the method can further comprise recording the image in a tangible or computer readable (e.g., electronic) medium, and/or diagnosing the subject based on the image obtained.

The contrast agents of the invention are also useful for local administration, such as intramuscular administration, or intracoronary administration in the case of a subject with myocardial infarction.

The present invention also comprises methods of obtaining high-resolution, in vivo images of biochemical activity in a subject. Preferably, the subject is a living subject. One method comprises estimating the localization of the contrast agent using one modality (e.g., MRI), while concurrently estimating the level of biological activity using a second modality (e.g., optical imaging). Another method comprises obtaining an image of anatomical information of a living organism and obtaining an image of functional information of the living organism, wherein a multifunctional contrast agent of the invention is introduced within the living organism. The multifunctional contrast agents of the present invention may be administered in any suitable way, preferably via intravenous injection. Optionally, these methods can further comprise recording the image in a tangible or computer readable (e.g., electronic) medium, and/or diagnosing the subject based on the image obtained.

The multifunctional detection agents of the present invention allow both anatomical and functional information to be obtained simultaneously via at least two different modalities. Using a first modality (e.g., magnetic resonance imaging) provides high-resolution anatomical information from which the precise anatomical localization of the detection agent can be determined. Using a second modality (e.g., optical imaging) provides functional or metabolic information. This combination of anatomical and functional information allows for easier and earlier diagnosis and treatment of diseases than currently exits, thereby improving the patient's chance of recovery and/or of being cured.

While multifunctional detection agents for concurrent or consecutive use in combination with MRI/optical imaging systems have been described above, it is understood that multifunctional detection agents may be designed for concurrent or consecutive use in alternative combination imaging systems without deviating from the scope of the present invention. For example, a multifunctional detection agent for concurrent use in computed tomography (CT) and optical imaging, or for concurrent use in positron emission tomography (PET) and optical imaging, also falls within the scope of this invention. Other diagnostic imaging techniques that may be combined with optical imaging include: X-ray based techniques, ultrasound, diagnostic techniques based on radioactive materials (e.g., scintigraphy and SPECT), and the like.

The multifunctional contrast agents of the present invention can be formulated in any form, for example, a solid which is dissolved in a suitable carrier prior to use, or as a pre-made solution. When in the form of a solution, a wide range of concentrations is possible depending upon the desired dosing and method of introduction into tissue.

The carriers and adjunct ingredients which comprise the balance of the compositions of the present invention can be any pharmaceutically acceptable ingredient, for example, as a carrier distilled water. For embodiments wherein the contrast agent is provided as a solid which is reconstituted with water prior to use, the balance may comprise an inert filler. Or a suitable surfactant, anti-oxidant, or other stabilizer may be utilized.

The present invention further relates to a method for providing enhanced human and animal tissue differentiation by contrast imaging, wherein the multifunctional contrast agents of the present invention are taken up by target cells or tissue. The method of the present invention relates to establishing a blood serum level which is an effective amount of a contrast agent as described herein.

In one embodiment, the invention provides a method for providing to tissue a contrast agent of the invention thereby enabling differentiation of human or animal tissue, comprising the steps of: (a) administering to a human or non-human animal an effective amount of a multifunctional contrast agent which provides a contrast between tissues; and (b) sustaining said effective amount of contrast agent for a period of time exceeding one hour. The serum levels for effective imaging will vary depending upon the uptake by the recipient, the type of tissue that is being targeted, and the lipophilicity of the contrast agent. The multifunctional contrast agent can be administered to the human or non-human animal in the form of a composition further comprising one or more carriers and, optionally, adjunct ingredients.

Administration of the multifunctional contrast agent of the present invention to a human or non-human animal subject, on whom imaging is to be performed, can be achieved by conventional procedures known in by those of ordinary skill in the art and disclosed in the literature. Aqueous solutions of the agent are most conveniently used. The concentration of the agent in these solutions and the amounts administered may vary widely, the optimum in each case determined by the strength of the magnetic moment of the manganese atom, the contrast enhancement strength of the chelate as a whole and the method of administration, the degree of contrast enhancement desired or needed, and the age, weight, and condition of the subject to whom administration is made. Administration may be achieved by any route or method. For example, the contrast agent (and compositions comprising the contrast agent) can be administered parentally, such as by intravenous administration. One of skill in the art can readily determine appropriate dosages, concentrations, and rates and duration of administration, based on the size of the subject, the route of administration, and the imaging modality.

Imaging devices appropriate to the imaging modality can be utilized to obtain images of the desired anatomical information using the methods of the invention, and their selection can be readily determined by those skilled in the art. For example, the imaging device can be a magnetic resonance imaging device, a computed tomography device, a positron emission tomography device, or an optical imaging device, or combinations of two or more of the foregoing. If two or more imaging devices are used, they may be used simultaneously or consecutively.

In another embodiment, the multifunctional contrast agents of the invention can be associated with an implantable or deployable medical device or a pharmaceutically active agent, such as a drug, in order to detect and/or track the location of the device or pharmaceutically active agent in vivo. For example, the contrast agents can be integrated into a film, such as a polymer film, forming a composite, and coated or otherwise associated with at least a portion of the device or implant.

In a preferred embodiment, the multifunctional contrast agents of the invention include targeting moieties. As used herein, the term "targeting moiety" is intended to mean a functional group that serves to target or direct the particle to a particular location or association (e.g., a specific binding event) with a target, such as a cell, tissue, protein, or other entity. Thus, for example, a targeting moiety may be used to target a molecule to a specific target protein or enzyme, or to a particular cellular location, or to a particular cell type, to selectively enhance accumulation of the contrast agent. Suitable targeting moieties include, but are not limited to, polypeptides, nucleic acids, carbohydrates, lipids, hormones including proteinaceous and steroid hormones, growth factors, receptor ligands, antigens and antibodies, and the like. For example, as is more fully outlined below, the contrast agents of the invention may include a targeting moiety to target the agents to a specific cell type such as tumor cells, such as a transferrin moiety, since many tumor cells have significant transferrin receptors on their surfaces. Similarly, a targeting moiety may include components useful in targeting the contrast agents to a particular subcellular location. As will be appreciated by those in the art, the localization of proteins within a cell is a simple method for increasing effective concentration. For example, shuttling a drug into the nucleus confines them to a smaller space thereby increasing concentration. The physiological target may simply be localized to a specific compartment, and the agent must be localized appropriately. More than one targeting moiety can be conjugated or otherwise associated with each nanoparticle, and the target molecule for each targeting moiety can be the same or different.

Thus, suitable targeting sequences include, but are not limited to, binding sequences capable of causing binding of the moiety to a predetermined molecule or class of molecules, while retaining bioactivity of the expression product, (for example by using enzyme inhibitor or substrate sequences to target a class of relevant enzymes); sequences signaling selective degradation, of itself or co-bound proteins; and signal sequences capable of constitutively localizing the candidate expression products to a predetermined cellular locale, including (a) subcellular locations such as the Golgi, endoplasmic reticulum, nucleus, nucleoli, nuclear membrane, mitochondria, chloroplast, secretory vesicles, lysosome, and cellular membrane; and (b) extracellular locations via a secretory signal. Particularly preferred is localization to either subcellular locations.

The targeting moiety can function to target or direct the contrast agent to a particular location, cell type, diseased tissue, or association. In general, the targeting moiety is directed against a target molecule. As will be appreciated by those in the art, the contrast agents of the invention are generally injected intravenously; thus, preferred targeting moieties are those that allow concentration of the agents in a particular localization. Thus, for example, antibodies, cell surface receptor ligands and hormones, lipids, sugars and dextrans, alcohols, bile acids, fatty acids, amino acids, peptides and nucleic acids may all be attached to localize or target the contrast agent to a particular site.

In preferred embodiments, the targeting moiety allows targeting of the contrast agents of the invention to a particular tissue or the surface of a cell. That is, in a preferred embodiment, the contrast agents of the invention need not be taken up into the cytoplasm of a cell to be activated.

In some embodiments, the targeting moiety is a peptide. For example, chemotactic peptides have been used to image tissue injury and inflammation, particularly by bacterial infection; see WO 97/14443, hereby expressly incorporated by reference in its entirety.

In some embodiments, the targeting moiety is an antibody. The term "antibody" includes antibody fragments, as are known in the art, including Fab or $Fab_2$, single chain antibodies (Fv for example), chimeric antibodies, etc., either produced by the modification of whole antibodies or those synthesized de novo using recombinant DNA technologies.

In a preferred embodiment utilizing an antibody, the antibody targeting moieties used in the invention are humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody will preferably also comprise at least a portion of an immunoglobulin constant region (Fc), typically that of a human immunoglobulin (Jones et al., Nature 321:522-525 (1986); Riechmann et al., Nature 332: 323-329 (1988); and Presta, Curr. Op. Struct. Biol. 2:593-596 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, J. Mol. Biol. 227:381 (1991); Marks et al., J. Mol. Biol. 222:581 (1991)). The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol. 147(1):86-95 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology, 14:826 (1996); Lonberg and Huszar, Intern. Rev. Immunol. 13:65-93 (1995).

Bispecific antibodies are monoclonal, preferably human or humanized, antibodies that have binding specificities for at least two different antigens. In the present case, one of the binding specificities is for a first target molecule and the other one is for a second target molecule.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism (see, for example, Suresh et al., Methods in Enzymology 121:210 (1986)).

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

In a preferred embodiment, the antibody is directed against a cell-surface marker on a cancer cell; that is, the target molecule is a cell surface molecule. As is known in the art, there are a wide variety of antibodies known to be differentially expressed on tumor cells, including, but not limited to, HER2, VEGF, etc.

In addition, antibodies against physiologically relevant carbohydrates may be used, including, but not limited to, antibodies against markers for breast cancer (CA15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

In one embodiment, antibodies against virus or bacteria can be used as targeting moieties. As will be appreciated by those in the art, antibodies to any number of viruses (including orthomyxoviruses, (e.g., influenza virus), paramyxoviruses (e.g., respiratory syncytial virus, mumps virus, measles virus), adenoviruses, rhinoviruses, coronaviruses, reoviruses, togaviruses (e.g., rubella virus), parvoviruses, poxyiruses (e.g., variola virus, vaccinia virus), enteroviruses (e.g., poliovirus, coxsackievirus), hepatitis viruses (including A, B and C), herpesviruses (e.g., Herpes simplex virus, varicella-zoster virus, cytomegalovirus, Epstein-Barr virus), rotaviruses, Norwalk viruses, hantavirus, arenavirus, rhabdovirus (e.g., rabies virus), retroviruses (including HIV, HTLV-I and -II), papovaviruses (e.g., papillomavirus), polyomaviruses, and picornaviruses, and the like), and bacteria (including a wide variety of pathogenic and non-pathogenic prokaryotes of interest including *Bacillus; Vibrio*, e.g., *V. cholerae; Escherichia*, e.g., Enterotoxigenic *E. coli, Shigella*, e.g., *S. dysenteriae; Salmonella*, e.g., *S. typhi; Mycobacterium* e.g., *M. tuberculosis, M. leprae; Clostridium*, e.g., *C. botulinum, C. tetani, C. difficile, C. peffringens; Comyebacterium*, e.g., *C. diphtheriae; Streptococcus, S. pyogenes, S. pneumoniae; Staphylococcus*, e.g., *S. aureus; Haemophilus*, e.g., *H. influenzae; Neisseria*, e.g., *N. meningitidis, N. gonorrhoeae; Yersinia*, e.g., *G. lamblia Y. pestis, Pseudomonas*, e.g., *P. aeruginosa, P. putida; Chlamydia*, e.g., *C. trachomatis; Bordetella*, e.g., *B. pertussis; Treponema*, e.g., *T. palladium*; and the like) may be used.

In a preferred embodiment, the targeting moiety is all or a portion (e.g., a binding portion) of a ligand for a cell surface receptor. Suitable ligands include, but are not limited to, all or a functional portion of the ligands that bind to a cell surface receptor selected from the group consisting of insulin receptor (insulin), insulin-like growth factor receptor (including both IGF-1 and IGF-2), growth hormone receptor, glucose transporters (particularly GLUT 4 receptor), transferrin receptor (transferrin), epidermal growth factor receptor (EGF), low density lipoprotein receptor, high density lipoprotein receptor, leptin receptor, estrogen receptor (estrogen); interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor (VEGF), PDGF receptor (PDGF), transforming growth factor receptor (including TGF-.alpha. and TGF-.beta.), EPO receptor (EPO), TPO receptor (TPO), ciliary neurotrophic factor receptor, prolactin receptor, and T-cell receptors. In particular, hormone ligands are preferred. Hormones include both steroid hormones and proteinaceous hormones, including, but not limited to, epinephrine, thyroxine, oxytocin, insulin, thyroid-stimulating hormone, calcitonin, chorionic gonadotropin, cortictropin, follicle-stimulating hormone, glucagon, leuteinizing hormone, lipotropin, melanocyte-stimulating hormone, norepinephrine, parathryroid hormone, thyroid-stimulating hormone (TSH), vasopressin, enkephalins, seratonin, estradiol, progesterone, testosterone, cortisone, and glucocorticoids and the hormones listed above. Receptor ligands include ligands that bind to receptors such as cell surface receptors, which include hormones, lipids, proteins, glycoproteins, signal transducers, growth factors, cytokines, and others.

In another embodiment, the targeting moiety is a carbohydrate. As used herein, the term "carbohydrate" includes compounds with the general formula $Cx(H_2O)_y$. Monosaccharides, disaccharides, and oligo- or polysaccharides are all included within the definition and comprise polymers of various sugar molecules linked via glycosidic linkages. Particularly preferred carbohydrates are those that comprise all or part of the carbohydrate component of glycosylated proteins, including monomers and oligomers of galactose, mannose, fucose, galactosamine, (particularly N-acetylglucosamine), glucosamine, glucose and sialic acid, and in particular the glycosylation component that allows binding to certain receptors such as cell surface receptors. Other carbohydrates comprise monomers and polymers of glucose, ribose, lactose, raffinose, fructose, and other biologically significant carbohydrates. In particular, polysaccharides (including, but not limited to, arabinogalactan, gum arabic, mannan, etc.) have been used to deliver MRI agents into cells; see U.S. Pat. No. 5,554,386, hereby incorporated by reference in its entirety.

In another embodiment, the targeting moiety is a lipid. As used herein, the term "lipid" includes fats, fatty oils, waxes, phospholipids, glycolipids, terpenes, fatty acids, and glycerides, particularly the triglycerides. Also included within the definition of lipids are the eicosanoids, steroids and sterols, some of which are also hormones, such as prostaglandins, opiates, and cholesterol.

In a preferred embodiment, the targeting moiety may be used to either allow the internalization of the contrast agent to the cell cytoplasm or localize it to a particular cellular compartment, such as the nucleus. In a preferred embodiment, the targeting moiety is all or a portion of the HIV-1 Tat protein, and analogs and related proteins, which allows very high uptake into target cells (See for example, Fawell et al., *PNAS USA* 91:664 (1994); Frankel et al., *Cell* 55:1189 (1988); Savion et al., *J. Biol. Chem.* 256:1149 (1981); Derossi et al., *J. Biol. Chem.* 269:10444 (1994); and Baldin et al., *EMBO J.* 9:1511 (1990), all of which are incorporated by reference.

In a preferred embodiment, the targeting moiety is a nuclear localization signal (NLS). NLSs are generally short, positively charged (basic) domains that serve to direct the moiety to which they are attached to the cell's nucleus. Numerous NLS amino acid sequences have been reported including single basic NLS's such as that of the SV40 (monkey virus) large T Antigen (Pro Lys Lys Lys Arg Lys Val), Kalderon (1984), et al., *Cell*, 39:499-509; the human retinoic acid receptor-.beta. nuclear localization signal (ARRRRP); NFκB p50 (EEVQRKRQKL; Ghosh et al., *Cell* 62:1019 (1990); NF.kappa.B p65 (EEKRKRTYE; Nolan et al., Cell 64:961 (1991); and others (see for example Boulikas, *J. Cell. Biochem.* 55(1):32-58 (1994), hereby incorporated by reference) and double basic NLS's exemplified by that of the *Xenopus* (African clawed toad) protein, nucleoplasmin (Ala Val Lys Arg Pro Ala Ala Thr Lys Lys Ala Gly Gln Ala Lys Lys Lys Lys Leu Asp), Dingwall, et al., Cell, 30:449-458, 1982 and Dingwall, et al., *J. Cell Biol.*, 107:641-849; 1988). Numerous localization studies have demonstrated that NLSs incorporated in synthetic peptides or grafted onto reporter proteins not normally targeted to the cell nucleus cause these peptides and reporter proteins to be concentrated in the nucleus (see, for example, Dingwall, and Laskey, *Ann, Rev. Cell Biol.*, 2:367-390, 1986; Bonnerot, et al., *Proc. Natl.*

*Acad. Sci. USA,* 84:6795-6799, 1987; Galileo, et al., *Proc. Natl. Acad. Sci. USA,* 87:458-462, 1990.

In another embodiment, targeting moieties for the hepatobiliary system are used (see U.S. Pat. Nos. 5,573,752 and 5,582,814, both of which are hereby incorporated by reference in their entirety).

In specific embodiments, a cell-binding agent is utilized as the targeting moiety. Selection of the appropriate cell-binding agent is a matter of choice that depends upon the particular cell population to be targeted, but in general monoclonal antibodies are preferred if an appropriate one is available.

For example, the monoclonal antibody MY9 is a murine $IgG_1$ antibody that binds specifically to the CD33 antigen (J. D. Griffin et al. *Leukemia Res.,* 8: 521 (1984)) which can be used if the target cells express CD33, such as in the disease of acute myelogenous leukemia (AML). Similarly, the monoclonal antibody anti-B4 is a murine $IgG_1$ that binds to the CD19 antigen on B cells (Nadler et al., *J. Immunol.* 131: 244-250 (1983)) and can be used if the target cells are B cells or diseased cells that express this antigen, such as in non-Hodgkin's lymphoma or chronic lymphoblastic leukemia. Similarly, the antibody N901 is a murine monoclonal $IgG_1$ antibody that binds to CD56 found on small cell lung carcinoma cells and on cells of other tumors of neuroendocrine origin (Roy et al. *J. Nat. Cancer Inst.* 88:1136-1145 (1996)).

Antibodies that target solid tumors are also useful, such as the C242 antibody which binds to a carbohydrate antigen found on MUC1 present on pancreatic and colorectal tumors. (U.S. Pat. No. 5,552,293); antibody J591, which binds to PSMA (prostate specific membrane antigen) which is expressed on prostate cancer cells and on endothelial cells of neovasculature in tumors (U.S. Pat. No. 6,107,090, He Liu et al. *Cancer Res.* 57: 3629-3634 (1997); and antibodies to HER-2, which is overexpressed on certain breast tumors. Examples of anti-HER-2 antibodies are the TA1 antibody (L. A. Maier et al. *Cancer Res.* 51: 5361-5369 (1991)) and the 4D5 antibody (U.S. Pat. Nos. 6,387,371 and 6,399,063).

Additionally, GM-CSF, which binds to myeloid cells, can be used as a cell-binding agent to diseased cells from acute myelogenous leukemia. IL-2, which binds to activated T-cells, can be used for prevention of transplant graft rejection, for therapy and prevention of graft-versus-host disease, and for treatment of acute T-cell leukemia. MSH, which binds to melanocytes can be used for the treatment of melanoma. Folic acid, which targets the folate receptor expressed on ovarian and other cancers, is also a suitable cell-binding agent.

Cancers of the breast and testes can be successfully targeted with estrogen (or estrogen analogues) or androgen (or androgen analogues), respectively, as cell-binding agents.

As is further described below, the contrast agents of the present invention find use in a wide variety of applications. These applications include in vitro and in vivo monitoring of gene expression, disease progression, drug response(s) and biodistribution assays. In particular, in vivo real time acquisition of data in living animals that are not sacrificed can be a powerful tool. In addition, in vitro and in vivo imaging of cells, tissues and animals may be done using a plurality of these agents, particularly utilizing sequential administration and image collection.

The contrast agents of the invention may be used in a similar manner to the known gadolinium MRI agents (see for example, Meyer et al., supra; U.S. Pat. No. 5,155,215; U.S. Pat. No. 5,087,440; Margerstadt et al., *Magn. Reson. Med.* 3:808 (1986); Runge et al., *Radiology* 166:835 (1988); and Bousquet et al., *Radiology* 166:693 (1988). The metal ion complexes are administered to a cell, tissue or subject as is known in the art.

The terms "patient", "recipient", "subject", and "host" are used interchangeably and, for the purposes of the present invention, include both humans and other animals and organisms, such as experimental animals. Thus, the methods are applicable to both human therapy and veterinary applications, as well as research. In addition, the contrast agents of the invention may be used to image tissues or cells in vitro or in vivo (for example, see Aguayo et al., *Nature* 322:190 (1986)).

Mammalian species which benefit from the methods and contrast agents of the invention include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Thus, as used herein, the terms "patient", "recipient", "subject", and "host" are intended to include such human and non-human species.

As will be understood by one of skill in the art, there are over 200 cell types in the human body. It is believed that the methods of the subject invention can be used to label and/or visualize any of these cell types for diagnostic and/or therapeutic or other purposes. For example, any cell arising from the ectoderm, mesoderm, or endoderm germ cell layers can be labeled or visualized using the contrast agent and methods of the subject invention. It will be understood by one of skill in the art that the methods of the present invention are also applicable for veterinary purposes and research purposes.

The cells labeled and/or visualized using the contrast agents and methods of the invention can be normal cells or cancer cells, primary cells, cultured cells, cells of a cell line, embryonic and adult stem cells, genetically modified cells, non-genetically modified cells, or other cells.

The cells labeled and/or visualized using the contrast agents and methods of the invention can range in plasticity from totipotent or pluripotent stem cells (e.g., adult or embryonic), precursor or progenitor cells, to highly specialized cells, such as those of the central nervous system (e.g., neurons and glia). Stem cells can be obtained from a variety of sources, including embryonic tissue (ES cells), fetal tissue, adult tissue, umbilical cord blood, peripheral blood, bone marrow, and brain, for example.

Methods and markers commonly used to identify stem cells and to characterize differentiated cell types are described in the scientific literature (e.g., Stem Cells: Scientific Progress and Future Research Directions, Appendix E1-E5, report prepared by the National Institutes of Health, June, 2001, which is incorporated herein by reference in its entirety). Such methods and markers can be used to characterize cells before, during, and/or after labeling and/or visualizing the cells with the contrast agents and methods of the invention. The list of adult tissues reported to contain stem cells is growing and includes bone marrow, peripheral blood, umbilical cord blood, brain, spinal cord, dental pulp, blood vessels, skeletal muscle, cardiac muscle, epithelia of the skin and digestive system, cornea, retina, liver, and pancreas.

As indicated above, the cells with which the contrast agents and methods of the invention can be used can be of any animal species; e.g., mammals, avians, reptiles, fish, and amphibians. Examples of mammalian cells that can be labeled and/or visualized in accordance with the present invention include but are not limited to human and non-human primate cells, ungulate cells, rodent cells, and lagomorph cells. Primate cells with which the invention may be carried out include but are not limited to cells of humans, chimpanzees, baboons, cynomolgus monkeys, and any other New or Old World monkeys. Ungulate cells with which the invention may be carried out include but are not limited to cells of bovines, porcines, ovines, caprines, equines, buffalo and bison. Rodent cells with which the invention may be carried out include but are not limited to mouse, rat, guinea pig, hamster and gerbil cells. Rabbit cells are an example of cells of a lagomorph species with which the invention may be performed.

As described herein, the quantum dots of the present invention may be used to tag/label and visualize various targets (molecules of interest; pathogenic or non-pathogenic microorganisms or entities such as bacteria, virus, prions; cells; tissues, etc.) within biological tissue in vitro or in vivo. Examples of the many uses for quantum dots as contrast agents and tools in biological imaging, and the useful modifications that can be made to them (to reduce toxicity, for example) are described in Michalet et al. (*Science*, January, 2005, 307:538-544), Jaiswal et al. (*Trends in Cell Biology*, September, 2004, 14(9):497-504); Gao et al. (*Nature Biotechnology*, August 2004, 22(8):969-976); Smith et al. (*Photocom. Photobiol.*, 2004, November-December 80(3):377-385, Epub ahead of print), Stavis et al. (*Lab Chip*, March, 2005, 5(3):337-343, Epub Jan. 13, 2005); Parungo et al., *J. Thorac. Cardiovasc. Surg.*, April, 2005, 129(4):844-850); Bentzen et al. (*Nano Lett.*, April, 2005, 5(4):591-595); Zhelev et al. (*Chem Commun (Camb)*), August, 2005, 15:1980-1982, Epub Feb, 24, 2005); Alivisatos et al. (*Annu Rev. Biomed. Eng.*, July, 2004, Epub ahead of print); Wu et al., (*Methods Cell Biol.*, 2004, 75:171-183); Jiang et al. (*Trends Biotechnol.*, December, 2004, 22(12:607-609); and Voura et al. (*Nat. Med.*, September, 2004, 10(9):993-998), which are incorporated herein by reference in their entirety, and can be used with the quantum dots of the present invention.

The opaque mediums within which target entities may be labeled and visualized include non-biological systems. For example, the contrast agents of the present invention may be used to visualize targets such as toxins, pathogenic bacteria, or other contaminants in soil or water (Lee et al., *Applied and Environmental Microbiology*, October, 2004, 70(10):5732-5736; Su et al., *Anal. Chem.*, August, 2004, 76(16):4806-4810, which are incorporated herein by reference in their entirety).

The terms "comprising", "consisting of" and "consisting essentially of" are defined according to their standard meaning. The terms may be substituted for one another throughout the instant application in order to attach the specific meaning associated with each term. The phrases "isolated" or "biologically pure" refer to material that is substantially or essentially free from components which normally accompany the material as it is found in its native state.

The terms "linked", "joined", "grafted", "tethered", "associated", "attached", "bonded", "functionalized", and "conjugated" in the context of the nanoparticles (Qdots) of the invention, are used interchangeably to refer to any method known in the art for functionally connecting moieties (such as TAT, folic acid, other targeting moieties or chemical entities), including, without limitation, recombinant fusion, covalent bonding, disulfide bonding, ionic bonding, hydrogen bonding, and electrostatic bonding.

As used in this specification and the appended claims, the singular forms "a", "an", and "the" include plural reference unless the context clearly dictates otherwise. Thus, for example, a reference to "a nanoparticle" includes more than one such nanoparticle, and the like. Reference to "a targeting moiety" includes more than one such targeting moiety. Reference to "a cell" includes more than one such cell. Reference to "an image" includes more than one such image. For example, an image can include one or more "stills" or "screen shots", or a stream of continuous images and recorded as a video.

The practice of the present invention can employ, unless otherwise indicated, conventional techniques of molecular biology, microbiology, recombinant DNA technology, electrophysiology, and pharmacology, that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover ed. 1985); Perbal, B., A Practical Guide to Molecular Cloning (1984); the series, Methods In Enzymology (S. Colowick and N. Kaplan eds., Academic Press, Inc.); Transcription and Translation (Hames et al. eds. 1984); Gene Transfer Vectors For Mammalian Cells (J. H. Miller et al. eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. eds. (1991) IRL Press)).

Following are examples that illustrate materials, methods, and procedures for practicing the invention. The examples are illustrative and should not be construed as limiting.

Materials and Methods

Synthesis of CdS:Mn/ZnS Core/Shell Quantum Dots. Yellow-emitting $Mn^{2+}$ doped core/shell nanocrystals of ZnS-passivated CdS:Mn were produced via a reverse micelle process. ($Cd^{2+}+Mn^{2+}$)-containing aqueous solution is prepared by dissolving $Cd(CH_3COO)_2.2H_2O$ and $Mn(CH_3COO)_2$ in water, and $S^{2-}$- and $Zn^{2+}$-containing aqueous solutions are prepared respectively by dissolving $Na_2S$ and $Zn(CH_3COO)_2$ in water. Each solution was stirred with an anionic surfactant AOT/heptane stock solution. CdS:Mn/ZnS quantum dots are formed by mixing ($Cd^{2+}+Mn^{2+}$)- and $S^{2-}$-containing micellar solutions for 15 min, followed by the addition of $Zn^{2+}$-containing micellar solution at a very slow rate of ~1.5 ml/min for ZnS shell growth over the CdS:Mn core surface. A surplus of S ions was maintained in the CdS:Mn nanocrystal micellar solution for further ZnS shell growth. All reactions were conducted at room temperature. The concentrations of $Cd^{2+}$, $S^{2-}$, and $Zn^{2+}$ in water were 0.1, 0.66, and 0.26 M, respectively (0.048 g of $Cd(CH_3COO)_2.2H_2O$ in 1.8 ml of water, 0.2812 g of $Na_2S$ in 5.4 ml of water, and 0.264 g of $Zn(CH_3COO)_2$ in 5.4 ml of water are used). The Mn solution concentration in CdS is 2 mol % (0.00062 g of $Mn(CH_3COO)_2$ is used). The molar ratio of water-to-surfactant (W) is 10 for all micellar solutions. The concentration of AOT in heptane is 0.1 M. More detailed compositions of each micellar solution are shown in Table 1.

TABLE 1

| Compositions of Each Micellar Solution | | | |
|---|---|---|---|
| | ($Cd^{2+} + Mn^{2+}$)- micellar solution | $S^{2-}$- micellar solution | $Zn^{2+}$- micellar solution |
| Water | 1.8 ml | 5.4 ml | 5.4 ml |
| AOT | 4.46 g | 13.38 g | 13.38 g |
| Heptane | 100 ml | 300 ml | 300 ml |

Silica coating and Subsequent Surface-Functionalization of Quantum Dots. After addition of the Zn micellar solution, 2.5 ml of tetraethyl orthosilicate (TEOS) is injected into CdS:Mn/ZnS micellar solution and mixed for 15 min at room temperature. The hydrolysis of TEOS and condensation reaction is initiated by adding NH$_4$OH in the form of micellar solution, which is prepared by mixing 1.5 ml of NH$_4$OH (30 wt %) with AOT (3.69 g)/heptane (82.5 ml) stock solution. After polymerization for 24 hr at room temperature, 1.25 ml of TEOS and 0.25 ml of 3-(Aminopropyl)triethoxysilane (APTS) are injected into above solution and mixed for 10 min. And then, another NH$_4$OH micellar solution (prepared by mixing 0.9 ml of NH$_4$OH with AOT (2.21 g)/heptane (50 ml) stock solution) and 3-(Trihydroxysilyl)propyl methylphosphonate (THPMP) (prepared by mixing 0.75 ml of THPMP and 3.6 ml of water with AOT (4.42 g)/heptane (50 ml) stock solution) are injected subsequently and reacted for 24 hours. And silica-overcoated-, surface-functionalized quantum dots are precipitated by addition of a small amount of methanol. After thorough washing with methanol, these quantum dots are solubilized stably in a sodium phosphate buffer solution (pH 7).

Characterization. A JEOL JSM 6400 electron microscope operated at 15 kV was used for EDS analysis. A Perkin-Elmer PHI 5100 x-ray photoelectron spectrometer and Mg K$_\alpha$ x-ray (1253.6 eV) were used for XPS/ESCA. Survey scans were collected from 1100 to 0 eV with a step of 0.5 eV, a time/step of 30 ms, and a pass energy of 89.45 eV. Multiplex scans were colleted with a step of 0.1 eV, a time/step of 50 ms, and pass energy of 35.75 eV. A JEOL 2010F transmission electron microscope operated at 200 kV was used for imaging and direct determination of the nanocrystal size. The XRD patterns were obtained with a Philips MRD X'Pert system for information on structure and crystal size. XRD pattern was collected in the step scan mode, typically with a scan range of 15°-80°, a step of 0.01°, and a glazing angle of incident x-ray of 1°.

Quantum yields of n-dodecanethiol- and ZnS-passivated CdS:Mn nanocrystals dispersed in chloroform were determined by comparing the integrated emission to those from Coumarin 6, Coumarin 30, and perylene at the excitation wavelength of 385 nm. Coumarin 6, Coumarin 30, and perylene were dissolved in ethanol, acetonitrile, and cyclohexane, respectively. The optical densities of the sample and reference solutions were 0.065±0.003 at the excitation wavelength.

EXAMPLE 1

Core/Shell Structure and Size of Nanocrystals

Figure 2A:
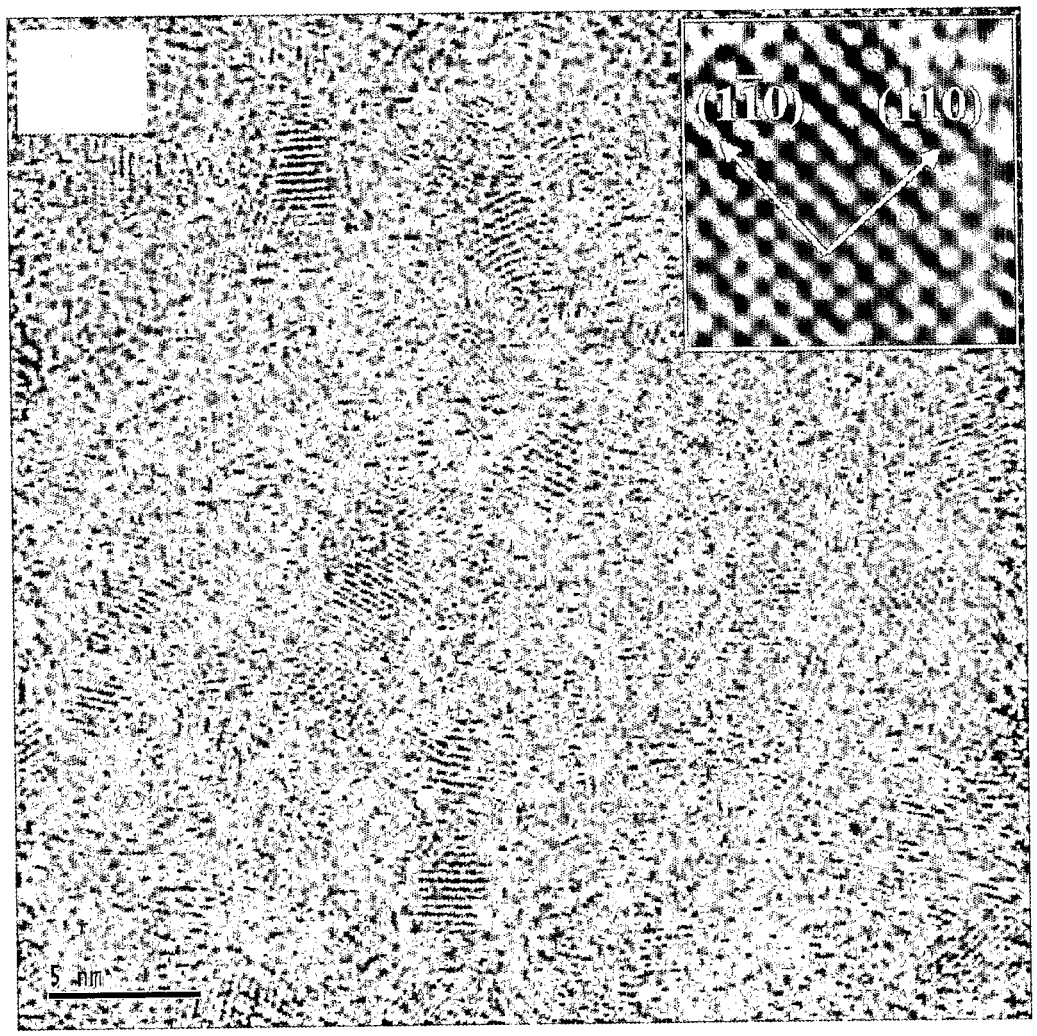
FIGS. 2A and 2B show transmission electron microscope (TEM) images of CdS:Mn/ZnS nanocrystals with a mean particle size of 3.1 nm and x-ray diffraction (XRD) patterns, respectively. The length bar at lower left corner in FIG. 2A indicates 5 nm. The inset in FIG. 2A is a nanocrystal viewed along the [001] zone axis and (1$\bar{1}$0) and (110) planes are intersecting at 90°.
Figure 2B:
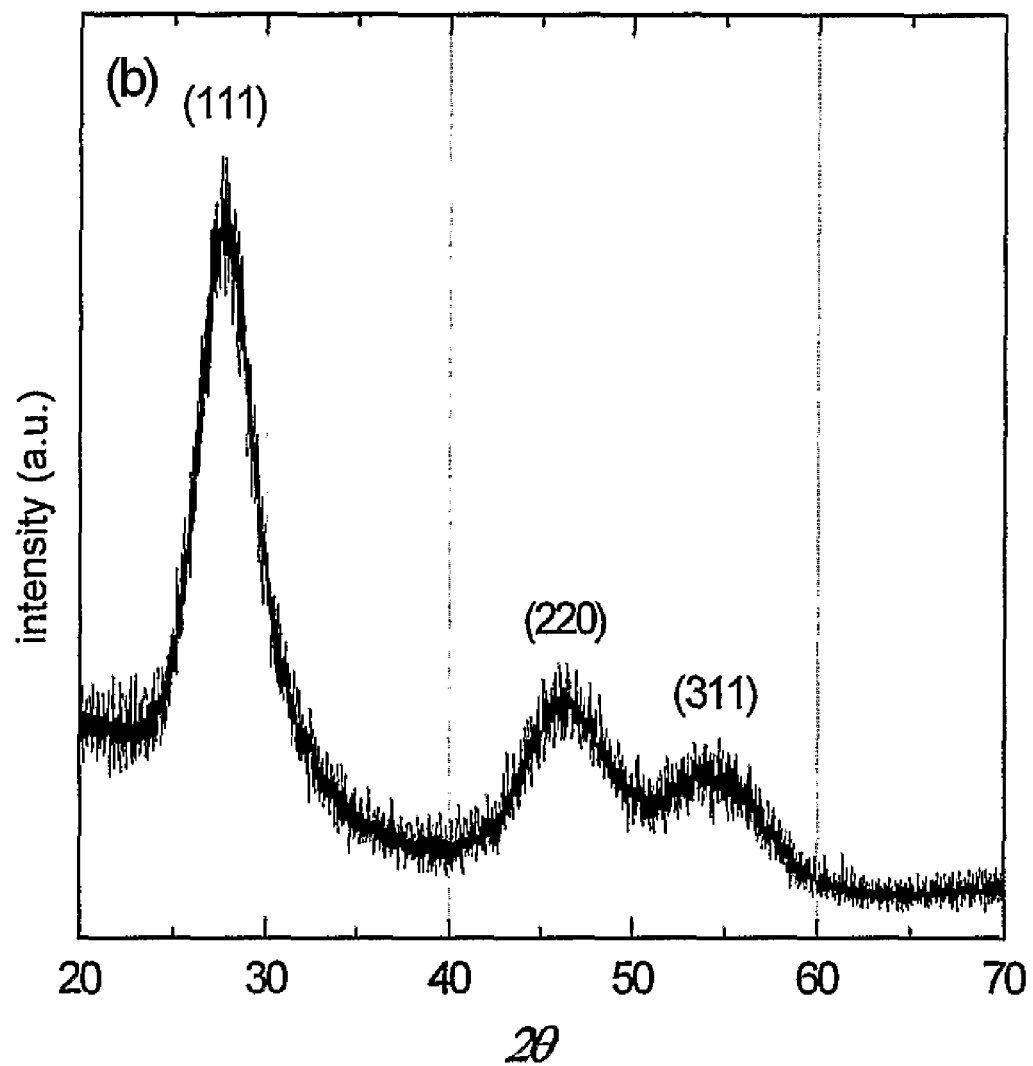

It has been reported that synthesized nanocrystals consist of a CdS core/ZnS shell structure, based on UV-visible absorption spectroscopy and x-ray photoelectron spectroscopy (XPS)/energy-dispersive spectroscopy (EDS) (Yang, H. and P. H. Holloway, *Appl. Phys. Lett.* 2003, 82:1965-1967). Since XPS is a surface sensitive method and EDS is a 'bulk' method of analysis (Brundle, C. R., Encyclopedia of Materials Characterization, (Eds: C. R. Brundle, C. A. Evans, Jr., S. Wilson), Butterworth-Heinemann, Boston 1992), the samples with CdS core/ZnS shell structure should experience an attenuation of the signals from buried core element, i.e., Cd, in XPS relative to EDS. Thus XPS spectra should be dominated by the shell, while EDS spectra should exhibit the elements in both the shell and the core structure averaged over many nanocrystal thickness. XPS survey spectra of CdS:Mn, ZnS:Mn, and CdS:Mn/ZnS core/shell nanocrystals are shown in FIG. 1. The primary Cd 3d$_5$ and Zn 2p$_3$ XPS lines are observed in FIG. 1, trace (a) and trace (b), respectively, and those two lines are present in trace (c) of FIG. 1. Accurate quantitative compositions of Zn/Cd in XPS were obtained by integrating the peak area and dividing by the atomic sensitivity factors (Wagner, C. D., W. M. Riggs, L. E. Davis, J. F. Moulder, G. E. Mullenberg, Handbook of X-ray Photoelectron Spectroscopy, Perkin Elmer Corp., Eden Prarie, Minn. 1979). The Zn/Cd ratios from EDS and XPS in CdS:Mn/ZnS nanocrystals are 5.5 and 6.6, respectively, supporting that the nanocrystals consist of layered structure. Transmission electron microscope (TEM) images of CdS:Mn/ZnS core/shell nanocrystals, whose average size is observed to be 3.1 nm, are shown in FIG. 2A. The size of the nanocrystal core was measured using XRD patterns (FIG. 2B) reduced with the Debye-Scherrer equation and found to be 2.3 nm. Since the shell layer does not affect the X-ray diffraction (XRD) peak width from the core (X. Peng, M. C. Schlamp, A. V. Kadavanich, A. P. Alivisatos, *J. Am. Chem. Soc.* 1997, 119:7019; L. Manna, E. C. Scher, L. Li, A. P. Alivisatos, *J. Am. Chem. Soc.* 2002, 124:7136), the difference between the TEM and XRD diameters (0.4 nm) can be attributed to the ZnS shell thickness (~1.5 monolayers of ZnS). Diffraction peaks from nanocrystals matched those of bulk zinc blende CdS (Joint Committee on Powder Diffraction Standards (JCPDS), International Center for Diffraction Data (ICDD), Swarthmore, Pa.). The inset in FIG. 2A shows atom resolution images of a nanocrystal with the zinc blende structure and the ($1\bar{1}0$) and (110) planes are identified.

EXAMPLE 2

Photoluminescence (PL) and Quantum Yield

Figures 3A, 3B:
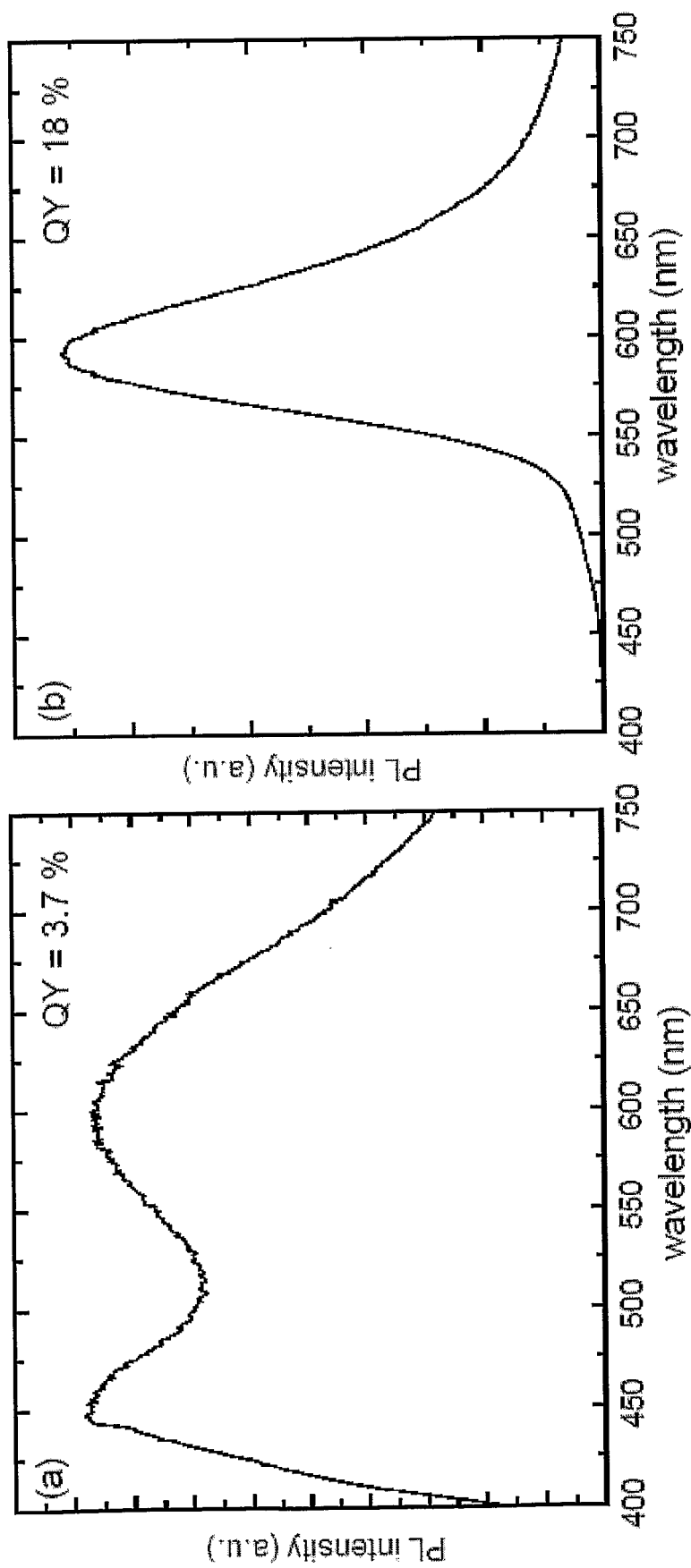
FIGS. 3A and 3B show PL emission spectra of n-dodecanethiol- and ZnS-passivated CdS:Mn nanocrystals, respectively.

PL emission spectra, obtained using 325 nm HeCd laser excitation, of n-dodecanethiol-passivated and ZnS-passivated CdS:Mn nanocrystals are compared in FIG. 3A and FIG. 3B, respectively. Note that PL measurements were carried out in the solid-state sample, i.e., ~200 nm thick CdS:Mn/ZnS nanocrystal layers on the glass substrate. The Mn$^{2+}$ $_4T_1$-$^6A_1$ transition at ~600 nm is observed from both nanocrystalline samples. In addition to the Mn emission at ~600 nm, emission from a surface-related defect (shallow trap) is observed at ~450 nm from organically passivated nanocrystals. This defect emission originates from the localized surface states in the band gap, which presumably are formed by the lack of bonding to surface S ions. In contrast, no defect-related emission is observed from inorganically passivated nanocrystals, indicating the successful complete passivation of CdS:Mn core surface by the ZnS shell layer.

Figure 4:
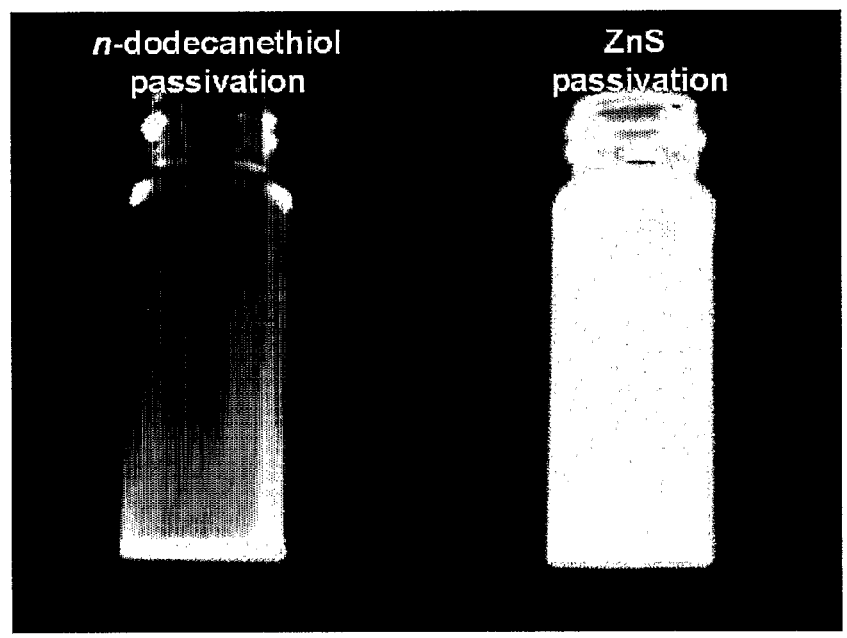
FIG. 4 shows a comparison of PL brightness from n-dodecanethiol- and ZnS-passivated CdS:Mn nanocrystals under 366 nm UV irradiation.

The quantum yields of CdS:Mn nanocrystals with either a n-dodecanethiol or ZnS capping layer were measured in chloroform solutions and found to be 3.7 and 18%, respectively. Note that for quantum yield measurement, CdS:Mn/ZnS core/shell nanocrystals were capped with n-dodecanethiol in order to be soluble in chloroform. The value of 3.7% for organically capped CdS:Mn is reasonable since it is close to the quantum yields reported from organically passivated ZnS:Mn nanocrystals (1-4%) (Kubo, T., T. Isobe, M. Senna, *J. Lumin.* 2002, 99:39; Bol, A., A. Meijerink, *J. Phys. Chem. B* 2001, 105, 10197). The enhanced quantum yield of n-dodecanethiol-capped CdS:Mn/ZnS nanocrystals is a direct result of more effective surface passivation, by which nonradiative recombination paths are reduced significantly. A visual comparison of organically and inorganically passivated nanocrystals is shown in FIG. 4. Both samples are standing on a handheld-UV lamp providing 366 nm multiband irradiation, and it is obvious that the ZnS-passivated nanocrystals are much brighter.

EXAMPLE 3

Effects of UV irradiation and Photooxidation

Figure 5:
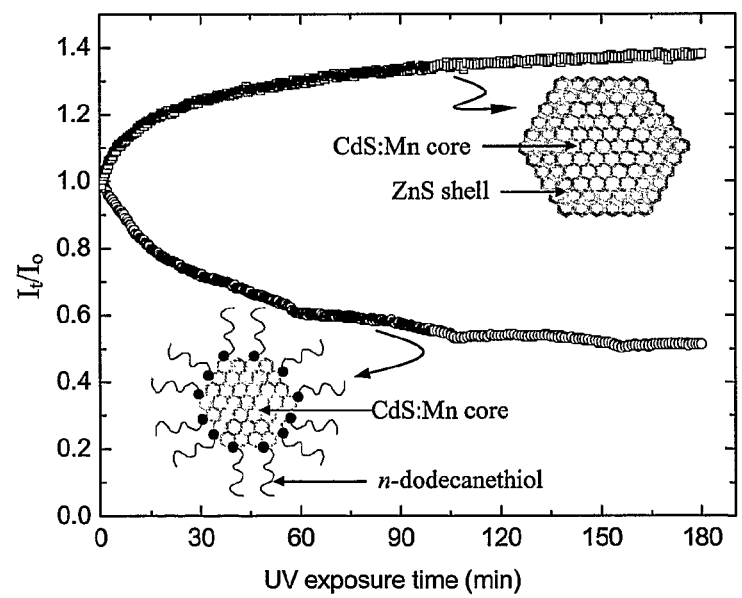
FIG. 5 shows variations of PL emission intensity of n-dodecanethiol- and ZnS-passivated CdS:Mn nanocrystals versus time exposed to 400 nm UV light. The monitored wavelengths are 580 nm and 585 nm for n-dodecanethiol- and ZnS-passivated CdS:Mn nanocrystals, respectively.
Figure 6:
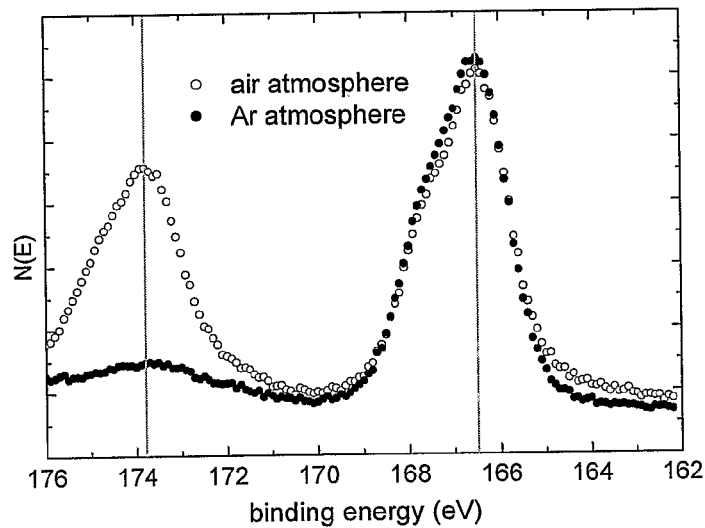
FIG. 6 shows XPS spectra of core/shell nanocrystals after 366 nm UV irradiated for 3 hours in either air and Ar. The large peak at 173.8 eV for irradiation in air suggests formation of $ZnSO_4$.

The change of PL emission intensity from organically and inorganically passivated CdS:Mn during 400 nm UV irradiation was monitored at room temperature using a monochromatized 300 W Xe light source (FIG. 5). The 400 nm UV irradiation was estimated to have a powder density of 655 $\mu W/cm^2$. Organically passivated CdS:Mn nanocrystals exhibit a significant reduction (~45% after 3 hours) of the PL emission intensity upon UV exposure, while CdS:Mn/ZnS core/shell nanocrystals show an increased PL intensity (~40% after 3 hours). The reduced PL emission intensity of n-dodecanethiol-passivated CdS:Mn nanocrystals presumably results from the fact that the bonding between the Cd (from nanocrystal) and S ions (from organic passivating species) at the surface is deteriorated by UV exposure. Accordingly, the density of nonradiative relaxation paths increases at the surface, resulting in a decreased PL emission intensity (C. Jin, C., J. Yu, L. Sun, K. Dou, S. Hou, U. Zhao, Y. Chen, S. Huang, *J. Lumin.* 1996, 66-67, 315; Pingbo, X., Z. Weiping, Y. Min, C. Houtong, Z. Weiwei, L. Liren, X. Shangda, *J. Colloid Interface Sci.* 2000, 229:534). The increased PL emission intensity observed in CdS:Mn/ZnS nanocrystals indicates the creation of more radiative or reduction of nonradiative paths as a result of UV irradiation. Enhancement of PL quantum efficiency of unpassivated ZnS:Mn nanocrystal as a result of UV exposure has been reported by other research groups (Bol, A., A. Meijerink, *J. Phys. Chem. B* 2001, 105: 10203; Cao, L., J. Zhang, S. Ren, S. Huang, *Appl. Phys. Lett.* 2002, 80:4300). Bol and Meijerink (2001) reported that a photochemical reaction (photooxidation) of oxygen and/or water with the surface of ZnS nanocrystal surface occurs, leading to the formation of $ZnSO_4$ and/or $Zn(OH)_2$, and these phases serve as passivating layers on the ZnS surface to reduce the nonradiative recombination paths. To study this possibility, XPS data were collected in the current study and are shown in FIG. 6. The S 2p from CdS:Mn/ZnS nanocrystals irradiated with UV for 3 hours in either air or Ar atmospheres are shown. This UV irradiation treatment was accomplished using a hand-held UV lamp providing 366 nm multiband photons with a power density of 1350 $\mu W/cm^2$. The S 2p peaks at ~166.5 and ~173.8 eV are due to S atoms in the CdS core/ZnS shell and in $ZnSO_4$, respectively (National Institute of Standards and Technology (NIST), X-ray Photoelectron Spectroscopy Database 20, Ver. 3.3). Clearly, $ZnSO_4$ is only formed by irradiation in air supporting the suggestion by Bol et al. (2001) that photooxidation occurs between the ZnS shell surface and oxygen or water in air but not in Ar. The small peak at ~173.8 eV for irradiation in Ar is the result of exposure to air prior to UV irradiation. These data support the conclusion that photooxidation production of a passivating surface sulfate is responsible for the enhanced PL emission. The PL intensity after 3 hours UV irradiation from core/shell nanocrystals remained constant when the UV irradiation was stopped for periods up to 2 hours and restarted. This observation would imply that the $ZnSO_4$ is stable and the photooxidation process is irreversible.

Figure 7:
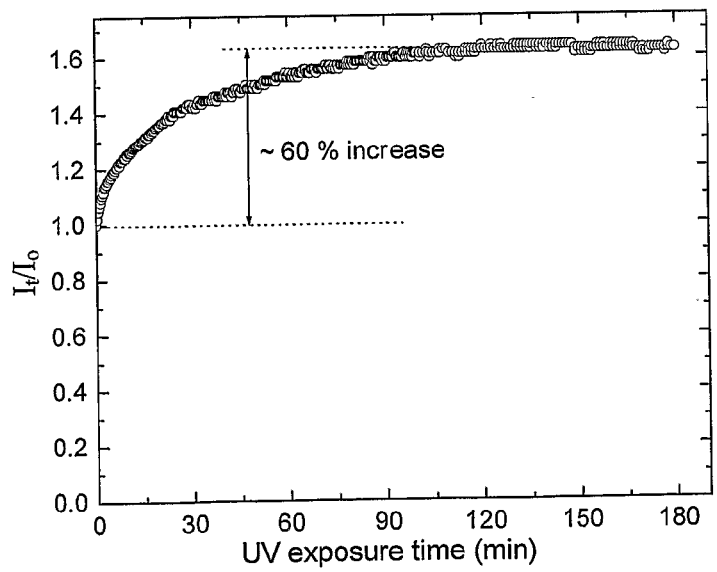
FIG. 7 shows variation of PL emission intensity of n-dodecanethiol-capped CdS:Mn/ZnS nanocrystals versus time exposed to 350 nm UV light. The monitored wavelength is 585 nm.

The variation with 350 nm UV irradiation time of the PL emission intensity from n-dodecanethiol-capped CdS:Mn/ZnS nanocrystals is shown FIG. 7. A 60% increased brightness was observed for an exposure of 3 hours, i.e., slightly greater than the increase reported above (40%) for a 3-hour exposure of CdS:Mn/ZnS nanocrystals (no n-dodecanethiol capping) to 400 nm UV. While the quantum yield of n-dodecanethiol-capped CdS:Mn/ZnS nanocrystals was not measured after the PL intensity was increased by UV irradiation for 3 hours, it may be estimated by multiplying the quantum yield without UV enhancement (18%) by the enhanced brightness (60%). Using this procedure, a final quantum yield of >28% would be expected.

Thus, synthesis of efficient and photostable ZnS-passivated CdS:Mn core/shell nanocrystals via a reverse micelle route has been described herein. Nanocrystals with a CdS:Mn/ZnS core/shell structure with a core crystal diameter of 2.3 nm and a shell thickness of 0.4 nm were obtained. Effective passivation of the CdS:Mn core surface by a ZnS shell was evident from the absence of a surface-related defect emission and a high quantum efficiency (18%) compared to n-dodecanethiol-passivated CdS:Mn nanocrystals (surface defect luminescence observed and a quantum yield of only 3.7%). Although n-dodecanethiol-passivated CdS:Mn nanocrystals suffered from the reduction of emission intensity during UV irradiation, ZnS-passivated core/shell nanocrystals exhibited the enhanced emission intensity during initial UV irradiation and saturated, stable emission during further UV irradiation. XPS data supported that CdS:Mn/ZnS nanocrystals experience the photooxidation during UV irradiation in air atmosphere. The surface sulfate ($ZnSO_4$), formed as a result of photooxidation, serves as a passivating layer and is responsible for the enhanced PL emission. It was also concluded that the $ZnSO_4$ is stable and the photooxidation process is irreversible. An even higher quantum yield (>28%) was estimated from these UV irradiated core/shell nanocrystals.

EXAMPLE 4

Magnetic Properties of CdS:Mn/ZnS Core/Shell Quantum Dots

Figure 8A:
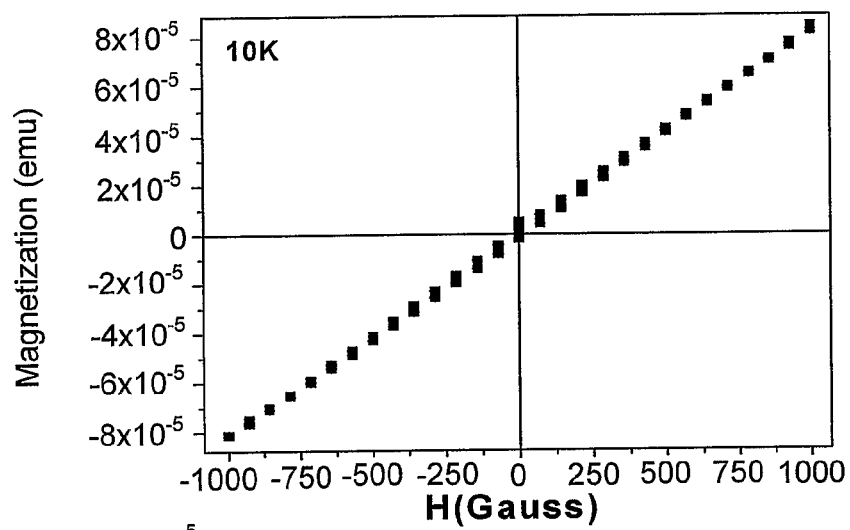
FIGS. 8A-8C show the magnetic field versus magnetization of Mn-doped core/shell quantum dots, measured at 10 K (FIG. 8A), 100 K (FIG. 8B), and 300 K (FIG. 8C).
Figure 8B:
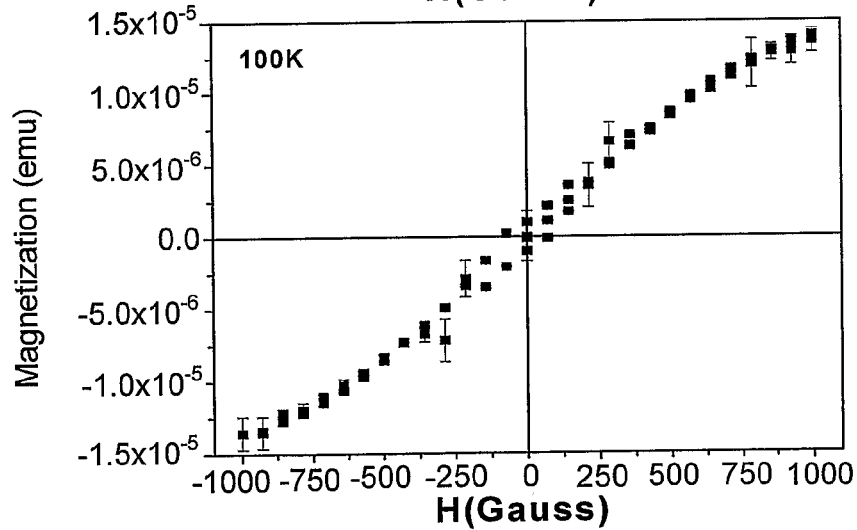
Figure 8C:
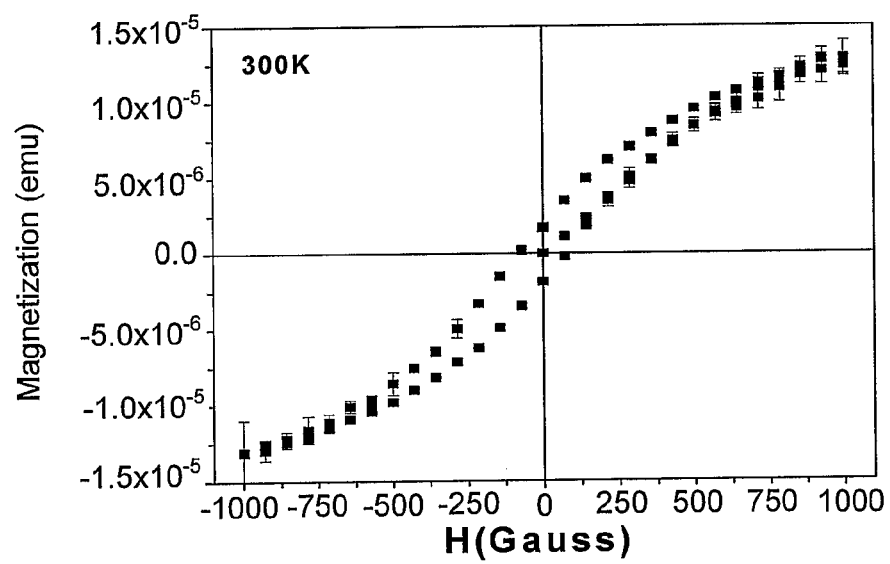
Figure 9A:
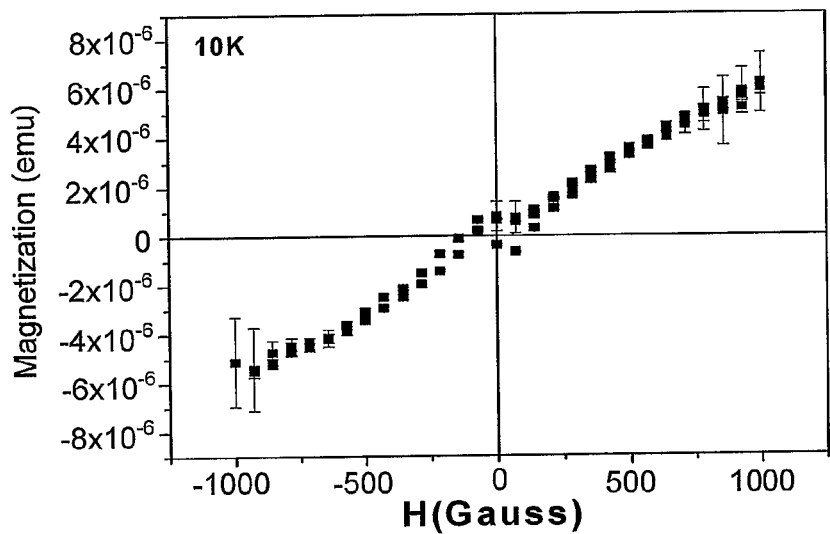
FIGS. 9A and 9B show the magnetic field versus magnetization of undoped core/shell quantum dots, measured at 10 K (FIG. 9A) and 300 K (FIG. 9B).
Figure 9B:
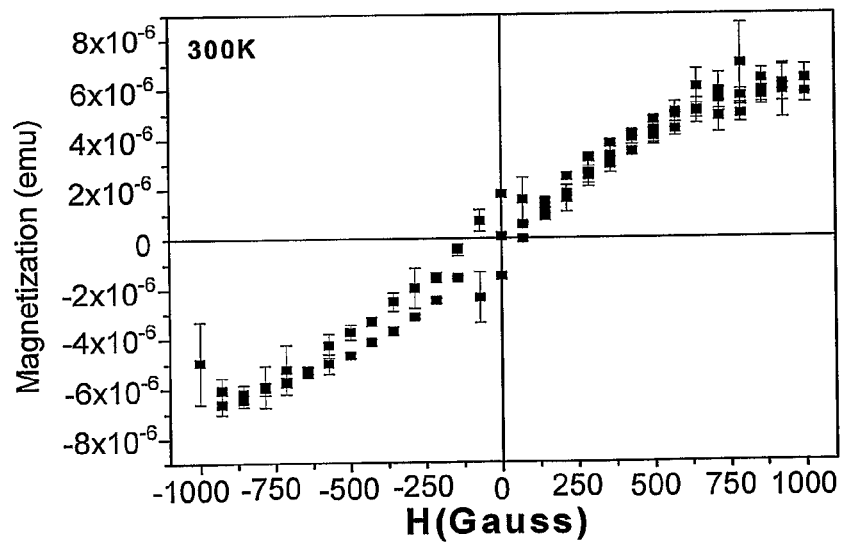
Figure 10A:
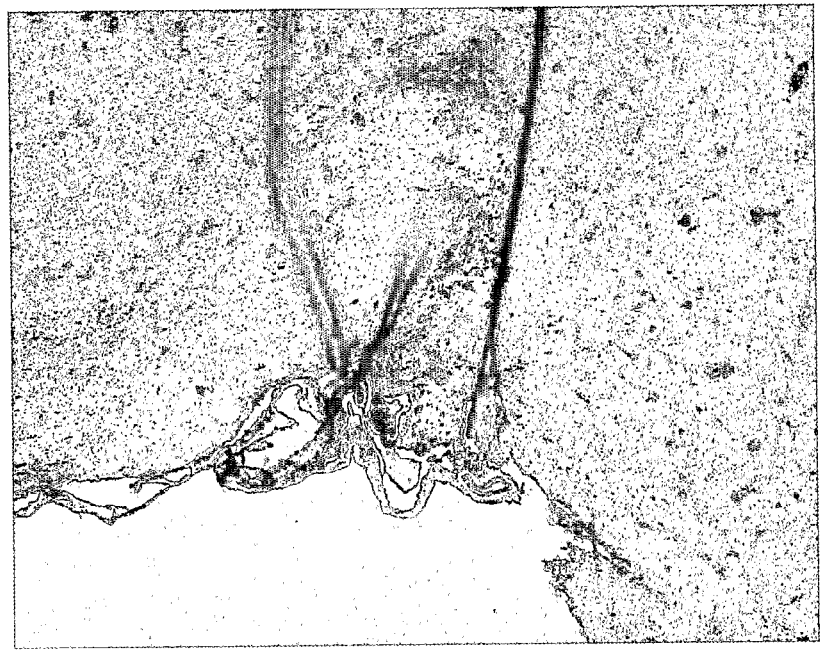
FIGS. 10A and 10B show branches of the right middle cerebral artery of rats following endovascular injection of 10 mg/ml TAT-grafted quantum dots (CdS:Mn/ZnS) of the invention. The duration of the injection was three minutes.
Figure 10B:
Figure 11:
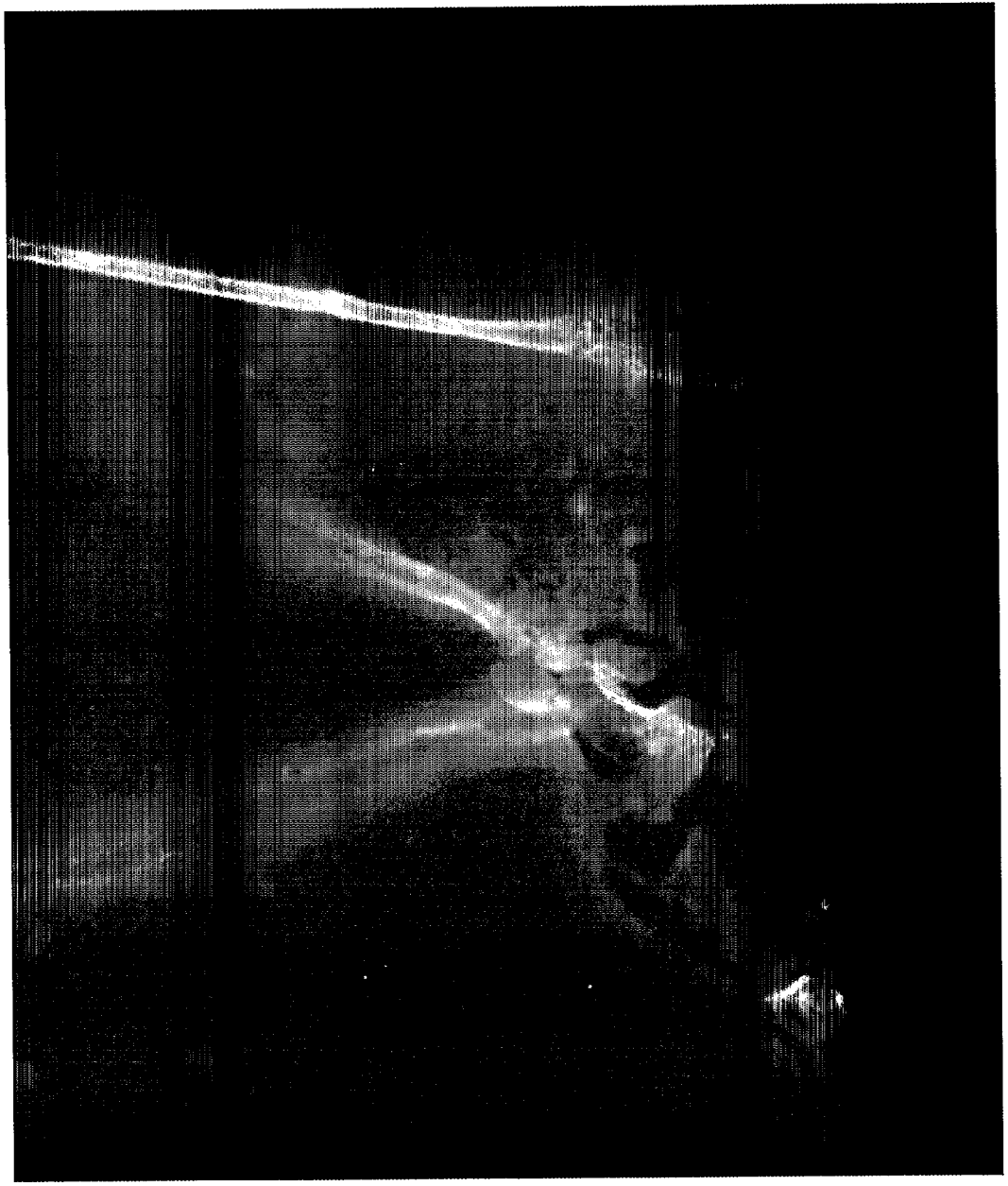
FIG. 11 shows a higher magnification of the fluorescence image shown in FIG. 10B.
Figure 12:
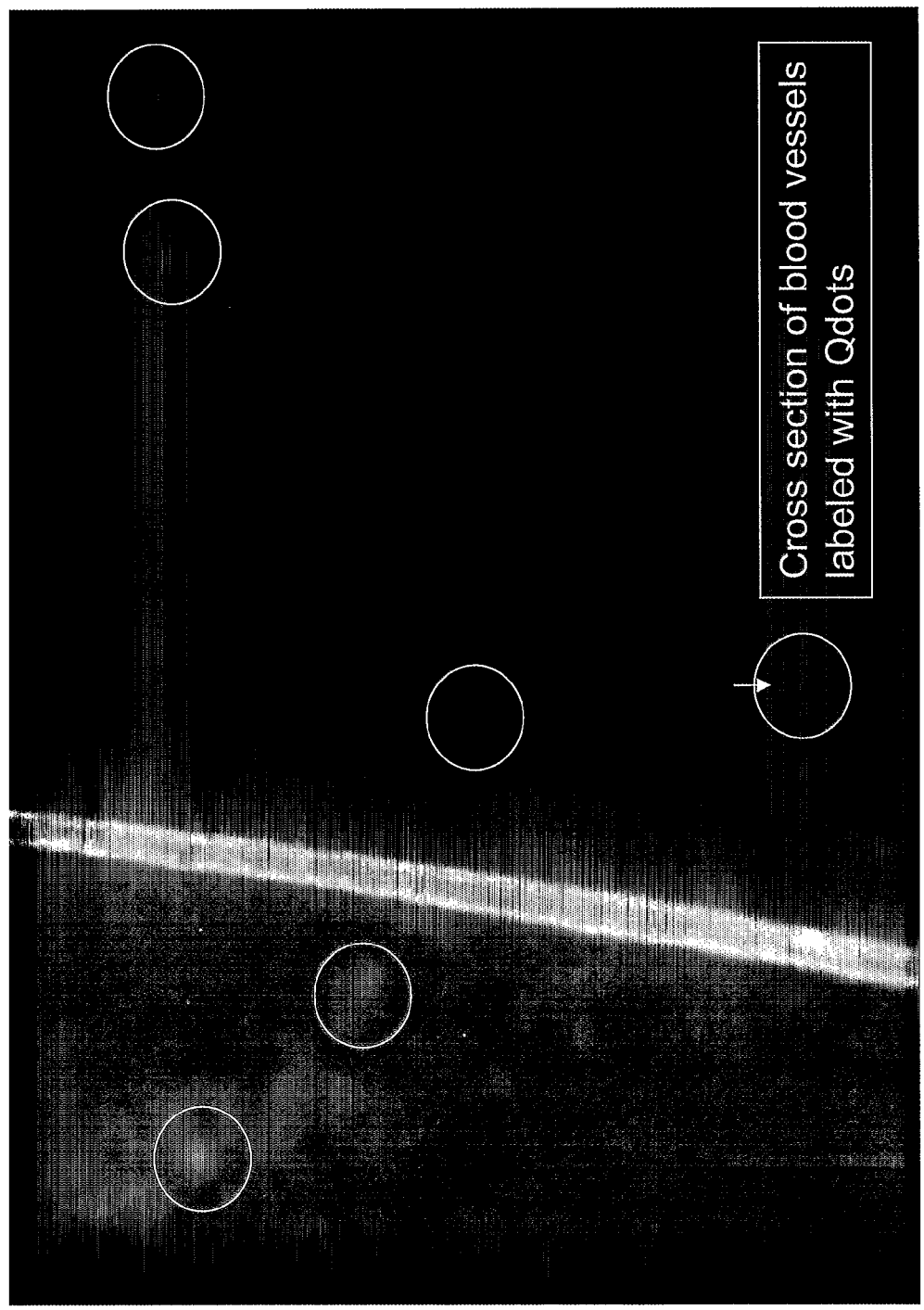
FIG. 12 shows cross sections of blood vessels labeled with the quantum dots of FIGS. 10A and 10B.

The magnetic properties of the quantum dots were studied by a SQUID magnetometer. About 10 mg of the quantum dots in powder form was inserted in a gelatin capsule for the magnetic measurement. The temperature-dependent applied field versus magnetization curves of Mn-doped and undoped core/shell quantum dots are shown in FIGS. 8A-8C and FIGS. 9A and 9B, respectively. As shown in FIGS. 8A-8C, Mn-doped core/shell quantum dots exhibit distinct transit with temperature from linear behavior (FIG. 8A) to hysterisis (FIG. 8C), indicative of their ferromagnetism at 300 K. However, undoped quantum dots show weak temperature-dependent magnetic behavior. Also note that there is a relatively large difference in magnetic responses (magnetization) of two types of quantum dots, i.e., $1.2 \times 10^{-5}$ (emu) of Mn-doped quantum dots versus $6 \times 10^{-6}$ (emu) of undoped counterparts at 1000 Oe of magnetic field measured at 300 K.

EXAMPLE 5

Synthesis of TAT-Conjugated Quantum Dots

Delivery of imaging and therapeutic agents to the brain is highly important for diagnosis and therapy of many brain diseases such as brain tumors. However, the delivery to these agents to the brain is often restricted by the BBB, a tight junction of endothelial cells that regulates the exchange of substances between brain and blood. Cell membrane is another natural barrier that also can restrict transport of these agents. A method to overcome the cellular membrane barrier is provided by the use of membrane translocation peptides such as TAT peptide (Dietz et al., *Mol. Cell. Neurosci.*, 2004, 27:85; Langel, Cell-Penetrating Peptides-Processes and Applications, CRC Press LLC, Boca Raton, 2002). This method has been successfully used to internalize various substances such as proteins, oligonucleotides, plasmid DNA and even nanoparticles (Fawell et al., *Proc. Natl. Acad. Sci. USA*, 1994, 91:664; Schwarze et al., *Science*, 1999, 285: 1569; Astriab-Fisher et al., *Pharm. Res.*, 2002, 19:744; Hellgren et al., *J. Drug Target*, 2004, 12:39; Zhao et al., *Bioconjugate Chem.*, 2002, 13:840; Santra et al., *Chem. Commun.*, 2004, 2810; Santra et al., *J. Am. Chem. Soc.*, 2005, 127:1656). The present inventors have demonstrated that it is possible to deliver various nanoparticle-based imaging agents into cells using TAT peptide-mediated delivery system.

For 2-pyridyl disulfide derivatized quantum dots, to 7 ml of silica-overcoated, surface-functionalized quantum dot solution, with approximate particle concentration of $10^{16}$/ml, is added 25 mg of N-succinimidyl 3-(2-pyridyldithio)propionate (SPDP) in 0.5 ml of dimethy sulfoxide (DMSO). The mixture is allowed to react for 12 hours at room temperature. Low molecular byproducts are removed via a gel permeation chromatography (GPC), equilibrated with 0.01 M tris base and 0.02 M citric acid, pH 7.4 buffer. To 7 ml of 2-pyridyl disulfide derivatized quantum dots is added 4 mg of TAT peptide (TAT peptide sequence: Gyl-Arg-Lys-Lys-Arg-Arg-Gln-Arg-Arg-Arg-Gly-Tyr-Cys-NH$_2$; 10 amino acid active component of TAT peptide is underlined) in 0.2 ml of DMSO. The mixture is allowed to react for 12 hours at room temperature. The TAT-conjugated quantum dots are centrifuged (8000 rpm, 8 minutes) and dispersed in DMSO.

EXAMPLE 6

Bioimaging Using TAT-Conjugated CdS:MN/ZnS Quantum Dots

For delivery of imaging/therapeutic agents to the brain at high concentration, a microcatheter based intra-arterial administration approach can be more attractive over the conventional intra-venous administration approach. Through intra-venous administration, agents are evenly distributed throughout the body. As a result, the availability of agents in the target site would be diluted by the loss of agent to non-targeted sites. However, using a microcatheter, agents can be administered intra-arterially to distal selective cerebral arteries in a human, at high concentration to a pre-selected area of the brain, permitting direct interaction with the target brain tissue.

In the present study, the intra-arterial approach was used to administer highly sensitive and photostable Qdots to the brain tissue. This approach results in high Qdot concentration at the target site. This technique, if applied to humans, could help neurosurgeons to clearly see (visualize) target brain tissues, such as brain tumors, during a surgical procedure. However, just having a suitable approach of administering Qdots may not be of assistance in brain imaging unless the following critical challenges are addressed. First, one must find a way to overcome the BBB to transport Qdots to the brain tissue. Second, Qdots must be rapidly transported from the blood vessels to the capillary endothelial cells to take the advantage of high local dosing of Qdots at the target site. To address these challenges, the present inventors provide a robust TAT peptide-mediated Qdot delivery technique that allows rapid and high dosing of Qdots in the brain tissue. To the present inventors' knowledge, this is the first demonstration of the application of TAT-Qdots for gross fluorescence visualization of a pre-selected rat brain tissue using a low power handheld light source. This technique can help doctors to clearly see pathological tissues such as brain tumors during a surgical procedure.

The present inventors have reported the synthesis and characterization of CdS:Mn/ZnS Qdots over-coated with a amine functionalized silica layer. Typically, Qdots were synthesized in a water-in-oil (dioctyl sulfosuccinate, sodium salt/heptane/water) microemulsion system where water droplets served as a nano-reactor. Amine functionalized silica overcoating, by which Qdots become highly water-soluble, was accomplished by the hydrolysis and co-condensation reaction of tetraethyl orthosilicate, 3-(aminopropyl) triethoxysilane and 3-(trihydroxysilyl)propyl methylphosphonate in the presence of ammonium hydroxide base. TAT peptide (the italicized amino acids in Gly-Arg-Lys-Lys-Arg-Arg-Gln-Arg-Arg-Arg-Gly-Tyr-Lys-Cys-NH$_2$) contained a cysteine (Cys) residue. The thiol (—SH) group of the cysteine was covalently attached to the amine group on the particle surface using a thiol-amine coupling agent, N-succinimidyl 3-(2-pyridyldithio)propionate. TAT-conjugated Qdots were completely dispersed in phosphate buffer saline (PBS) at pH 7.4.

Figure 13:
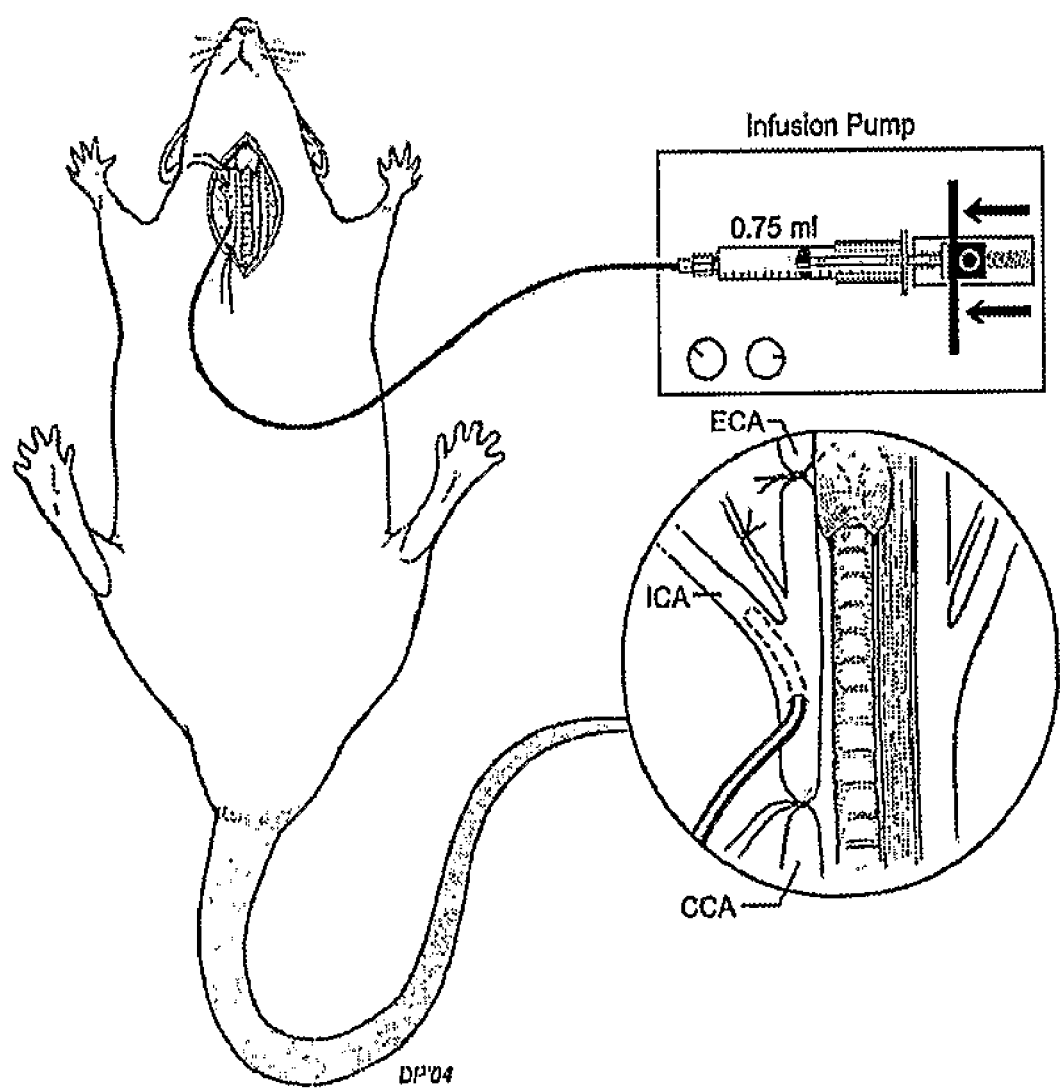
FIG. 13 shows a schematic representation of the surgical procedure for delivery of CdS:Mn/ZnS Qdots.

Sprague-Dawley rats (250-300 g) were used for in vivo experiments (Vives et al., *J. Biol. Chem.*, 1997, 272:16010). The infusion catheter was placed in a proximal, non-selective, cervical carotid artery in the rat, rather than a distal, selective, cerebral artery that would be used if performed in humans. This type of distal selective cerebral artery catheterization is routinely performed by physicians in humans, but is not possible in animal models because of the small size of their cerebral arteries. Rats were anesthetized with a Ketamine/Xylazine mixture (0.1 ml/100 g) administered intraperitoneally. The necks were shaved and prepped with chlorhexidine scrub. A 2-3 cm long incision was made on the neck. The right common carotid artery (CCA) was located and isolated from the surrounding tissue. A 4-0 silk suture was used to ligate the CCA proximally. Another length of suture was wrapped around the external carotid artery (ECA) and occipital artery to temporarily stop blood flow during injection of the substance into the internal carotid artery (ICA). A small catheter was placed in the right CCA and secured in place. FIG. 13 shows the schematic representation of the surgical procedure.

About 0.75 ml (10 mg/ml) of Qdot suspension in PBS was loaded into a syringe and placed into an infusion pump. The syringe was attached to the sheath and the pump was started. The infusion pump injected Qdots over a period of 5 minutes. At the same injection rate, PBS (pH 7.4) was then injected for 15 minutes to remove residual Qdots, which were not uptaken by the endothelial cells. The ECA was then opened and collateral blood flow allowed for 3 minutes. The rat was then euthanized with an overdose of sodium pentobarbital. A craniotomy was performed on the rat after euthanasia and the brain was removed. The whole brain was then immediately placed under a handheld 366 nm multi-band UV source (SPECTROLINE, model UV-4B) and photographed using a standard digital camera as shown in FIGS. 14A and 14B. The appearance of pink color in FIGS. 14A-C is due to Qdot fluorescence and the blue color originates from the background without Qdot labeling. Note that the presence of fluorescence on the medial aspect of the left hemisphere (FIGS. 14A and 14C) is secondary to the proximal, non-selective position of the catheter. This catheter position allows the Qdots to travel through the arterial communication between the medial hemispheres called the anterior communicating artery, which is a component of the Circle of Willis (connection of proximal cerebral arteries at the base of the brain). This would not occur in humans because the microcatheter would be placed far distal to the Circle of Willis. The time that it takes to stain brain tissues depends on the velocity of the cerebral blood flow, and is not significantly different when from a clinical perspective. The brain was then sliced into four 5 mm sections (one of the brain slices is shown in FIG. 14C) and placed into 10% buffered formalin. The tissue samples were then processed, embedded in paraffin, and two unstained slides were made from each section of brain for histological analysis. In addition, amine functionalized Qdots without TAT-conjugation were also tested as a control. However, no fluorescence was observed, confirming that these Qdots did not exhibit a labeling capability.

Figure 15A:
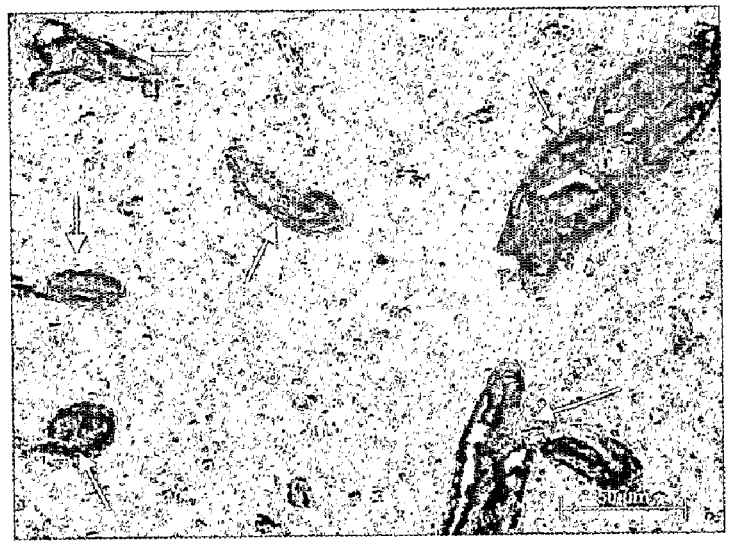
FIGS. 15A and 15B show transmission (FIG. 15A) and fluorescence (FIG. 15B) microscope images (magnification was 40×) of a cross-section of a fixed brain tissue, showing blood capillaries (distant branches of the middle cerebral artery as pointed with white arrows in FIG. 15A and the surrounding brain parenchyma (green circled brown dots around blood capillaries as shown in FIG. 15B, representing the nucleus of brain cells). Fluorescence images were taken using excitation bandpass 360/40, 400 dichroic longpass and emission bandpass 600/50 filters (obtained from Chroma Technology Corporation, Rockingham, Vt.).
Figure 15B:
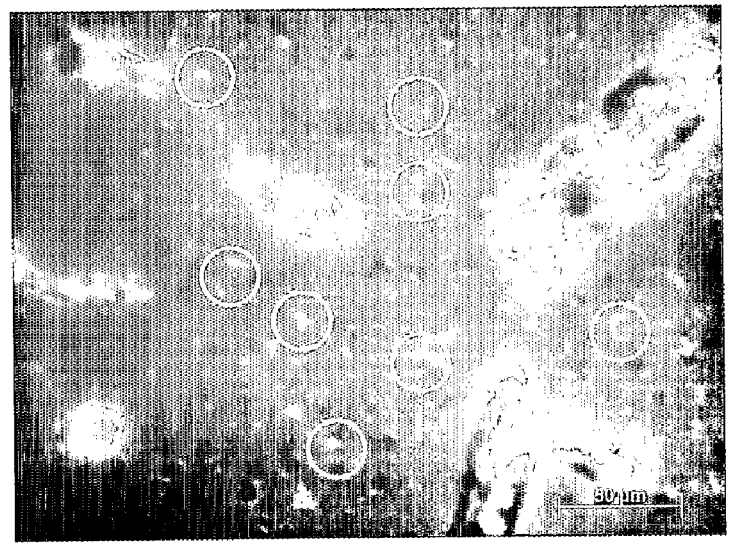

Gross visualization of the whole rat brain does not provide information in the cellular level. It is important to understand if TAT-conjugated Qdots penetrated the endothelial cells. There was also interest in whether Qdots were localized in the endothelial cell line or migrated further to reach brain parenchyma. Histological analysis, as shown in FIGS. 15A and 15B, was performed to obtain this information. FIGS. 15A and 15B showed transmission and fluorescence images of a cross section of a fixed brain tissue. Blood capillaries (distant branches of middle cerebral arteries) were shown with white arrows in FIG. 15A. The corresponding fluorescence image of Qdot labeled blood capillaries and surrounding brain cells in the brain parenchyma were clearly seen by Qdot fluorescence (FIG. 15B). It is also seen that TAT conjugated Qdots reached the nucleus of brain cells (as shown by green-circled brown spots in FIG. 15B).

It is known that TAT peptide can rapidly translocates through the plasma membrane and accumulate in the cell nucleus (Gao et al., 2004, *Nat. Biotechnol.*, 2004, 22:969). Our histological analysis of the brain tissue indeed supported the fact that TAT-Qdots crossed the BBB, further migrated to brain parenchyma and reached cell nucleus. As expected, endothelial cells in blood capillaries were highly loaded with Qdots and as a result they appeared bright yellow in FIG. 15B. FIGS. 10A-B, 11, and 12 show fluorescence microscope images of a cross-section of fixed brain tissue.

This study demonstrates rapid intra-arterial loading of yellow-emitting Qdots in a pre-selected brain tissue of a rat. The experimental data clearly showed that Qdot-loaded brain tissue could be visualized grossly (by a handheld UV excitation) as well as microscopically using a fluorescence microscope, confirming the fact that TAT peptide is responsible for a significant biological effect in labeling brain tissue. The present approach is useful for the visualization of tumors during the surgical procedure.

The present inventors have shown for the first time that ultra-small (3.1 nm) multifunctional semiconductor quantum dots (Qdots), that possess fluorescent, radio-opacity and paramagnetic properties in a single unit, may be synthesized. For bioconjugation, the present inventors have aminated the Qdot surface, completely prevented particle agglomeration and formed a stable aqueous suspension. The present inventors have conjugated Qdots with a TAT peptide. Using a rat model, the present inventors have successfully administered a Qdot suspension endovascularly. Histological analysis (using a fluorescence microscope) of the microtome sliced brain tissue clearly demonstrated the labeling efficacy of the Qdots. Because of their multifunctional properties, these Qdots can be widely used for in vivo bio-labeling, such as to target tumors, including brain tumors, as well as real-time tracking of cells, such as stem cells or other engineered cells, for certain disease diagnosis and therapy.

Materials and Methods (Example 6)

Synthesis of Qdots: In a typical synthesis, water-in-oil (W/O) microemulsion was used by mixing dioctyl sulfosuccinate, sodium salt (AOT, a surfactant), heptane (oil) and an aqueous salt solution. Aqueous solutions of ($Cd^{2+}+Mn^{2+}$), $S^{2-}$, and $Zn^{2+}$ were prepared from their precursor salts, $Cd(CH_3COO)_2 \cdot 2H_2O + Mn(CH_3COO)_2$, $Na_2S$, and $Zn(CH_3COO)_2$, respectively. Mn-doped CdS core Qdots were formed by mixing ($Cd^{2+}+Mn^{2+}$) and $S^{2-}$ containing microemulsions rapidly for 10-15 min. Then, $Zn^{2+}$-containing microemulsion was added at a very slow rate (1.5-2 ml/min) into the CdS:Mn Qdot containing microemulsion. To support ZnS shell growth onto CdS:Mn core Qdots, a surplus of sulfur ions was used. The concentrations of $Cd^{2+}$ and $Zn^{2+}$ ions in water are 0.1 and 0.26 M, respectively. The concentrations of water and AOT in heptane are 1 and 0.1 M, respectively, and the ratio of the solution concentrations of ZnS to CdS is 8. The molar ratio of water-to-surfactant (W), which determines the size of Qdots, is 10 for all of the ($Cd^{2+}+Mn^{2+}$)-, $S^{2-}$-, and $Zn^{2+}$-containing microemulsions. The actual Mn concentration in CdS was determined to be 1.8 mol % using inductively coupled plasma (ICP) analysis. The size of Qdots with a CdS:Mn/ZnS core/shell structure was found to be 3.1 nm with 6-8% variation in diameter.

Figure 16:
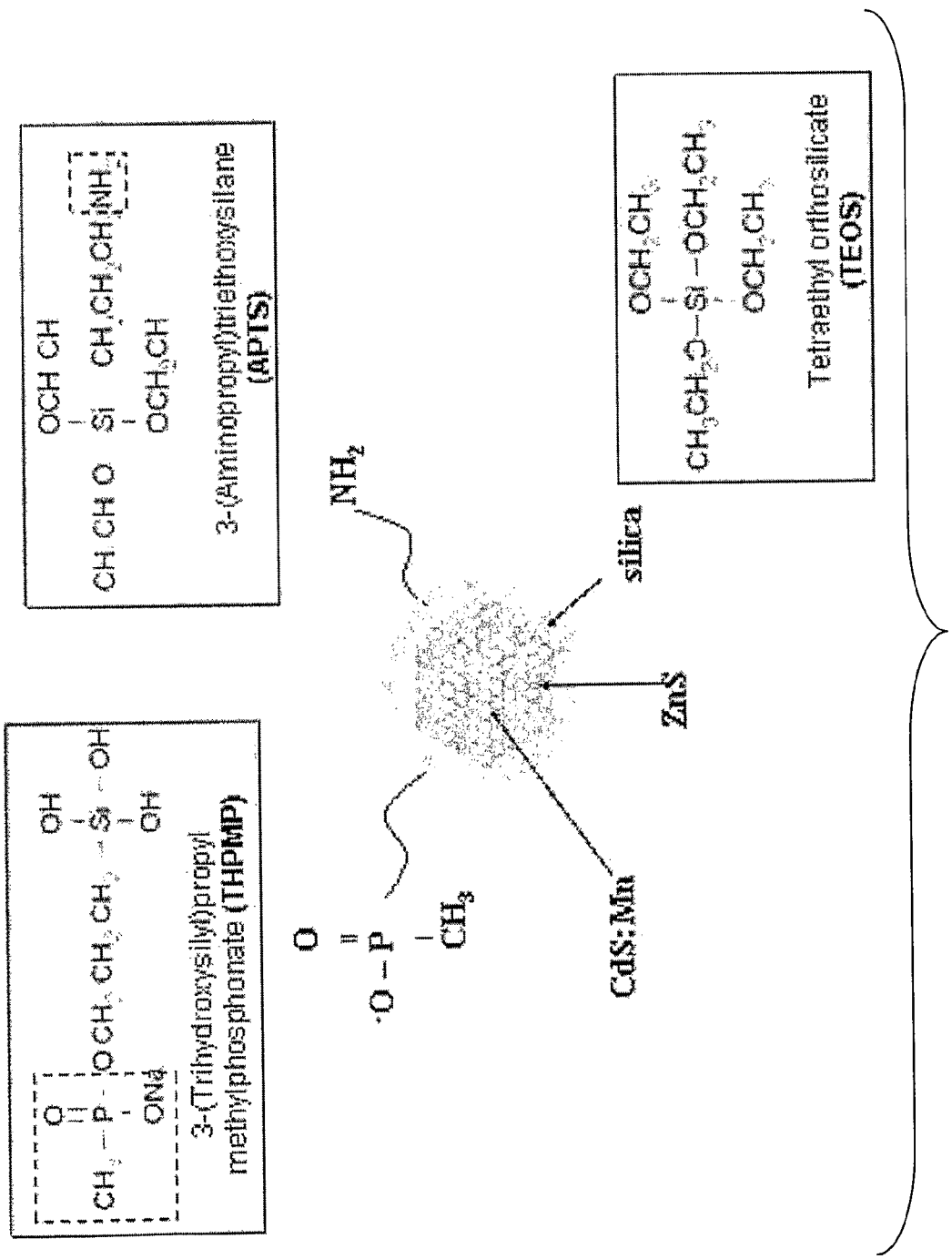
FIG. 16 shows a drawing of a surface-functionalized Qdot.

Water-dispersible amine functionalization: Highly water-dispersible silica (about 2.5 nm in thickness) coated Qdots were prepared by substantially modifying Schroedter's method. The hydrolysis and co-condensation reaction of tetraethyl orthosilicate (TEOS), 3-(aminopropyl) triethoxysilane (APTS) and 3-(rihydroxysilyl) propyl methylphosphonate (THPMP) led to a highly water-dispersible silica layer around each Qdot. Typically, after addition of the $Zn^{2+}$-containing microemulsion, 3.7 ml of TEOS is injected into CdS:Mn/ZnS Qdot microemulsion and mixed for 15 min at room temperature. The hydrolysis and condensation reactions are initiated by adding $NH_4OH$ in the form of microemulsion, which is prepared by mixing 2.22 ml of $NH_4OH$ (30 wt %) with AOT (5.5 g)/heptane (75 ml) stock solution. After condensation for 24 hr at room temperature, 1.85 ml of TEOS and 0.37 ml of APTS are injected into the above solution and mixed for 15 min. Subsequently another $NH_4OH$ microemulsion (prepared by mixing 1.32 ml of $NH_4OH$ with AOT (3.27 g)/heptane (30 ml) stock solution) and THPMP (prepared by mixing 1.11 ml of THPMP and 5.33 ml of water with AOT (6.55 g)/heptane (25 ml) stock solution) are injected and reacted for 24 hr. Silica surface-functionalized Qdots are precipitated by addition of a small amount of methanol. After a thorough washing with methanol, these Qdots are dispersed and stable in a phosphate buffer saline solution (PBS, pH 7.4). A drawing of a surface-functionalized Qdot is shown in FIG. 16.

Figure 17:
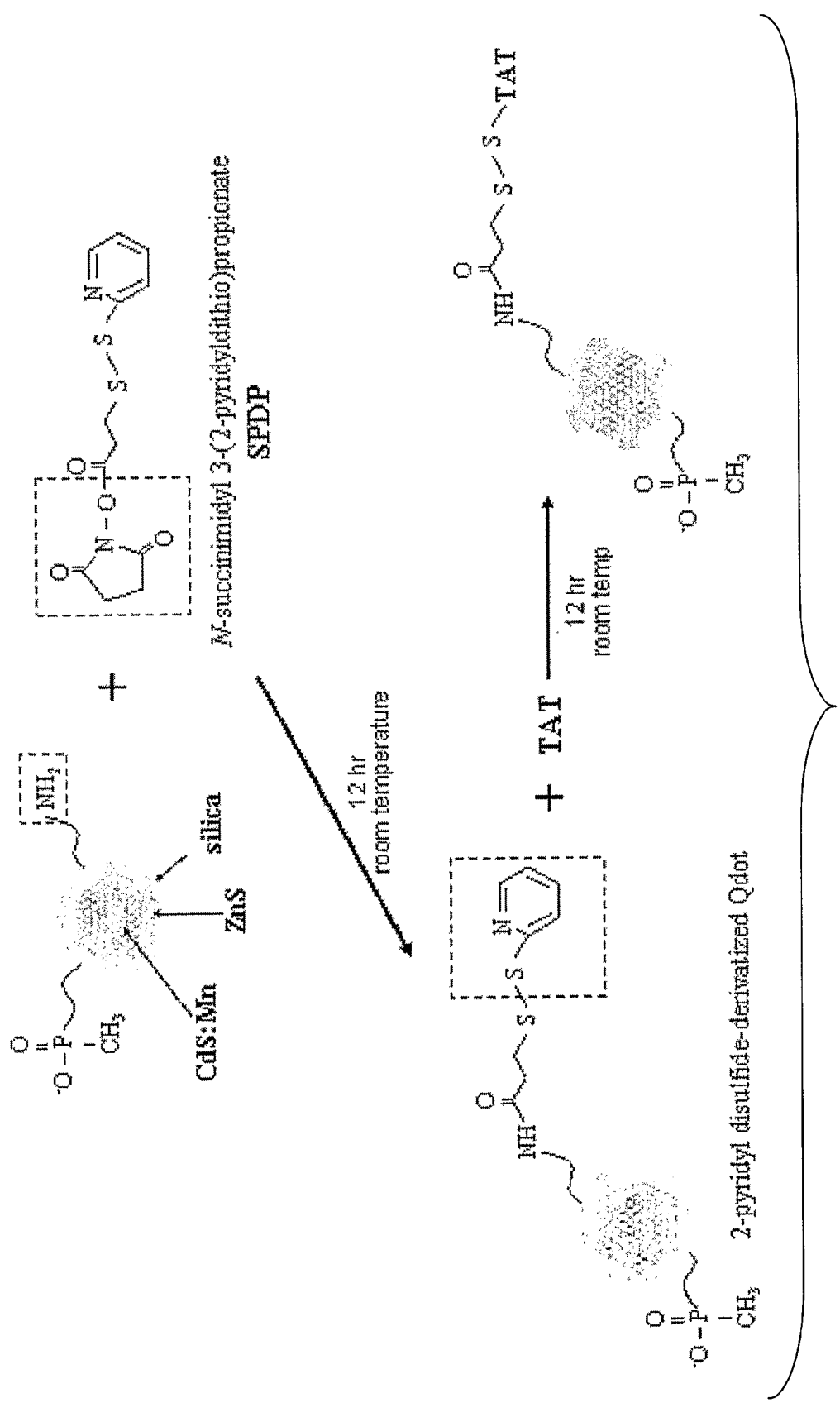
FIG. 17 shows a schematic of TAT-conjugation procedures using SPDP coupling chemistry.

TAT peptide-conjugation: Typically, a 7 ml Qdot solution (with approximate particle concentration of $10^{16}$/ml, 23 mg/ml) was added to 25 mg of N-succinimidyl 3-(2-pyridyldithio)propionate (SPDP) in 0.5 ml of dimethyl sulfoxide (DMSO). The mixture was allowed to react for 12 hr at room temperature. The 2-pyridyl disulfide derivatized quantum dots were precipitated with acetone/aqueous NaOH mixture, centrifuged and dispersed in PBS (pH 7.4). Starting with 7 ml of 2-pyridyl disulfide derivatized quantum dots, 4 mg of TAT peptide in 0.2 ml of DMSO was added. The mixture was allowed to react for 12 hr at room temperature. The TAT-conjugated Qdots were precipitated with ethanol, centrifuged and dispersed in a phosphate buffer solution. Typical TAT-conjugation procedures using SPDP chemistry are shown schematically in FIG. 17.

Figure 18B:
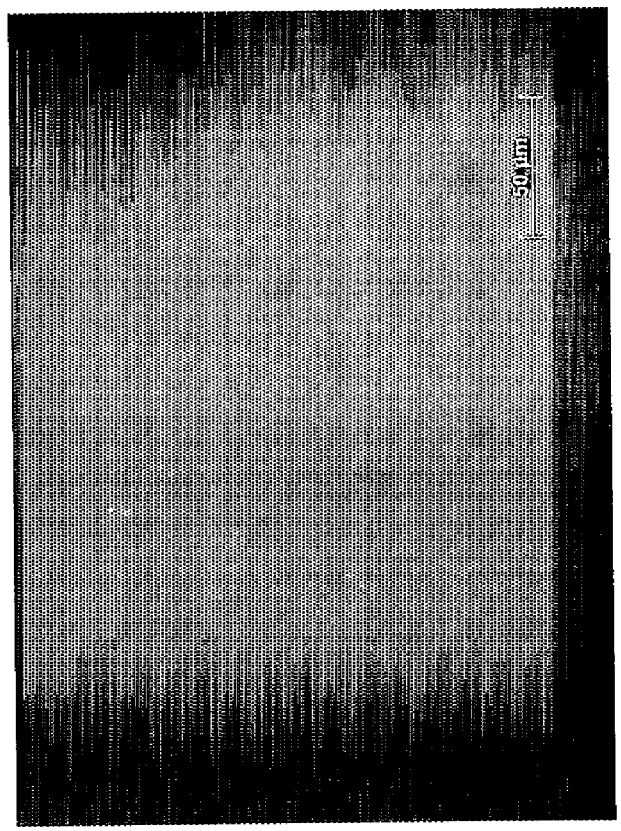
FIGS. 18A and 18B show transmission (FIG. 18A) and fluorescence (FIG. 18B microscope images (magnification was 40×) of a cross-section of a fixed brain tissue without any labeling. Fluorescence images were taken using excitation bandpass 360/40, 400 dichroic longpass and emission bandpass 600/50 filters (obtained from Chroma Technology Corporation, Rockingham, Vt.).
Figure 18A:

Autofluorescence study of brain tissue: In order to determine whether or not there is any autofluorescence from rat brain tissue, histological analysis of the tissue sample was performed. FIGS. 18A and 18B show the transmission (FIG. 18A) and fluorescence (FIG. 18B) images of the brain sample with the same filter setup as described with FIGS. 15A and 15B. From the fluorescence image (FIG. 18B) it was clearly seen that autofluorescence from the native brain tissue was negligible.

EXAMPLE 7

Synthesis and Characterization of Fluorescent, Radio-Opaque and Paramagnetic Silica Nanoparticles for Multi-Modal Bio-Imaging Applications Described below is the water-in-oil (W/O) microemulsion synthesis and characterization of 100 nm (±10 nm) size tris (2,2'-bipyridyl) dichlororuthenium (II) hexahydrate (Rubpy) and gadolinium ($Gd^{3+}$) doped silica (Rubpy:Gd (III)/$SiO_2$) nanoparticles. These nanoparticles were fluorescent, radio-opaque and paramagnetic as characterized by fluorescence, fluoroscopic (X-ray) and magnetic measurements, respectively. To enable bioconjugation, the nanoparticle surface was modified to attach primary amine groups. To verify MRI (magnetic resonance imaging) contrast, nanoparticles were compared with a commercially available paramagnetic MRI contrast agent, Prohance® and it was found that nanoparticles showed better MRI contrast. From ICP (Inductively Coupled Plasma) analysis, it was estimated that each nanoparticle carried about 16,000 $Gd^{3+}$ ions. The better MRI contrast from nanoparticles is probably due to the presence of substantially large amount of $Gd^{3+}$ ions. Since nanoparticles are fluorescent, radio-opaque and paramagnetic, they have potential for multimodal bioimaging (imaging at multiple modes) applications.

A multifunctional contrast agent with optical, radio-opaque and magnetic properties would be particularly useful in the preoperative diagnosis and the intraoperative surgical resection of brain tumors or other surgical lesions. The synthesis of bifunctional contrast agents for dual (fluorescence and magnetic) imaging was reported by others in which organic fluorescent dyes were used. However, the use of organic dyes may not be suitable for real-time imaging as these dyes often undergo rapid photobleaching process. The present inventors designed a one-pot synthesis and characterization of engineered multifunctional single-core multiple-shell novel Rubpy:Gd (III)/$SiO_2$ nanoparticles. Advantageously, these nanoparticles are photostable, radio-opaque and paramagnetic leading to the possibility of a general purpose molecular probe, which could be visualized using CT, MRI, and diffuse optical tomography. Furthermore, the surface reactive groups of this probe can be modified to contain both ligands and antibodies allowing for the detection of cellular events in vivo.

The optical component of the proposed system is Rubpy, a highly sensitive and photostable dye (Santra et al., *Analytical Chemistry*, 2001, 73:4988; Santra et al., *Journal of Biomedical Optics*, 2001, 6:160) shown in FIG. 19, that is doped into the silica core of the particles. The magnetic component of the nanoparticle is paramagnetic gadolinium (III) ions, which were attached to the hydrated silica shell through a silane ligand. The X-ray contrast (radio-opacity) of the nanoparticles results from the electron dense metal ions: both ruthenium and gadolinium.

Figure 20:
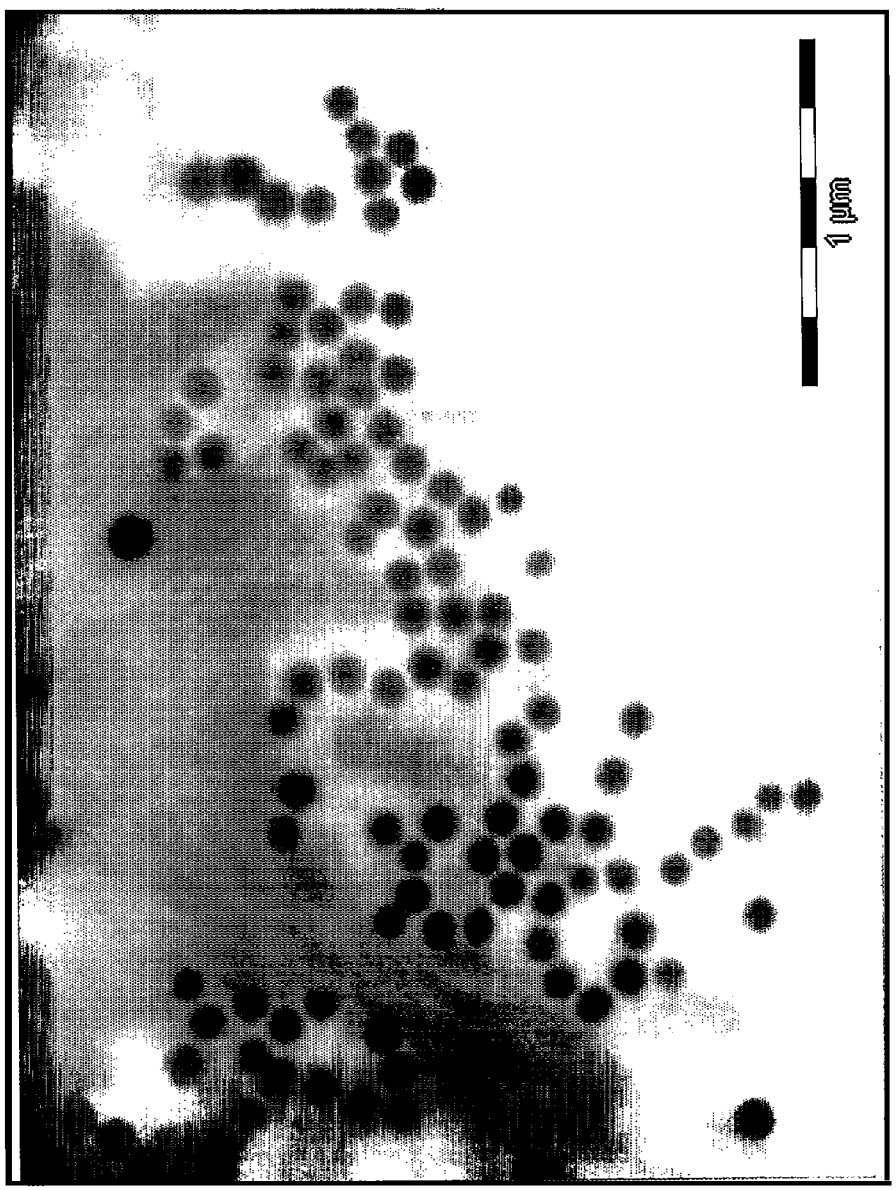
FIG. 20 shows a transmission electron micrograph of Rubpy:Gd (III)/$SiO_2$ nanoparticles. The average nanoparticle size was 100 nm.

The W/O microemulsion is an isotropic, thermodynamically stable single-phase system that consists of three components: water, oil, and an amphiphilic molecule (surfactant). The water nanodroplets present in the bulk oil phase serve as a reactor for the synthesis of nanoparticles (Santra et al., *Analytical Chemistry*, 2001; Santra et al., *Journal of Biomedical Optics*, 2001; Arriagada et al., 1999, 211:210; Santra et al., *Langmuir*, 2001, 17:2900). Rubpy:Gd (III)/$SiO_2$ nanoparticles were synthesized using a Triton X-100/cycloxehane/n-hexanol/water W/O microemulsion system (Santra et al., *Analytical Chemistry*, 2001; Santra et al., *Journal of Biomedical Optics*, 2001; Santra et al., *Chemical Communications*, 2004, 24:2810). The transmission electron microscopic (TEM) image of the nanoparticles (FIG. 20) shows uniform particle size, demonstrating the robustness of the W/O microemulsion technique. The average particle size was 100 nm.

Figure 21A:
FIGS. 21A-21C show, respectively, digital image (FIGS. 21A and 21B) of Rubpy:Gd (III)/$SiO_2$ nanoparticle aqueous solution (right) and DI water (left) under a 366 nm multiband hand held UV illumination (Spectroline, model UV-4B)
Figure 21B:
Figure 21C:
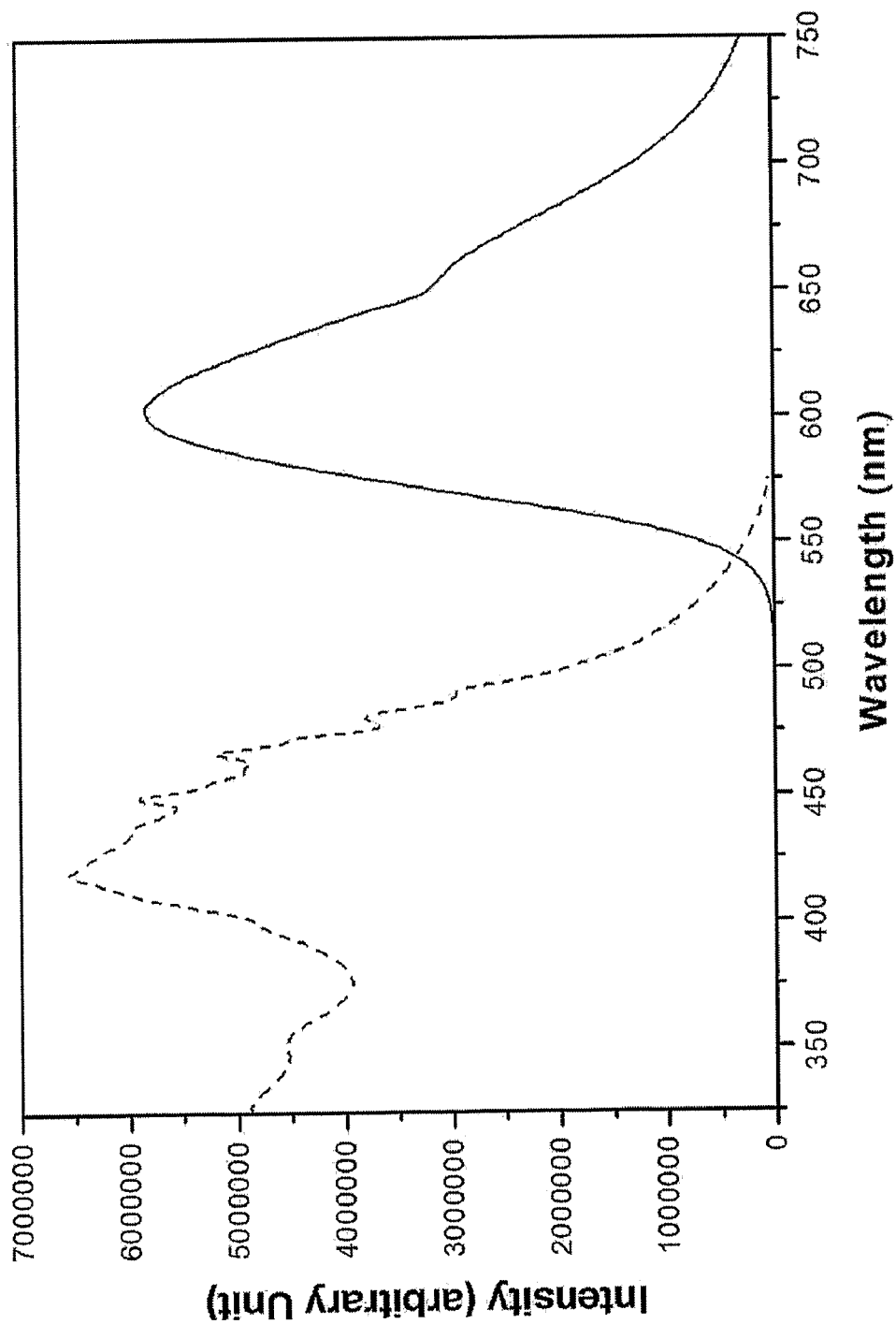

The nanoparticle optical core (FIG. 19) was designed to isolate and protect Rubpy from the outside environment. Dye molecules remain well encapsulated by the optically transparent silica matrix, protected from photobleaching (Santra et al., *Analytical Chemistry*, 2001; Santra et al., *Journal of Biomedical Optics*, 2001). FIGS. 21A-21B show the fluorescence image (orange-red emission) of particles dispersed in water (FIG. 21B) illuminated with a hand-held UV excitation source, with DI water as a non-fluorescent control (FIG. 21A). The fluorescence excitation and fluorescence emission spectra of the nanoparticles are shown in FIG. 21C. The spectral characteristics (excitation and emission wavelengths) of Rubpy in the nanoparticles were found to be unchanged from those of the pure fluorophore (Santra et al., *Analytical Chemistry*, 2001; Santra et al., *Journal of Biomedical Optics*, 2001).

The nanoparticle inner magnetic shell was designed to capture paramagnetic gadolinium ($Gd^{3+}$) ions. The present inventors have identified a silane reagent, n-(trimethoxysilyl-propyl)ethyldiamine, triacetic acid trisodium salt (TSPETE) that captured $Gd^{3+}$ ions efficiently. Similar to other $Gd^{3+}$ capturing macrocyclic ligands such as DOTA (1,4,7,10-tet-raazacyclododecane-1,7-bis(acetic acid-t-butyl ester)-4,10-acetic acid), DOTP (p-aminobenzyl-diethylenetriaminepenta (acetic acid-t-butyl ester)), TSPETE has reactive coordination sites for capturing $Gd^{3+}$ ions. ICP (inductively coupled plasma) spectroscopy and fluoroscopy studies of $Gd^{3+}$/$SiO_2$ nanoparticles (without Rubpy dye doping), confirmed successful binding of $Gd^{3+}$ ions in the silica nanoparticles (results not shown).

Figure 22:
FIG. 22 shows a fluoroscopy (X-ray) image of Rubpy:Gd (III)/$SiO_2$ (left) and Omnipaque™ (right). Concentration was 20 mg/ml for both samples. Pure silica nanoparticles did not show any contrast to X-ray (image not shown).

Fluoroscopic images clearly demonstrated that the nanoparticles were radio-opaque (FIG. 22). The nanoparticles were compared to the most common contrast agent, Omnipaque™ at equal concentrations of 20 mg/ml. Although the Omnipaque™ showed stronger radio-opacity, it is believed that the nanoparticle synthesis protocol can be optimized to improve radio-opacity. The same set of experiments showed pure silica particles to be transparent to X-rays (image not shown).

Figure 23A:
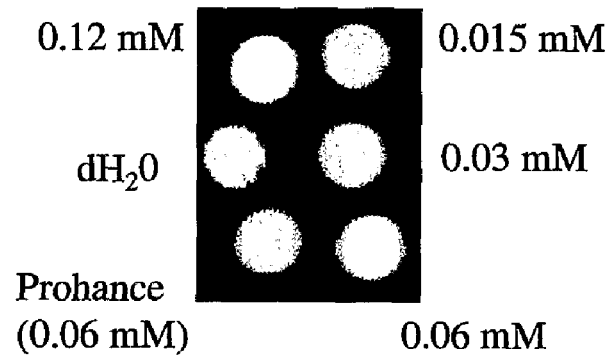
FIGS. 23A-23D show MRI measurements of multifunctional Rubpy:Gd (III)/SiO2 nanoparticles. Nanoparticles generated MR contrast on both T1 (FIG. 23A) and T2 (FIG. 23C) weighted sequences. Normalized image intensity versus repetition time (TR) and echo time (TE) are shown in FIG. 23B and FIG. 23D, respectively, for nanoparticles containing 0.12 mM (purple diamonds) and 0.06 mM (green triangles) Gd3+ ions; 0.06 mM Prohance (red circles) and $dH_2O$ (blue circles). A linear relationship was observed when gadolinium concentration in the nanoparticle was plotted against (1/T1) and (1/T2) as shown in the insets of FIGS. 23B and 23D. Proton relaxativity values (R1 and R2) were determined based on these linear relationships.
Figure 23C:
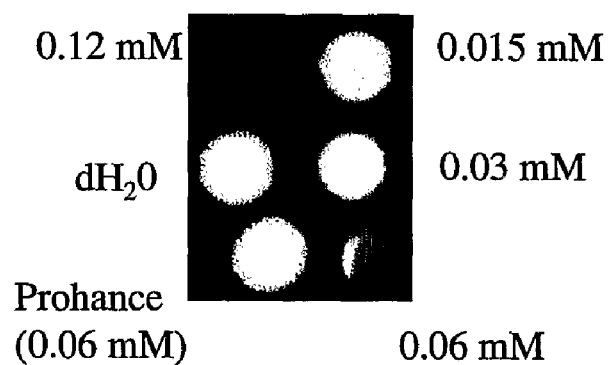
Figure 23B:
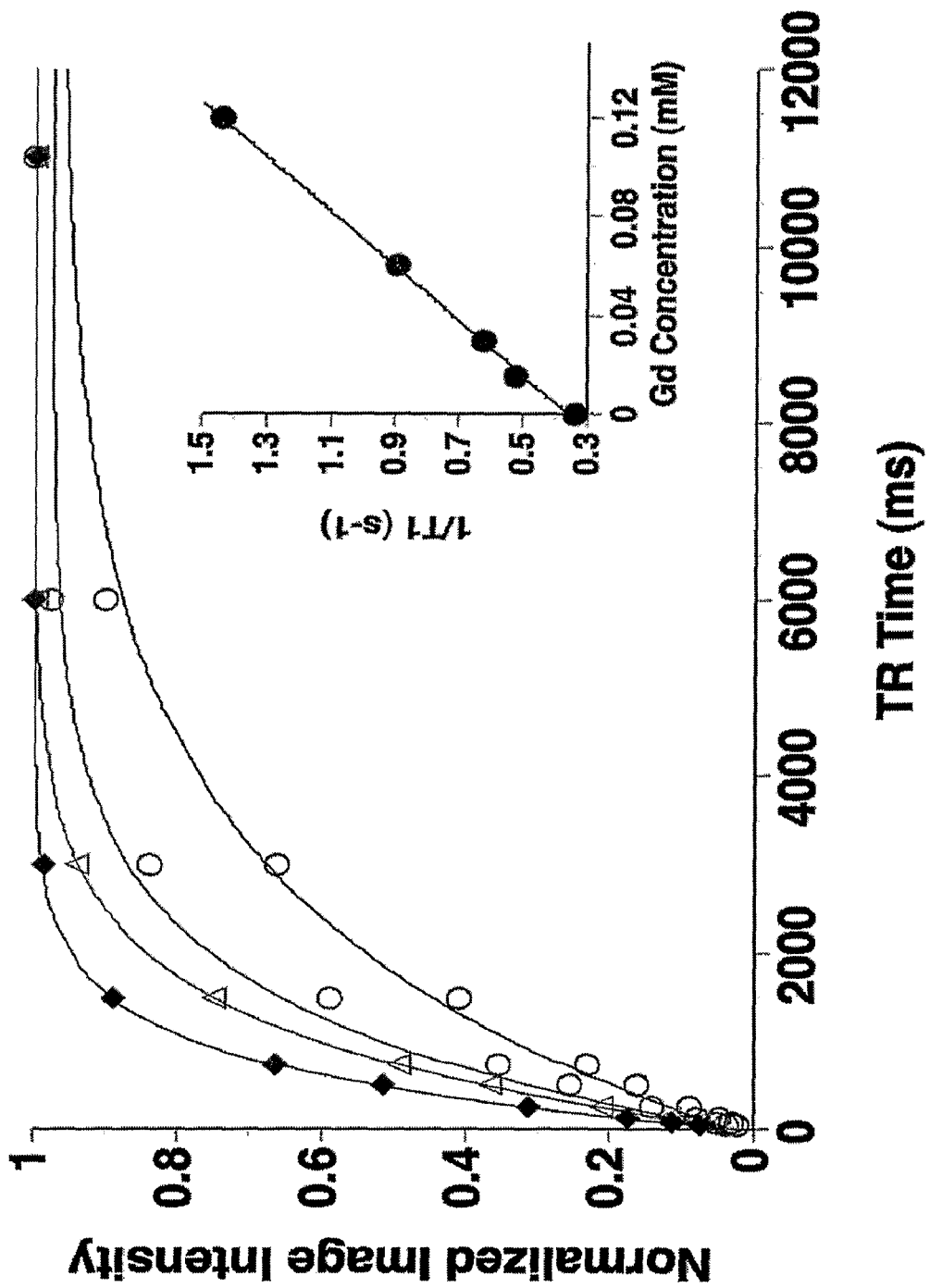
Figure 23D:
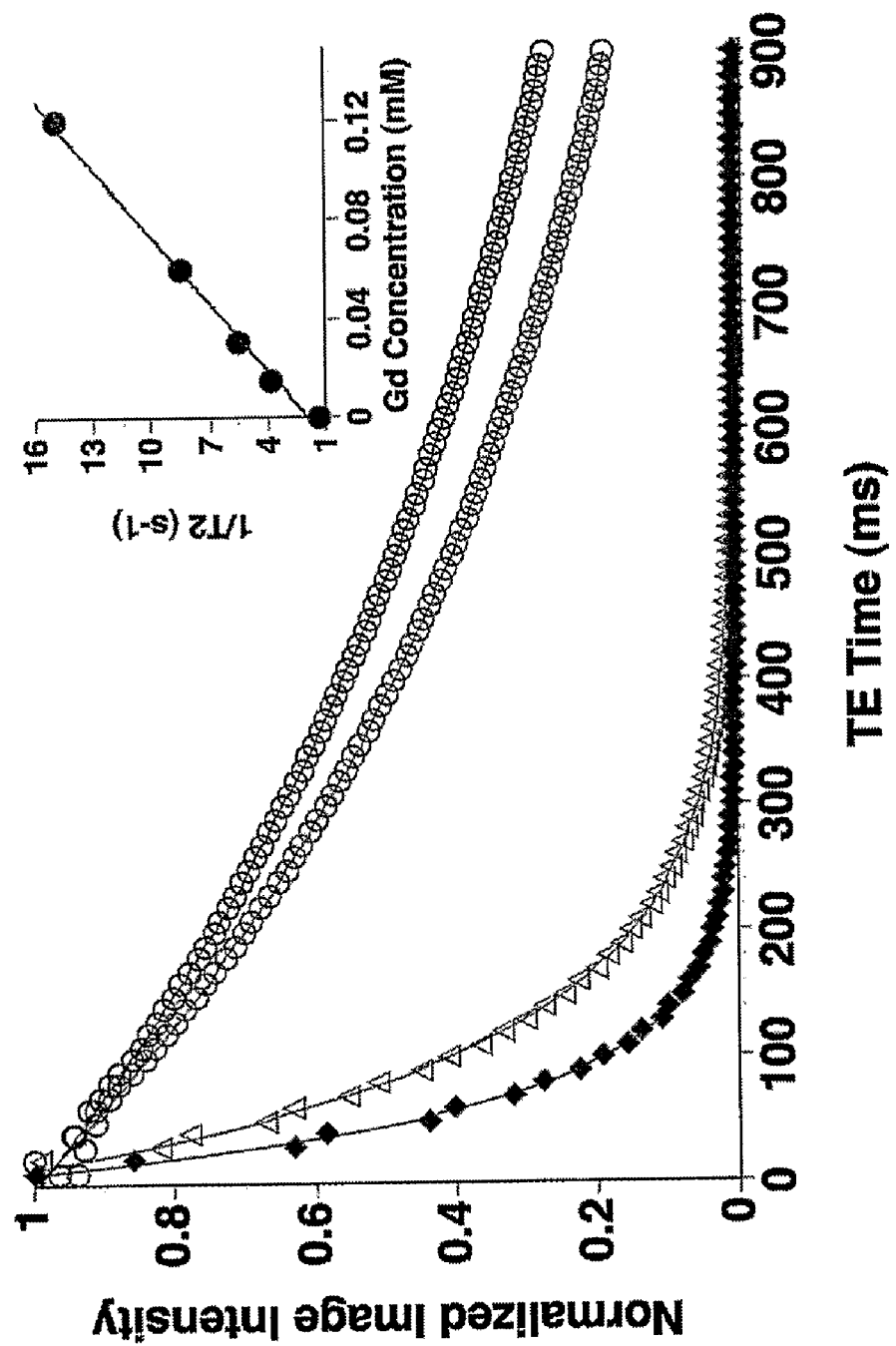

Nanoparticles generated MR contrast on both $T_1$ (FIG. 23A) and $T_2$ (FIG. 23C) weighted sequences. Furthermore, changes in longitudinal ($T_1$) and transverse proton relaxation ($T_2$) times as a function of nanoparticle concentration were calculated and directly compared to relaxation times using a commercially available MRI contrast agent (Gadoteridol, Gd-HP-DO3A; known as Prohance®) at 4.7T (Bruker, Avance). The proton $T_1$ and $T_2$ relaxativities ($R_1$, $R_2$) were calculated by measuring the change in $T_1$ and $T_2$ at increasing concentrations of nanoparticles in distilled water ($dH_2O$) using progressive saturation and multiple spin-echo imaging sequences. This is shown in FIGS. 23A-23D, where FIG. 23A contains a $T_1$ weighted image (TR=500 ms, TE=4.2 ms) of distilled water, Gd-HP-DO3A, and serial dilutions of the nanoparticle (containing 0.12, 0.06, 0.03, 0.015 mM $Gd^{3+}$). FIG. 5A demonstrates the ability of this nanoparticle to act as a strong $T_1$ contrast agent generating more signal than an equal concentration of Gd-HP-DO3A on $T_1$ weighted images. Normalized image intensity versus repetition time (TR) and echo time (TE) are shown in FIG. 23B and FIG. 23D, respectively for nanoparticles containing 0.12 mM and 0.06 mM $Gd^{3+}$ ions; 0.06 mM Prohance® and $dH_2O$. A $R_1$ of 9.0 $s^{-1}$ mM $Gd^{-1}$ was determined based on the linear relationship between $(1/T_1)$ and gadolinium concentration in the nanoparticle determined by ICP (FIG. 23B). Nanoparticle ion $R_1$ was found to be 2.3 times more than that of commercially available Gd-HP-DO3A. FIGS. 23C and 23D show the similar inverse relationship of MR signal intensity and $T_2$ on nanoparticle concentration. On $T_2$ weighted images (FIG. 23C; TE=140 ms, TR=12 s) increasing concentrations of nanoparticles lead to a dramatic decrease in signal intensity due to $T_2$ shortening (FIG. 23D). The experimentally determined ion $R_2$ based on the relationship between $(1/T_2)$ and gadolinium concentration was 116 $s^{-1}$ mM $Gd^{-1}$, and was 24 times the ion $R_2$ for Gd-HP-DO3A (FIG. 23D inset). These MR studies clearly showed that $Gd^{3+}$ ions, which are bound to nanoparticles can result in image contrast on both $T_1$ and $T_2$, weighted images to larger extent than a commonly used MR contrast agent. Due to the much larger $R_2$ than $R_1$ we anticipate that this probe will function best as a $T_2$ contrast agent in vivo. Moreover, based ICP data, we have estimated that about 16,000 $Gd^{3+}$ ions were bound to each nanoparticle which is a higher than the 60-1,331 $Gd^{3+}$ ions per particle reported for poly-lysine and G6 based dendrimer contrast agents and the 24-90 $Gd^{3+}$ per targeted contrast agent typically reported (Caravan et al., 1999, *Chemical Reviews*, 99:2293). This contrast agent is similar to a previously much larger nanoparticle (Morawski et al., *Magnetic Resonance in Medicine*, 2004, 51:480), which contained 94,000 $Gd^{3+}$ on an approximately 250 nm particle with an ion $R_1$ of 9.7 $s^{-1}$ mM $Gd^{-1}$ at 200 MHz. The much larger $R_2$ observed with this particle when compared to Prohance® warrants further investigation.

Figure 19:
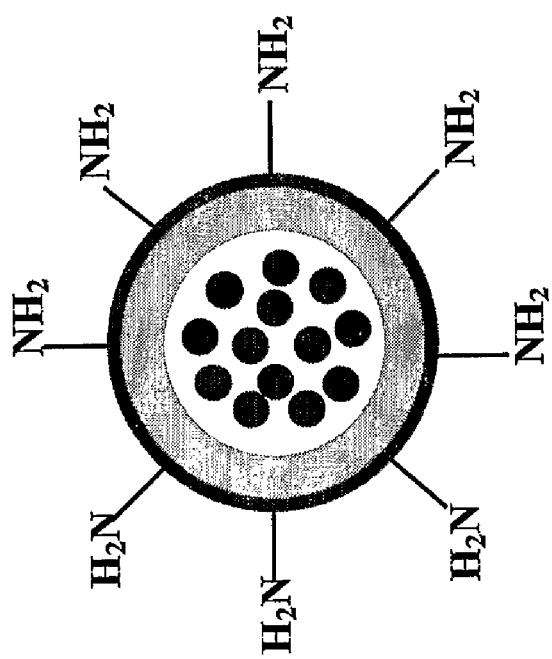
FIG. 19 shows a drawing of the single core-multiple shell Rubpy:Gd (III)/$SiO_2$ nanoparticle design.

For bioconjugation, it is desirable to (i) prepare a highly dispersed aqueous nanoparticle suspension at physiological conditions (e.g., in buffer solution, pH 7.4) and (ii) obtain suitable functional groups on the nanoparticle surface. Following Schroedter's protocol (Schroedter et al., *Angewandte Chemie-International Edition*, 2002, 41:3218) with a slight modification (Santra et al., *Chemical Communications*, 2004), nanoparticles were surface modified. The hydrolysis and co-condensation reaction of tetraethyl orthosilicate (TEOS), 3-(aminopropyl) triethoxysilane (APTS) and 3-(trihydroxysilyl)propyl methylphosphonate (THPMP) produced highly water dispersible amine functionalized nanoparticles (FIG. 19). Pure silica nanoparticles (pKa=7.0) are water dispersible (zeta potential, ξ is about −40 mV). Surface modification with the positively charged APTS (pKa=9.0) dropped the potential close to the isoelectric point (ξ~0.5 mV). The addition of negatively charged THPMP (pKa=2) compensated for the effect of positively charged APTS and restored nanoparticle water dispersibility by increasing the overall zeta potential value to approximately −35 mV.

In summary, the present inventors have successfully developed monodisperse fluorescent, radio-opaque and paramagnetic Rubby:Gd (III)/$SiO_2$ nanoparticles, wherein the Gd ion is contained within the silica shell. Use of this nanoparticle synthesis strategy will allow doping of a wide variety of fluorescent dye molecules (e.g., organic, metallorganic, quantum dots, near-infrared etc.) and paramagnetic materials (e.g., gadolinium ions, iron oxide nanoparticles etc.). These nanoparticles have strong potential for multimodal bioimaging applications.

EXAMPLE 8

Figures 27A, 27B, 27C:
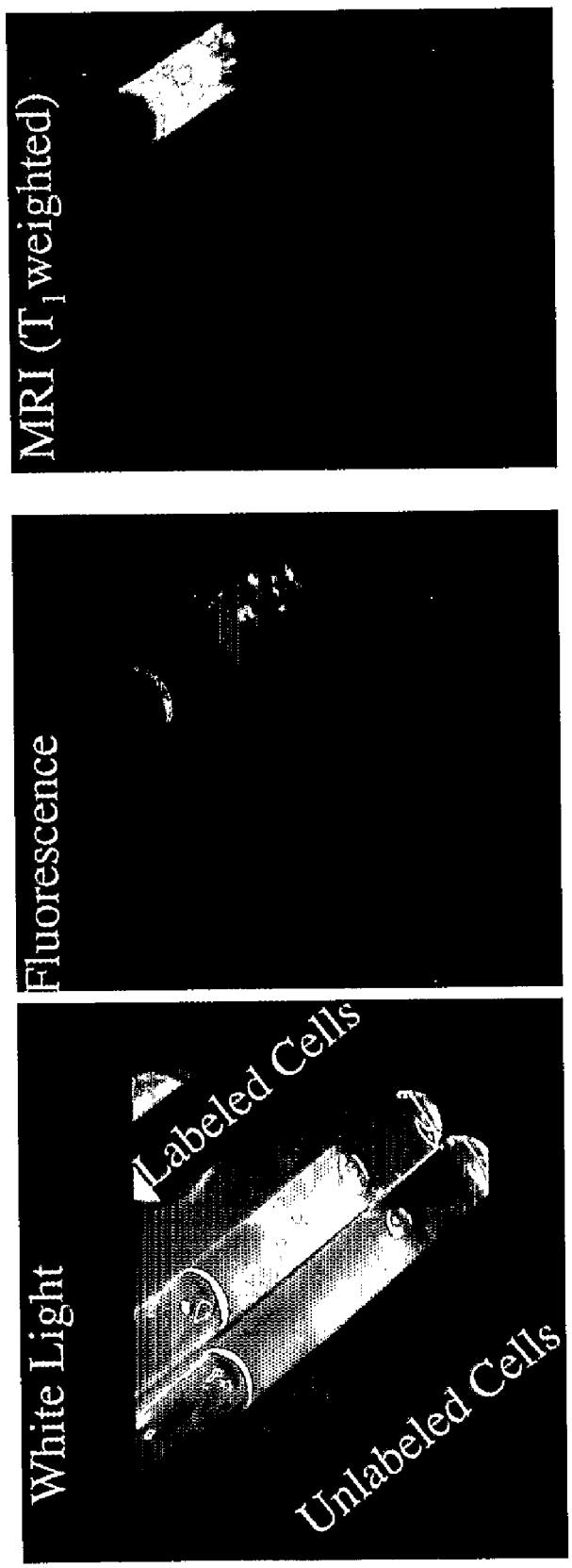
FIGS. 27A-27C show results of an experiment demonstrating multimodal bioimaging capability of folate-Rubpy:Gd/SiO2 nanoparticle. Human lung adenocarcinoma (A-549 cells) were loaded with nanoparticles.

Targeting of Fluorescent, Radio-Opaque and Paramagnetic Rubpy:Gd (III)/$SiO_2$ Nanoparticles to Tumor Cells with Positive MRI Contrast The present inventors found that folic acid-labeled Rubpy: Gd (III)/$SiO_2$ nanoparticles could be used to perform multimodal imaging of human lung adenocarcinoma cells (A-549 cells). When $1\times10^6$ adenocarcinoma cells were incubated with a folic acid labeled Rubpy:Gd (III)/$SiO_2$ nanoparticle and then subsequently suspended in 2% agarose between layers of agarose not containing cells, positive contrast was observed under UV epifluorescence (as observed under a fluorescent stereomicroscope with the rhodamine filters and captured using a color CCD) and T1 weighted MRI at 4.7T. This is shown in FIGS. 27A-27C. MR images of nanoparticle labeled cells also resolved clusters of cells within the agarose. Control cells incubated without the folic acid-labeled nanoparticle did not result in positive fluorescence or T1 contrast. Thus, these studies demonstrate that this nanoparticle has the potential to simultaneously detect cancerous cells non-invasively using MRI and optical imaging.

EXAMPLE 9

Activatable Rubpy:Gd (III)/$SiO_2$ Nanoparticles

The Rubpy:Gd (III)/$SiO_2$ nanoparticles described in Example 7 have gadolinium ion (Gd) instead of Mn, and the Gd ion is contained within the silica shell. Next, the present inventors designed nanoparticles in which the Gd ion is on the outside of the silica shell, adjacent to surface functional amine groups, making the nanoparticles activatable. This is very important because the present inventors have observed positive MRI contrast, which is primarily generated by the interaction between the water in the environment and the Gd ion.

Figure 28B:
FIGS. 28A and 28B show Gd-Qdot-labeled muscle myoblast and Gd-Qdot-labeled muscle derived stem cells.
Figure 28A:

The present inventors have observed that this nanoparticle can generate positive MRI contrast (T1) both in solution and within cells. This finding is very important for several reasons. First, the present inventors have demonstrated that there is enough exchangeable water within cells to interact with the nanoparticle and to generate positive T1 contrast. Second, this exchange mechanism provides a way in which an activatable contrast agent can be produced. The present inventors have made these nanoparticles active in the presence of a common gene marker, beta-galactosidase. Third, this nanoparticle can be used to label a number of mouse and human stem cells (as shown in FIGS. 28A and 28B, respectively) without the use of any special targeting sequence. In this case, the surface charge on the molecule has been adjusted to result in high water solubility as well as cellular uptake in the presence of cationic gene transfection agents (i.e., poly-1-lysine). Thus, activation of the contrast agent can be achieved by exchange between cellular water and the Gd ion. This interaction is initially inhibited in the absence of the enzyme beta-galactosidase because the nanoparticle is coated with galactose, which will block the interaction between water and Gd. If the enzyme, beta-galacatosidase, is present it will operate to digest the sugar coating (galactose) on the particle, allowing cellular water to interact with Gd and produce T1 contrast visible by MRI. The present inventors have initially chosen this beta-galactosidase mechanism because beta-galactosidase is a common maker used in development biology and gene and cell therapy studies. However, there are other possible sugars that could be used to coat this nanoparticle that would be informative in a number of clinical trials aimed at the treatment of genetic diseases, such as glycogen storage disease. In this case, the particle can be coated with a glycogen or glucose molecule, for example, that would only be metabolized allowing water exchange with Gd when the missing gene or enzyme is replaced.

In another embodiment, an FDA approved near-infrared contrast agent can be used instead of the quantum dot core. The use of a near infrared fluorophore would permit deep tissue imaging without the use of UV illumination. For example, a nanoparticle that contains ICG (the FDA approved NIR contrast agent) and the present inventors have shown in an optical imaging setup that it can be used as a NIR contrast agent. The coupling of the FDA approved MRI and optical contrast agents should eliminate some of the hurdles towards studies in humans.

EXAMPLE 10

Dysprosium (Dys) Nanoparticles for High Magnetic Fields

Another embodiment of the nanoparticle of the invention involves replacement of the Gd ion with dysprosium (Dys). MR contrast agents, such as Gd, do not increase their ability to act as contrast agents above strength at fields above 4 Tesla. Dys is one of the only MRI contrast agents that has been shown to increase contrast with a magnetic field. Therefore, the addition of Dys to the outer shell (coating) of the nanoparticle will render the nanoparticle more sensitive at higher magnetic fields than Gd. Currently, the highest magnetic field that is FDA approved is only 3 Tesla; however, whole body clinical scanners are available at magnetic field strengths from 7 to 9.4 Tesla. Some research institutions have MRI scanners with magnetic fields as high as 21 Tesla available for the imaging of biological samples and small animals.

Figure 29:
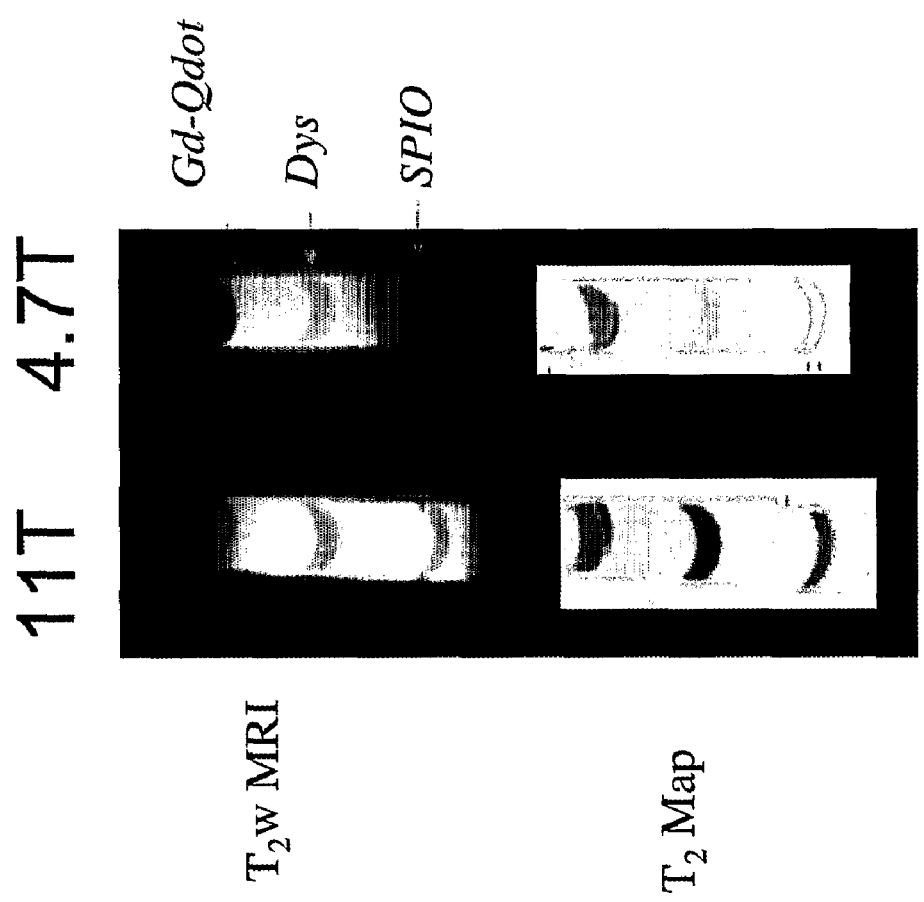
FIG. 29 shows T2 Weighted images (top) and quantitative T2 maps (bottom) of an agarose phantom constructed form (Gd-Qdot nanoparticle; top layer), Dysprosium nanoparticle (middle layer), and SPIO (Feridex; Berlex Labs). Phantoms were images at 11T (left) or 4.7T (right).

FIG. 29 shows T2 Weighted images (top) and quantitative T2 maps (bottom) of an agarose phantom constructed form (Gd-Qdot nanoparticle; top layer), Dysprosium nanoparticle (middle layer), and SPIO (Feridex; Berlex Labs). Phantoms were images at 11T (left) or 4.7T (right).

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A composition comprising a multi-functional contrast agent and a pharmaceutically acceptable carrier, wherein said contrast agent comprises a CdS:Mn/ZnS core/shell quantum dot, wherein said quantum dot is fluorescent, radio-opaque, and paramagnetic, and wherein said CdS:Mn/ZnS core/shell quantum dot further comprises a Gd(III)/SiO$_2$ coating (outer shell) or a Dys/SiO$_2$ coating (outer shell).

2. The composition of claim 1, further comprising a pharmaceutically active agent.

3. A multi-functional contrast agent comprising a CdS:Mn/ZnS core/shell quantum dot, wherein said quantum dot is fluorescent, radio-opaque, and paramagnetic, and wherein said CdS:Mn/ZnS core/shell quantum dot further comprises a Gd (III)/SiO$_2$ coating (outer shell) or a Dys/SiO$_2$ coating (outer shell).

4. The contrast agent of claim 3, wherein said contrast agent further comprises a targeting moiety conjugated to said quantum dot.

5. The contrast agent of claim 3, wherein said contrast agent further comprises a targeting moiety conjugated to said quantum dot, wherein said targeting moiety comprises a TAT peptide or folic acid.

6. The contrast agent of claim 3, wherein said contrast agent further comprises a coating and a targeting moiety conjugated to said coating.

7. The contrast agent of claim 3, wherein said ZnS shell of said contrast agent is amine functionalized.

8. The contrast agent of claim 3, wherein said contrast agent further comprises an amine functionalized silica coating around said ZnS shell.

9. The contrast agent of claim 3, wherein said quantum dot is water-dispersable.

10. The contrast agent of claim 3, wherein said quantum dot is doped with a fluorescent dye molecule or a paramagnetic material, or both.

11. The contrast agent of claim 3, wherein said quantum dot further comprises a coating that renders said contrast agent activatable in a cell.

12. The contrast agent of claim 3, wherein said quantum dot further comprises a coating that renders said contrast agent activatable in a cell, and wherein said coating is a carbohydrate selected from the group consisting of galactose, glycogen, or glucose.

13. The contrast agent of claim 3, wherein said quantum dot comprises said Gd(III)/SiO$_2$ coating (outer shell), and wherein said quantum dot further comprises a carbohydrate that blocks the ninth coordination site of Gd in the absence of a carbohydrate-degrading enzyme.

14. The contrast agent of claim 3, wherein said contrast agent is associated with at least a portion of an implantable or deployable medical device.

* * * * *

UNITED STATES PATENT AND TRADEMARK OFFICE
CERTIFICATE OF CORRECTION

PATENT NO. : 8,128,908 B2
APPLICATION NO. : 10/590590
DATED : March 6, 2012
INVENTOR(S) : Swadeshmukul Santra et al.

It is certified that error appears in the above-identified patent and that said Letters Patent is hereby corrected as shown below:

Column 31,
Line 22, "(ph 7)" should read --(ph~7)--.

Column 32,
Lines 41-42, "$Mn^{2+} 4T_1$-$^6A_1$" should read --$Mn^{2+}\ ^4T_1$-$^6A_1$--.

Signed and Sealed this
Eighth Day of May, 2012

David J. Kappos
*Director of the United States Patent and Trademark Office*